(12) United States Patent
Cameron et al.

(10) Patent No.: US 7,414,071 B2
(45) Date of Patent: Aug. 19, 2008

(54) METHODS OF TREATMENT WITH SELECTIVE EP4 RECEPTOR AGONISTS

(75) Inventors: Kimberly O. Cameron, East Lyme, CT (US); Bruce A. Lefker, Gales Ferry, CT (US); Delvin R. Knight, Jr., Ledyard, CT (US)

(73) Assignee: Pfizer Inc., New York, NY (US)

( * ) Notice: Subject to any disclaimer, the term of this patent is extended or adjusted under 35 U.S.C. 154(b) by 890 days.

(21) Appl. No.: 10/386,307

(22) Filed: Mar. 11, 2003

(65) Prior Publication Data

US 2003/0207925 A1    Nov. 6, 2003

Related U.S. Application Data

(60) Provisional application No. 60/365,711, filed on Mar. 18, 2002.

(51) Int. Cl.
*A61K 31/40* (2006.01)
*A61K 31/41* (2006.01)
*A61K 31/38* (2006.01)

(52) U.S. Cl. .................. 514/422; 514/382; 514/381; 514/424; 514/438

(58) Field of Classification Search ........... 514/438, 514/444–449, 422, 424, 381, 382
See application file for complete search history.

(56) References Cited

U.S. PATENT DOCUMENTS 6,747,054 B2 *   6/2004   Cameron et al. ............ 514/422

FOREIGN PATENT DOCUMENTS

WO         WO 00/38667       *   7/2000

* cited by examiner

*Primary Examiner*—Shengjun Wang
(74) *Attorney, Agent, or Firm*—Bryan C. Zielinski; Wendy L. Hsu

(57) ABSTRACT

The present invention provides a method of treating hypertension, liver failure, loss of patency of ductus arteriosus, glaucoma or ocular hypertension in a patient, comprising administering to the patient a therapeutically effective amount of a selective $EP_4$ receptor agonist of Formula I

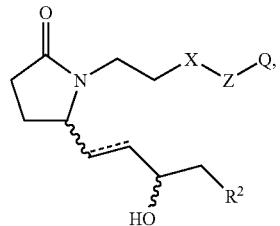

or a prodrug thereof, a pharmaceutically acceptable salt of the selective $EP_4$ receptor agonist or prodrug or a stereoisomer or diastereomeric mixture of the $EP_4$ receptor agonist, prodrug or salt, wherein the variables X, Z, Q, ⁓⁓⁓, and $R^2$ are as defined in the specification.

9 Claims, No Drawings

METHODS OF TREATMENT WITH SELECTIVE EP4 RECEPTOR AGONISTS

CROSS-REFERENCE TO RELATED APPLICATION

This application claims priority from U.S. provisional application No. 60/365,711 filed on Mar. 18, 2002.

FIELD OF THE INVENTION

The present invention relates to methods for the treatment of disorders responsive to modulation of the prostaglandin $E_2$ receptor, in a patient in need thereof, by administration of a receptor selective prostaglandin $E_2$ agonist. More specifically, the present invention provides methods for the treatment of hypertension, liver failure, loss of patency of the ductus arteriosus, glaucoma or ocular hypertension in a patient in need thereof by administration of a selective prostaglandin $E_2$ type 4 receptor agonist.

BACKGROUND OF THE INVENTION

The naturally occurring prostaglandins are comprised of several biological entities including prostaglandin E (PGE). Prostaglandin $E_2$ (abbreviated as $PGE_2$ herein) is known to be a cyclooxygenase induced oxidative metabolite in the arachidonic acid cascade, and it has been well documented that prostaglandins, including $PGE_2$, have effects on many of the organs and systems of the body. For example, it is known that $PGE_2$ has cyto-protective activity, uterine contractile activity, a pain-inducing effect, a promoting effect on digestive peristalsis, an awakening effect, a sleep-inducing effect, a suppressive effect on gastric acid secretion, hypotensive activity and diuretic activity. In previous studies it has been found that the $PGE_2$ receptor has various subtypes, each possessing differing physiological roles. At this time, it is known that the $PGE_2$ receptor has four primary subtypes denoted $EP_1$, $EP_2$, $EP_3$ and $EP_4$, each of which mediates different effects in various tissues and cells (Coleman, R. A. et al., Pharm. Rev. 1994, 46(2), 205-229). The $EP_4$ receptor is distributed in such organs as the thymus, heart, kidney, liver, intestine, womb, ductus arteriosus and bone, and it is known that the $EP_4$ receptor is related to relaxation of smooth muscle, differentiation and proliferation of lymphocytes, proliferation of mesangial cells, and collagen production of the fibroblasts. In both the pig and the dog, modulation of the $EP_4$ receptor has been characterized with relaxation of the saphenous vein, and in the rabbit relaxation of the jugular vein occurs (Coleman, R. A. et al., Prostaglandins 1994, 47, 151).

The $EP_4$ receptor is also expressed in the ductus arteriosus (Bhattacharya, M. et al., Circulation 1999, 100, 1751-1756). The ductus arteriosus is an arterial connection in the fetus, which directs blood away from the pulmonary circulation and towards the placenta where oxygenation occurs (Heymann, M. A.; Rudolph, A. M. Physiol. Rev. 1975, 55, 62-78). In one proposed model the $EP_4$ receptor in the ductus arteriosus acts as a sensor that responds to the perinatal drop in circulating levels of $PGE_2$ by triggering closure of the ductus arteriosus (Nguyen, M. et al., Nature 1997, 390, 78-81). Closure of the ductus arteriosus was observed in an in vivo fetal sheep model after administration of a selective $EP_4$ antagonist (PCT International Application WO 01/42281, published on Jun. 14, 2001). Maintaining the ductus arteriosus in the open, or patent state is desirable in the fetus and in infants with certain types of congenital heart defects where pulmonary or systemic blood flow depends on patency of the ductus arteriosus. Maintaining patency of the ductus arteriosus in infants with certain other types of congenital heart disease such as coarctation of the aorta, transposition of the great arteries, and Ebstein's anomaly may also be desirable. For example, infants with coarctation of the aorta, a condition constituting 7% to 8% of congenital cardiac defects, may have sudden onset of heart failure, cardiovascular collapse, and severe metabolic acidosis as the ductus arteriosus closes and distal perfusion is compromised. In cases such as these, $PGE_1$ infusions have been utilized to reopen and maintain the patency of the ductus arteriosus prior to surgical repair of the defect.

An excess of aqueous humor in the anterior chamber of the eye can result in elevated intraocular pressure or ocular hypertension. Ocular hypertension is a symptom and/or risk factor for glaucoma, a disease that can damage the optic nerve and cause blindness. The $EP_4$ receptor has been found in ocular tissues involved in the production of the aqueous humor, such as human ciliary epithelial cells and human ciliary muscle cells (Mukhopadhyay et al., Biochem. Pharmacol. 1997, 53, 1249-1255). Trabecular meshwork cells are known to be involved in the regulation of intraocular pressure (Clark et al., Investigative Opthalmology & Visual Science 1994, 35, 281-294; and Lutjen-Drescoll, Progress in Retinal and Eye Research 1998, 18, 91-119). The $EP_4$ receptor has also been found in human trabecular meshwork cells and it has been proposed that activation of the $EP_4$ receptors in the trabecular meshwork cells can result in relaxation of these cells, thereby lowering intraocular pressure (PCT International Patent Application WO 00/38667, published on Jul. 6, 2000).

As $PGE_1$ and $PGE_2$ bind to all four of the $PGE_2$ receptor subtypes ($EP_1$, $EP_2$, $EP_3$, and $EP_4$), various physiological activities may result, some of which may be an undesired side effect due to the lack of selectivity in binding to the $PGE_2$ receptor subtypes. It is therefore desirable to have methods of treatment for various disorders comprising administration of compounds with selectivity to a particular $PGE_2$ receptor subtype.

Great Britain Patent Specification 1 553 595 discloses compounds of the formula

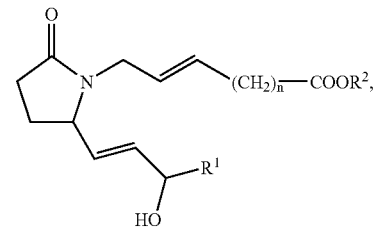

wherein the double bonds are cis or trans and the variables are defined as set forth therein. Those compounds are disclosed as having spasmogenic and spasmolytic activity, for example bronchodilatory and antihypertensive effects. The compounds are also disclosed as having utility in the inhibition of the secretion of gastric juice and as having abortive effects.

U.S. Pat. No. 4,115,401 discloses compound of the formula wherein the variables are defined as set forth therein. Those compounds are disclosed as having spasmogenic, cardiovascular and bronchodilatory effects.

U.S. Pat. No. 4,113,873 discloses compound of the formula

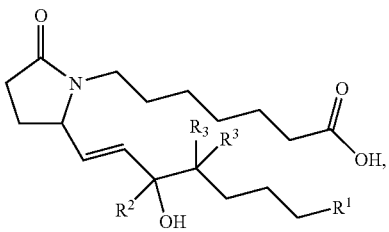

wherein the variables are defined as set forth therein. Those compounds are disclosed as having utility as a bronchodilator, as an antihypertensive agent, as an enhancer of spontaneous contraction of the uterus and for the treatment of gastrointestinal disorders or gastric ulcers.

Great Britain Patent Specification 1 583 163 discloses compounds of the formula

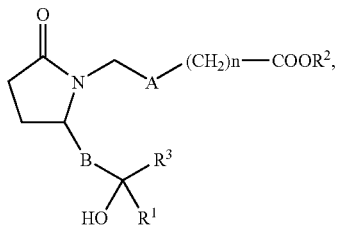

wherein the variables are defined as set forth therein. Those compounds are disclosed as having spasmogenic, bronchodilatory, vasoconstricting, vasodilating and abortive properties as well as utility in the inhibition of gastric acid secretion.

U.S. Pat. No. 4,177,346, discloses compounds of the formula

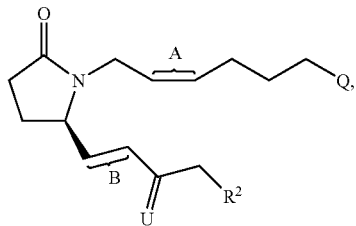

wherein the variables are defined as set forth therein. Those compounds are disclosed as having vasodilator, antihypertensive, bronchodilator, antifertility and antisecretory activity.

U.S. Patent Application Publications Nos. US 2001/0041729, which published on Nov. 15, 2001, and US 2001/0047105, which published on Nov. 29, 2001, disclose methods of treatment with compounds of the formula

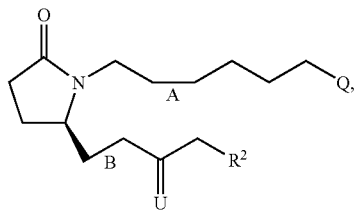

wherein the variables are defined as set forth therein. The methods of treatment disclosed in US 2001/0041729 include the treatment of acute or chronic renal failure or dysfunction, or a condition caused thereby, such as hypertension, congestive heart failure, glomerulonephritis, uremia or chronic renal insufficiency. The methods of treatment disclosed in US 2001/0047105 include the treatment of conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth.

U.S. patent application Ser. No. 09/990,556, which was filed on Nov. 21, 2001, discloses compounds of the formula

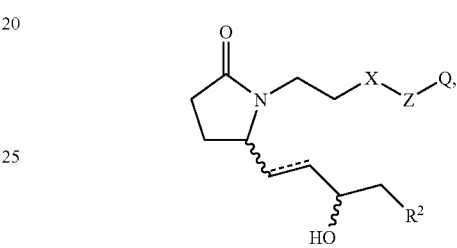

wherein the variables are as defined therein. The compounds are useful for the treatment of conditions which present with low bone mass such as osteoporosis, frailty, an osteoporotic fracture, a bone defect, childhood idiopathic bone loss, alveolar bone loss, mandibular bone loss, bone fracture, osteotomy, bone loss associated with periodontis or prosthetic ingrowth.

There exists a continuing need and a continuing search in this field of art for methods of treating hypertension, liver failure, loss of patency of the ductus arteriosus, glaucoma and ocular hypertension. More specifically, there is a need for methods of treating hypertension, liver failure, loss of patency of the ductus arteriosus, glaucoma or ocular hypertension in a patient in need thereof with selective prostaglandin receptor agents that do not have the undesired side effects caused by methods of treatment with non-selective agents.

SUMMARY OF THE INVENTION

The present invention is directed to methods of treating hypertension, liver failure, loss of patency of the ductus arteriosus, glaucoma or ocular hypertension in a patient, comprising administering to the patient a selective $EP_4$ receptor agonist or a prodrug thereof, or a pharmaceutically acceptable salt of the selective $EP_4$ receptor agonist or prodrug.

A first embodiment of the present invention is directed to methods of treating hypertension, liver failure, loss of patency of ductus arteriosus, glaucoma or ocular hypertension in a patient, comprising administering to the patient a therapeutically effective amount of a selective $EP_4$ receptor agonist of Formula I

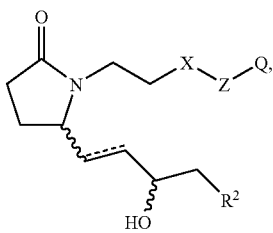

or a prodrug thereof, a pharmaceutically acceptable salt of the selective EP$_4$ receptor agonist or prodrug or a stereoisomer or diastereomeric mixture of the EP$_4$ receptor agonist, prodrug or salt, wherein:

- - - - is a single or double bond;

X is —CH$_2$— or O;

Z is —(CH$_2$)$_3$—, thienyl, thiazolyl or phenyl, provided that when X is O, then Z is phenyl;

Q is carboxyl, (C$_1$-C$_4$)alkoxylcarbonyl or tetrazolyl;

R$^2$ is —Ar or —Ar$^1$—V—Ar$^2$;

V is a bond, —O—, —OCH$_2$— or —CH$_2$O—;

Ar is a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, said partially or fully saturated ring or bicyclic ring optionally having one or two oxo groups substituted on carbon or one or two oxo groups substituted on sulfur; and Ar$^1$ and Ar$^2$ are each independently a partially saturated, fully saturated or fully unsaturated five to eight membered ring optionally having one to four heteroatoms selected independently from oxygen, sulfur and nitrogen, said partially or fully saturated ring optionally having one or two oxo groups substituted on carbon or one or two oxo groups substituted on sulfur;

said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, (C$_1$-C$_7$)alkoxy, (C$_1$-C$_4$)alkoxy(C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$)alkyl, (C$_3$-C$_7$)cycloalkyl(C$_1$-C$_4$)alkanoyl, formyl, (C$_1$-C$_8$)alkanoyl, (C$_1$-C$_6$)alkanoyl(C$_1$-C$_6$)alkyl, (C$_1$-C$_4$)alkanoylamino, (C$_1$-C$_4$)alkoxycarbonylamino, hydroxysulfonyl, aminocarbonylamino or mono-N—, di-N,N—, di-N,N'— or tri-N,N,N'—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar are optionally substituted on carbon with up to three fluoro; and said Ar$^1$ and Ar$^2$ moieties are independently optionally substituted on carbon or nitrogen with up to three substituents each independently selected from hydroxy, halo, carboxy, (C$_1$-C$_7$)alkoxy, (C$_1$-C$_4$)alkoxy(C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$)alkyl, (C$_3$-C$_7$)cycloalkyl(C$_1$-C$_4$)alkanoyl, formyl, (C$_1$-C$_8$)alkanoyl, (C$_1$-C$_6$)alkanoyl(C$_1$-C$_6$)alkyl, (C$_1$-C$_4$)alkanoylamino, (C$_1$-C$_4$)alkoxycarbonylamino, hydroxysulfonyl, aminocarbonylamino or mono-N—, di-N,N—, di-N,N'— or tri-N,N,N'—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar$^1$ and Ar$^2$ are optionally substituted on carbon with up to three fluoro;

A preferred method of the present invention is a method of the first embodiment wherein the selective EP$_4$ receptor agonist is a compound, designated Group A, of Formula Ia

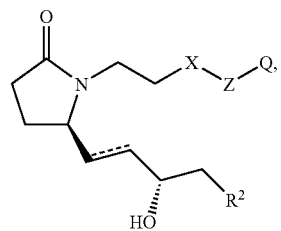

a prodrug thereof, a pharmaceutically acceptable salt of said compound or said prodrug, and stereoisomers and diastereomeric mixtures of said compound, prodrug or salt, wherein:

X is —CH$_2$—; Z is —(CH$_2$)$_3$—,

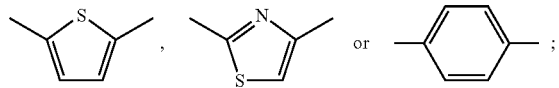

and R$^2$ is Ar wherein said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, (C$_1$-C$_7$)alkoxy, (C$_1$-C$_4$)alkoxy(C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$)alkyl, (C$_3$-C$_7$)cycloalkyl(C$_1$-C$_4$)alkanoyl, formyl, (C$_1$-C$_8$)alkanoyl, (C$_1$-C$_6$)alkanoyl(C$_1$-C$_6$)alkyl, (C$_1$-C$_4$)alkanoylamino, (C$_1$-C$_4$)alkoxycarbonylamino, hydroxysulfonyl, aminocarbonylamino or mono-N—, di-N,N—, di-N,N'— or tri-N,N,N'—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar$^1$ and Ar$^2$ are optionally substituted on carbon with up to three fluoro.

Another preferred method of the present invention is a method of the first embodiment wherein the selective EP$_4$ receptor agonist is a compound within Group A, designated Group B, a prodrug thereof, a pharmaceutically acceptable salt of said compound or said prodrug, and stereoisomers and diastereomeric mixtures of said compound, prodrug or salt, wherein Ar is cyclohexyl, 1,3-benzodioxolyl, thienyl, naphthyl or phenyl optionally substituted with one or two (C₁-C₄)alkyl, (C₁-C₄)alkoxy, (C₁-C₄)alkoxy(C₁-C₄)alkyl, chloro, fluoro, trifluoromethyl or cyano, wherein said alkyl and alkoxy substituents in the definition of Ar are optionally substituted with up to three fluoro.

Another preferred method of the present invention is a method of the first embodiment, wherein the selective EP₄ receptor agonist is a compound within Group B, designated Group C, a prodrug thereof, a pharmaceutically acceptable salt of said compound or said prodrug, and stereoisomers and diastereomeric mixtures of said compound, prodrug or salt, wherein -----is a single bond; Q is carboxy or (C₁-C₄)alkoxylcarbonyl; and Z is

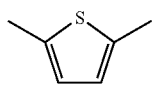

Another preferred method of the present invention is a method of the first embodiment, in which the selective EP₄ receptor agonist is a compound within Group C, designated Group D, a prodrug thereof, a pharmaceutically acceptable salt of said compound or said prodrug or a stereoisomer or diastereomeric mixture of said compound, prodrug or salt, wherein Q is carboxy and Ar is phenyl optionally substituted with one (C₁-C₄)alkyl, (C₁-C₄)alkoxy, (C₁-C₄)alkoxy(C₁-C₄)alkyl, chloro, fluoro, trifluoromethyl or cyano, wherein said alkyl and alkoxy substituents in the definition of Ar are optionally substituted with up to three fluoro.

Another preferred method of the present invention is a method of the first embodiment, in which the selective EP₄ receptor agonist is a compound within Group D, a prodrug thereof, a pharmaceutically acceptable salt of said compound or said prodrug or a stereoisomer or diastereomeric mixture of said compound, prodrug or salt, wherein Ar is 3-trifluoromethylphenyl.

Another preferred method of the present invention is a method of the first embodiment, in which the selective EP₄ receptor agonist is a compound within Group D, a prodrug thereof, a pharmaceutically acceptable salt of said compound or said prodrug or a stereoisomer or diastereomeric mixture of said compound, prodrug or salt, wherein Ar is 3-chlorophenyl.

Another preferred method of the present invention is a method of the first embodiment, in which the selective EP₄ receptor agonist is a compound within Group D, a prodrug thereof, a pharmaceutically acceptable salt of said compound or said prodrug or a stereoisomer or diastereomeric mixture of said compound, prodrug or salt, wherein Ar is 3-trifluoromethoxyphenyl.

A particularly preferred method of the present invention is a method of the first embodiment, in which the selective EP₄ receptor agonist is a compound selected from 5-(3-(2S-(3R-hydroxy-4-(3-trifluoromethyl-phenyl)-butyl)-5-oxo-pyrrolidin-1-yl)-propyl)-thiophene-2-carboxylic acid; 5-(3-(2S-(3R-hydroxy-4-(3-trifluoromethoxy-phenyl)-butyl)-5-oxo-pyrrolidin-1-yl)-propyl)-thiophene-2-carboxylic acid; or 5-(3-(2S-(4-(3-chloro-phenyl)-3R-hydroxy-butyl)-5-oxo-pyrrolidin-1-yl)-propyl)-thiophene-2-carboxylic acid.

Another method of the present invention is a method of the first embodiment, in which the selective EP₄ receptor agonist is a compound within Group A, a prodrug thereof, a pharmaceutically acceptable salt of said compound or said prodrug or a stereoisomer or diastereomeric mixture of said compound, prodrug or salt, wherein X is —CH₂—, Z is —(CH₂)₃—, Q is carboxyl or (C₁-C₄)alkoxycarbonyl and Ar is phenyl independently substituted with one to three cyano, (C₁-C₇)alkoxy substituted with one to three fluoro or (C₁-C₄)alkoxy(C₁-C₄)alkyl.

Another preferred method of the present invention is a method of the first embodiment in which the selective EP₄ receptor agonist is a compound within the group of compounds as described in the immediately preceding paragraph, a prodrug thereof, a pharmaceutically acceptable salt of said compound or said prodrug, and stereoisomers and diastereomeric mixtures of said compound, prodrug or salt, wherein -----is a single bond; Q is carboxy or (C₁-C₄)alkoxylcarbonyl; and Z is

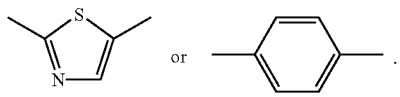

Yet another preferred embodiment of the present invention is a method of the first embodiment, in which the selective EP₄ receptor agonist is a compound within the group of compounds as described in the immediately preceding paragraph, a prodrug thereof, a pharmaceutically acceptable salt of said compound or said prodrug or a stereoisomer or diastereomeric mixture of said compound, prodrug or salt, wherein Q is carboxy and Ar is phenyl optionally substituted with one (C₁-C₄)alkyl, (C₁-C₄)alkoxy, (C₁-C₄)alkoxy(C₁-C₄)alkyl, chloro, fluoro, trifluoromethyl or cyano, wherein said alkyl and alkoxy substituents in the definition of Ar are optionally substituted with up to three fluoro.

Another preferred embodiment of the present invention is a method of the first embodiment in which the disorder is hypertension. Another preferred embodiment of the present invention is a method of the first embodiment in which the disorder is liver failure. Yet another embodiment of the present invention is a method of the first embodiment in which said disorder is loss of patency of the ductus arteriosus.

Another aspect of the present invention is directed to methods of treating hypertension, liver failure, loss of patency of the ductus arteriosus, glaucoma or ocular hypertension in a patient in need thereof, comprising administering to the patient a pharmaceutical composition; the pharmaceutical composition comprising a compound of Formula I or a prodrug thereof, or a pharmaceutically acceptable salt of the compound or prodrug, or a stereoisomer or diastereomeric mixture of the compound, prodrug or salt, and a pharmaceutically acceptable carrier, vehicle or diluent.

Another aspect of the present invention is directed to methods of treating hypertension with combinations of a compound of Formula I or a prodrug thereof, or a pharmaceutically acceptable salt of the compound or prodrug, or a stereoisomer or diastereomeric mixture of the compound, prodrug or salt; and an HMG-CoA reductase inhibitor (statin) or a prodrug thereof or a pharmaceutically acceptable salt of the HMG-CoA reductase inhibitor or prodrug.

Another aspect of the present invention is directed to methods of treating hypertension with combinations of a compound of Formula I or a prodrug thereof, or a pharmaceutically acceptable salt of the compound or prodrug, or a stereoisomer or diastereomeric mixture of the compound, prodrug or salt; and an antihypertensive agent or a prodrug thereof or a pharmaceutically acceptable salt of the antihypertensive agent or prodrug.

Another aspect of the present invention is a kit comprising:
a. an amount of a Formula I compound, a prodrug thereof or a pharmaceutically acceptable salt of said compound or said prodrug, or a stereoisomer or diastereomeric mixture of said compound, prodrug or salt and a pharmaceutically acceptable carrier or diluent in a first unit dosage form;
b. an amount of an antihypertensive agent, a prodrug thereof, or a pharmaceutically acceptable salt of said antihypertensive agent or prodrug, and a pharmaceutically acceptable carrier or diluent in a second unit dosage form; and
c. a container.

Yet another aspect of the present invention is a kit comprising:
a. an amount of a Formula I compound, a prodrug thereof or a pharmaceutically acceptable salt of said compound or said prodrug, or a stereoisomer or diastereomeric mixture of said compound, prodrug or salt and a pharmaceutically acceptable carrier or diluent in a first unit dosage form;
b. an amount of an HMG Co-A reductase inhibitor, a prodrug thereof, or a pharmaceutically acceptable salt of said HMG Co-A reductase inhibitor or prodrug, and a pharmaceutically acceptable carrier or diluent in a second unit dosage form; and
c. a container.

DETAILED DESCRIPTION OF THE INVENTION

The term "treating", "treat" or "treatment" is used herein includes preventative (e.g. prophylactic), palliative and curative treatment. The term "therapeutically effective amount", as used herein, means the amount of selective $EP_4$ receptor agonist that will elicit the desired therapeutic effect or provide the desired benefit when administered according to the desired treatment regimen. For example, a "therapeutically effective amount" of a compound of Formula I is an amount that will treat hypertension, liver failure, loss of patency of the ductus arteriosus, glaucoma or ocular hypertension in a patient in need thereof. The term "selective $EP_4$ receptor agonist" as used herein means a chemical substance of Formula I that can interact with the $EP_4$ receptor and initiate a physiological or pharmacological response characteristic of the $EP_4$ receptor and which has a greater affinity for the $EP_4$ receptor than for the $EP_1$, $EP_2$ and $EP_3$ receptors. A preferred group of selective $EP_4$ receptor agonists are those compounds of Formula I that can interact with the $EP_4$ receptor and initiate a physiological or pharmacological response characteristic of the $EP_4$ receptor and which have approximately a tenfold greater affinity for the $EP_4$ receptor than for the $EP_1$, $EP_2$ and $EP_3$ receptors. The term "loss of patency of the ductus arteriosus" as used herein means the partial or complete closure of the ductus arteriosus. The term "pharmaceutically acceptable" as used herein means that the carrier, vehicle, diluent, excipients, and/or salt must be compatible with the other ingredients of the formulation, and not deleterious to the recipient thereof. The term "prodrug" refers to compounds that are drug precursors which, following administration, release the drug in vivo by some chemical or physiological process (e.g. a prodrug on being brought to physiological pH or through enzyme action is converted to the desired drug form). Exemplary prodrugs upon cleavage release the corresponding drug compound.

The term "hydroxy" as used herein means the group —OH. The term "thiol" as used herein means the group —SH. The term "cyano" as used herein means the group —CN. The term "halo" as used herein means fluoro, chloro, bromo and iodo. The term "carboxy" as used herein means the group —$CO_2H$. The term "carbonyl" as used herein means the group —C(O)—. The term "formyl" as used herein means the group —C(O)H. The term "amino" means the group —$NH_2$, except when the amino group is mono or disubstituted, in which case one or both of the —$NH_2$ hydrogens is substituted as specified. The term "($C_1$-$C_7$)alkyl" as used herein means a straight or branched chain hydrocarbon group having from one to seven carbons. The term "($C_1$-$C_7$)alkyl" includes, but is not limited to, groups such as methyl, ethyl, propyl, isopropyl, butyl, isobutyl, sec-butyl, tert-butyl, pentyl, neopentyl, methylpentyl, hexyl, heptyl, methylhexyl and the like. Likewise, other alkyl terms such as "($C_1$-$C_4$)alkyl", "($C_1$-$C_6$)alkyl" and "($C_1$-$C_8$)alkyl" are straight or branched chain hydrocarbon groups with one to four, one to six, and one to eight carbons, respectively. The term "($C_2$-$C_7$)alkenyl" means a straight or branched chain hydrocarbon group having two to seven carbons and a carbon-carbon double bond. The term "($C_2$-$C_7$)alkenyl" includes, but is not limited to, groups such as vinyl, propenyl, allyl, 2-methylpropenyl, butenyl, etc. The term "($C_3$-$C_7$)cycloalkyl" as used herein means a cyclic hydrocarbon group having from three to seven carbons. The term "($C_3$-$C_7$)cycloalkyl" includes, but is not limited to, groups such as cyclopropyl, cyclobutyl, cyclopentyl, cyclohexyl, cycloheptyl, methylcyclopropyl, ethylcyclopropyl, methylcyclobutyl, etc. The terms "($C_1$-$C_7$)alkoxy" and "($C_1$-$C_4$)alkoxy", as used herein, mean the groups ($C_1$-$C_7$)alkyl-O— and ($C_1$-$C_4$)alkyl-O—, respectively. For example, the term "($C_1$-$C_4$)alkoxy" includes methoxy, ethoxy, propoxy, isopropoxy, butoxy, isobutoxy, sec-butoxy and tert-butoxy. The terms "($C_1$-$C_8$)alkanoyl", "($C_1$-$C_6$)alkanoyl", and "($C_1$-$C_4$)alkanoyl", as used herein, mean the groups ($C_1$-$C_8$)alkyl-C(O)—, ($C_1$-$C_6$)alkyl-C(O)—, and ($C_1$-$C_4$)alkyl-C(O)—, respectively. The term "($C_1$-$C_4$)alkanoylamino as used herein means the group ($C_1$-$C_4$)alkyl-C(O)NH—. The term "($C_1$-$C_4$)alkoxycarbonylamino" as used herein means the group ($C_1$-$C_4$)alkyl-O—C(O)—NH—. The term "hydroxysulfonyl" as used herein means the group —$SO_3H$. The term "aminocarbonylamino" as used herein means the group —NHC(O)$NH_2$. The terms "mono-N—, di-N,N—, di-N,N'—, or tri-N,N,N'—($C_1$-$C_4$)alkyl substituted aminocarbonylamino", as used herein, mean the groups —NHC(O)NH($C_1$-$C_4$)alkyl, —NHC(O)N(($C_1$-$C_4$)alkyl)$_2$, —N(($C_1$-$C_4$)alkyl)C(O)NH($C_1$-$C_4$)alkyl, or —N(($C_1$-$C_4$)alkyl)C(O)NH(($C_1$-$C_4$)alkyl)$_2$, respectively. The term "sulfonamido" as used herein means the group —S(O)$_2$$NH_2$. The terms mono-N— or di-N,N—($C_1$-$C_4$)alkylamino as used herein mean the groups —NH($C_1$-$C_4$)alkyl or —N(($C_1$-$C_4$)alkyl)$_2$, respectively. The term "carbamoyl" as used herein means the group —OC(O)$NH_2$. The terms "mono-N— or di-N,N—($C_1$-$C_4$) alkylcarbamoyl" mean the groups —OC(O)NH($C_1$-$C_4$)alkyl or —OC(O)N(($C_1$-$C_4$)alkyl)$_2$, respectively. The term "($C_1$-$C_6$)alkylthio" as used herein means the group ($C_1$-$C_6$)alkyl-S—. The term "($C_1$-$C_6$)alkylsulfinyl" as used herein means the group ($C_1$-$C_6$)alkyl-S(O)—. The term "($C_1$-$C_4$)alkylsulfonyl" as used herein means the group ($C_1$-$C_4$)alkyl-S(O)$_2$—. The terms "mono-N— or di-N,N—($C_1$-$C_4$)alkylaminosulfinyl" as used herein mean the groups —S(O)NH($C_1$-$C_4$)alkyl or —S(O)N(($C_1$-$C_4$)alkyl)$_2$, respectively.

The term "pharmaceutically acceptable salt" as used herein refers to both nontoxic anionic salts and cationic salts. Anionic salts include, but are not limited to, chloride, bromide, iodide, sulfate, bisulfate, phosphate, acetate, maleate, fumarate, oxalate, lactate, tartrate, citrate, gluconate, methanesulfonate and 4-toluene sulfonate. Cationic salts include, but are not limited to, sodium, potassium, calcium, magnesium, ammonium, protonated benzathine (N,N'-dibenzylethylenediamine), choline, ethanolamine, diethanolamine, ethylenediamine, meglamine (N-methyl glucamine), benethamine (N-benzylphenethylamine), piperazine or tromethamine (2-amino-2-hydroxymethyl-1,3-propanediol.

The chemist of ordinary skill in the art will also recognize that certain compounds of Formula I of this invention can exist in tautomeric form, i.e., that a rapid equilibrium exists between two isomers. A common example of tautomerism is keto-enol tautomerism, i.e.,

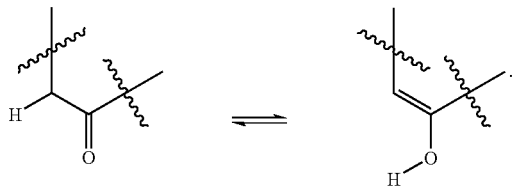

Examples of compounds that can exist as tautomers include hydroxypyridines, hydroxypyrimidines and hydroxyquinolines. Other examples of compounds that can exist as tautomers will be recognized by those skilled in the art. All such tautomers and mixtures thereof are included in this invention.

The methods of the present invention also includes the use of isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of Formula I include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Methods of treatment with compounds of Formula I, prodrugs thereof, and pharmaceutically acceptable salts of said compounds and said prodrugs, and stereoisomers and diastereomeric mixtures of said compounds, prodrugs and salts, which contain the aforementioned isotopes and/or other isotopes of other atoms are within the scope of this invention. Certain isotopically-labeled compounds of Formula I, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I and prodrugs thereof can generally be prepared by carrying out the procedures disclosed in the Schemes and/or as described for the Compounds and Preparations below, by substituting a readily available isotopically labeled reagent for a non-isotopically labeled reagent.

The compounds of Formula I used in the methods of this invention have asymmetric carbon atoms, and therefore, are enantiomers or diastereomers. Diasteromeric mixtures can be separated into their individual diastereomers on the basis of their physical chemical differences by methods known per se, for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Enantiomers and diastereomers of the compounds of Formula I can also be prepared by utilizing suitable enantiomerically enriched starting materials, or by asymmetric or diastereoselective reactions to introduce asymmetric carbon atoms with the correct stereochemistry. All such isomers, including diastereomers, enantiomers and mixtures thereof are considered as compounds of Formula I and can be used in the methods of this invention. Some of the compounds of Formula I are acidic, and therefore, can form a salt with a pharmaceutically acceptable cation. All such salts are within the scope of the compounds of Formula I and can be prepared by conventional methods. For example, the salt can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

The present invention is directed to the treatment of disorders responsive to modulation of the $EP_4$ receptor by administering to a patient in need thereof a therapeutically effective amount of a compound of Formula I. More specifically, the present invention is directed to the treatment of hypertension, liver failure, loss of patency of ductus arteriosus, glaucoma or ocular hypertension by administration of a selective $EP_4$ receptor agonist of Formula I. The compounds of Formula I, which are useful in the methods of the present invention, are prepared as described in U.S. patent application Ser. No. 09/990,556, which was filed on Nov. 21, 2001. In general, the compounds of Formula I are made by processes that are analogous to those known in the chemical arts. These processes include methods that may require protection of remote functionality (e.g., primary amine, secondary amine, secondary alcohol, primary alcohol, carboxyl in Formula I precursors). The need for such protection will vary depending upon the nature of the remote functionality and the conditions of the preparation methods. The need for such protection is readily determined by one skilled in the art. The use of such protection/deprotection methods is also within the skill in the art. The term "protecting group," where used herein, refers to a radical that may be attached to a functional group on a substrate. The "protecting group" is such that it is easily attached and easily removed without affecting other functional groups of the substrate and it prevents the protected functional group from being removed, altered or otherwise destroyed. For a general description of protecting groups and their use, see Greene, T. W.; Wuts, P. G. M., Protective Groups in Organic Synthesis, $2^{nd}$ ed.; John Wiley and Sons Inc.: New York, 1991. The starting materials and reagents used for the synthesis of compounds of Formula I are also readily available or can be easily synthesized by those skilled in the art using conventional methods of organic synthesis in light of this disclosure.

In general, compounds of Formula I are prepared by protection of the hydroxyl group of either racemic or (R)-hydroxymethyl-2-pyrrolidinone, followed by alkylation of the amide nitrogen with an alkyl halide that contains a suitably protected acid precursor or isostere (Scheme A). The term "isostere," where used herein, refers to a functional group that, when used in place of another functional group, approximates the reactivity of the functional group that it replaces. In some cases, the alkyl halide must be further elaborated to install the suitably protected acid precursor or isostere (Scheme B1). The hydroxyl protecting group is removed, the alcohol oxidized to the aldehyde which is then reacted with the anion of a suitable keto-phosphonate (Scheme C). The resulting enone of Formula 8 of Scheme E is then subjected to reduction of both the double bond and ketone to give the desired saturated alcohols of Formula 9 of Scheme E. If desired, a diastereoselective reduction of the enone can be effected to give, for example, predominantly the 15-(R) isomer or the 15-(S) isomer. The carboxylic ester or precursor to an acid isostere (e.g., nitrile) is then converted into the appropriate acidic group (carboxylic acid, tetrazole, etc).

A preferred method for converting a nitrile into the desired tetrazole is treatment of the nitrile with dibutyltin oxide and trimethylsilylazide, in refluxing toluene (S. J. Wittenberger and B. G. Donner, J. Org. Chem. 1993, 58, 4139-4141). For a review of alternative preparations of tetrazoles see R. N. Butler, Tetrazoles, in Comprehensive Heterocyclic Chemistry; Potts, K. T. Ed.; Pergamon Press: Oxford, 1984, Vol. 5, pp 791-838.

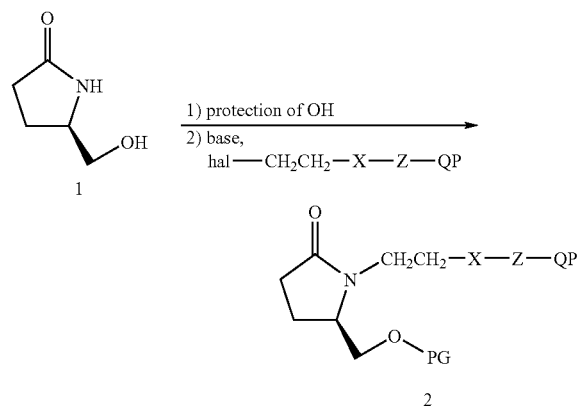

More specifically, compounds of Formula I are prepared by the following procedures. In the first general sequence, which begins with Scheme A, the hydroxyl group of 5-(R)-hydroxymethyl-2-pyrrolidinone (Aldrich Chemical, or prepared as described by Bruckner et al., Acta. Chim. Hung. Tomus, 1959, 21, 106) is suitably protected (where PG is a suitable protecting group) by reaction of a compound of Formula 1 in a reaction inert solvent. As used herein, the expressions "reaction inert solvent" and "inert solvent" refer to a solvent or mixture of solvents that does not interact with starting materials, reagents, intermediates or products in a manner that adversely affects the yield of the desired product. In some cases herein, a list of preferred reaction inert solvents, is described. However, any solvent that meets the above definition of reaction inert solvent for a particular reaction may be used in that reaction. All reactions are carried out in a reaction inert solvent unless specifically stated otherwise. Any standard alcohol protecting group may be utilized, including tetrahydropyranyl, trimethylsilyl, tert-butyl-dimethylsilyl, or benzyl. A preferred protecting group is tert-butyl-dimethylsilyl (TBS), which can be installed by standard methods as described in Greene, T. W.; Wuts, P. G. M., Protective Groups in Organic Synthesis, $2^{nd}$ ed.; John Wiley and Sons Inc.: New York, 1991. It is preferable to treat 5-(R)-hydroxymethyl-2-pyrrolidinone in methylene chloride at 0° C. with 0.1 equivalents (eq.) of 4-dimethylaminopyridine, 1.1 eq. of tert-butyl-dimethylsilylchloride, and 2 eq. of imidazole (see, e.g., Tetrahedron Asymmetry 1996, 7, 2113). The amide nitrogen is alkylated with one of a variety of alkylating agents (hal-$CH_2CH_2$—X-Z-QP, where hal is a leaving group such as bromide or iodide, X and Z are as described in the Summary, and QP is a nitrile, carboxylic acid ester or other precursor to a carboxylic acid or acid isostere) to introduce the desired side chain. The amide nitrogen is first deprotonated with a suitable base. Preferred bases include sodium hexamethyldisilazide (also referred to herein as NaHMDS or NaN(SiMe$_3$)$_2$) or sodium hydride in a reaction inert solvent such as N,N-dimethylformamide (DMF), tetrahydrofuran (THF), 1,2-dimethoxyethane or 1,4-dioxane. A preferred solvent is DMF. The appropriate temperature range for anion formation is between −78° C. and the temperature at which the solvent refluxes. A preferred temperature for this reaction is about 0° C. After formation of the anion, the alkylating agent (hal-$CH_2CH_2$—X-Z-QP) is added and the solution is stirred at an appropriate temperature. The appropriate temperature range for alkylation is between −20° C. and the temperature at which the solvent refluxes. The preferred temperature range for this reaction is between 0° C. and 100° C. Typical alkylating agents are primary, secondary, benzylic, propargyllic halides and primary, secondary, benzylic or propargyllic sulfonates. Preferred alkylating agents are alkyl bromides or alkyl iodides.

Many of the useful alkylating agents of the formula hal-$CH_2CH_2$—X-Z-QP are commercially available. For example, ethyl-7-bromoheptanoate and 7-bromoheptanonitrile may be obtained from Aldrich Chemical, Milwaukee, Wis. Numerous methods known to those skilled in the art exist for the synthesis of those and other desired alkylating agents used in the above Scheme (see, e.g., "The Chemistry of the Carbon-Halogen Bond," Ed. S. Patai, J. Wiley, New York, 1973 and/or "The Chemistry of Halides, Pseudo-Halides, and Azides," Eds. S. Patai and Z. Rappaport, J. Wiley, New York, 1983).

Alkyl halides are also prepared by halogenation of an alcohol or an alcohol derivative. Alkyl chlorides are typically prepared from the alcohols with reagents such as hydrogen chloride, thionyl chloride, phosphorous pentachloride, phosphorous oxychloride or triphenylphosphine/carbon tetrachloride in a reaction inert solvent. For the preparation of alkyl bromides the alcohol is commonly treated with reagents such as hydrogen bromide, phosphorous tribromide, triphenylphosphine/bromine or carbonyldiimidazole/allyl bromide in a reaction inert solvent. To prepare alkyl iodides, the alcohol is typically reacted with reagents such as triphenylphosphine/iodine/imidazole or hydrogen iodide in a reaction inert solvent. Alkyl chlorides are converted to the more reactive alkyl bromides or alkyl iodides by treatment with an inorganic salt such as sodium bromide, lithium bromide, sodium iodide or potassium iodide in a reaction inert solvent such as acetone or methyl ethyl ketone. Alkyl sulfonates are also used as electrophiles or are converted to alkyl halides. Sulfonates are prepared from the alcohol using a mild base such as triethylamine or pyridine and a sulfonyl chloride in a reaction inert solvent such a methylene chloride or diethyl ether. Conversion to the halide is accomplished by treatment of the alkyl sulfonate with an inorganic halide (sodium iodide, sodium bromide, potassium iodide, potassium bromide, lithium chloride, lithium bromide, etc) or a tetrabutylammonium halide in a reaction inert solvent.

Alkyl halides of the formula hal-$CH_2CH_2$—X-Z-QP where X is $CH_2$ and Z is phenyl, thienyl or thiazolyl are also prepared as shown in Scheme B1. For example, propargyl alcohol is treated with a compound of formula 14 of Scheme B1 containing the suitably protected acid isostere (hal-Z-QP), where the "hal-Z" group is an aryl bromide, iodide or triflate, in the presence of copper (I) iodide; a palladium catalyst such as palladium chloride, bis(triphenylphosphine)palladium dichloride or tetrakis(triphenylphosphine)palladium(0); and an amine such as triethylamine, diisopropylamine or butylamine in a reaction inert solvent, preferably an aprotic solvent such as acetonitrile, at a temperature of about 0° C. to about 100° C. For additional references, see Tetrahedron 1984, 40, 1433 and Org. Lett. 2000, 2(12), 1729. The resulting alkynes are then converted to the corresponding alkanes via hydrogenation in the presence of a palladium or platinum catalyst in a reaction inert solvent such as methanol, ethanol and/or ethyl acetate at a temperature of about 0° C. to about 50° C. The alcohol portion of the molecule is replaced with a suitable leaving group such as bromide or iodide. For the preparation of alkyl bromides, the alcohol is commonly treated with reagents such as hydrogen bromide, phosphorous tribromide, triphenylphosphine/bromine or carbonyldiimidazole/allyl bromide. The use of carbonyldiimidazole/allyl bromide is preferred. To prepare alkyl iodides, the alcohol is typically reacted with a reagent such as triphenylphosphine/iodine/imidazole or hydrogen iodide in a reaction inert solvent. Alkyl chlorides are converted to the more reactive alkyl bromides or alkyl iodides by treatment with an inorganic salt such as sodium bromide, lithium bromide, sodium iodide or potassium iodide in a reaction inert solvent such as acetone or methyl ethyl ketone. Alkyl sulfonates can be used as electrophiles or are converted to alkyl halides. Alkyl sulfonates are prepared from the corresponding alcohol using a mild base such as triethylamine or pyridine and a sulfonyl chloride in a reaction inert solvent such as methylene chloride or diethyl ether. Conversion to the halide is accomplished by treating the alkyl sulfonate with an inorganic halide such as, for example, sodium iodide, sodium bromide, potassium iodide, potassium bromide, lithium chloride or lithium bromide in a reaction inert solvent. Conversion to the halide may also be accomplished by treating the alkyl sulfonate with an organic ammonium halide such as tetrabutylammonium halide in a reaction inert solvent. Alkyl chlorides are typically prepared from the alcohols with reagents such as hydrogen chloride, thionyl chloride, phosphorous pentachloride, phosphorous oxychloride, or triphenylphosphine/carbon tetrachloride.

Scheme B1

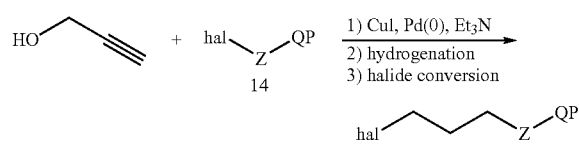

In some cases, as shown in Scheme B2, it is preferred to first alkylate with propargyl bromide or iodide, and then further elaborate to introduce the suitably protected acid precursor or isostere. For example, where the alkylating agent is propargyl bromide or iodide, compounds of Formula 3 of Scheme B2 are treated with compounds of Formula 14 of Scheme B2 containing the suitably protected acid precursor or isostere (hal-Z-QP), where the "hal-Z" group is an aryl bromide, iodide or triflate, in the presence of copper (I) iodide; a palladium catalyst such as palladium chloride, bis(triphenylphosphine)palladium dichloride or tetrakis(triphenylphosphine)palladium(0); and an amine such as triethylamine, diisopropylamine or butylamine in a reaction inert solvent, preferably an aprotic solvent such as acetonitrile, at a temperature of about 0° C. to about 100° C. For additional references see Tetrahedron 1984, 40, 1433 and Org. Lett. 2000, 2(12), 1729. The resulting alkynes are then converted to the corresponding alkanes via hydrogenation in the presence of a palladium or platinum catalyst in a reaction inert solvent such as methanol, ethanol and/or ethyl acetate at a temperature of about 0° C. to about 50° C.

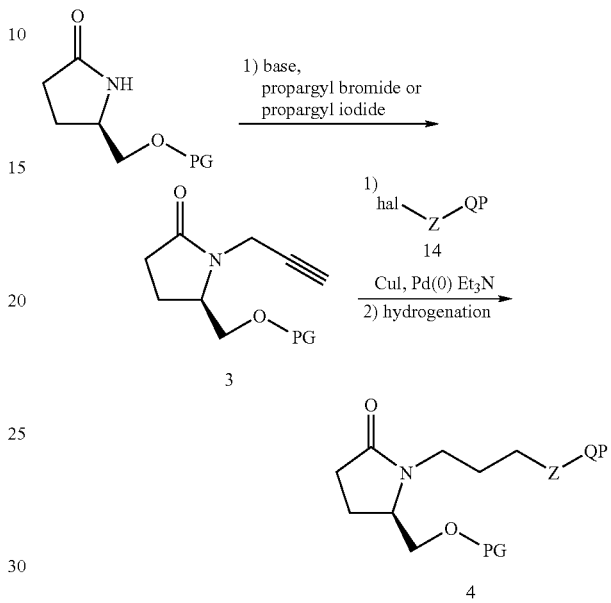

Halo-arylesters and halo-aryinitriles of Formula 14 of Scheme B2 are prepared by methods known to those skilled in the art. For example, 2-bromo-4-(ethoxycarbonyl)thiazole is prepared according to the procedure described in J. Org. Chem. 1996, 61(14), 4623; and 2-bromo-5-(ethoxycarbonyl)thiazole is prepared according to the procedure described in Helv. Chim. Acta 1942, 25, 1073. Other halo-arylesters and halo-arylnitriles of Formula 14 of Scheme B2, which are useful in the procedures of this invention, such as, inter alia, ethyl-4-bromobenzoate and 4-bromobenzonitrile are commercially available. Ethyl-2-bromo-thiophene-5-carboxylate is prepared by esterification of commercially available 2-bromo-thiophene-5-carboxylic acid.

The alcohol protecting groups of compounds of Formula 2 of Scheme A or Formula 4 of Scheme B2 are then removed. For a general description of methods for deprotection of protected alcohols, see Greene, T. W.; Wuts, P. G. M., Protective Groups in Organic Synthesis, $2^{nd}$ ed.; John Wiley and Sons Inc.: New York, 1991. Removal of the tert-butyl-dimethylsilyl group in compounds of Formula 2 and Formula 4 of Scheme B2 is preferably accomplished by treating the compound with tetrabutylammonium fluoride or trifluoroacetic acid in a reaction inert solvent, preferably in a suitable aprotic solvent at a temperature of about of –30° C. to about ambient temperature. Where used herein, the term "ambient temperature" refers to the temperature of the immediate, unaltered surroundings of the reaction mixture. Ambient temperature is generally between 20° C. and 25° C. An especially preferred solvent is methylene chloride. A preferred temperature range is between 0° C. to ambient temperature. Another preferred method to remove the TBS group is by treatment of the silyl ether with an aqueous solution of a mineral acid in a protic solvent. In this case, it is preferred that the silyl ether is treated with a 1N aqueous solution of hydrochloric acid in methanol at ambient temperature. Subsequent to deprotection, the alcohols are oxidized to the aldehyde by use of a modification of the Pfitzner Moffatt oxidation [K. E. Pfitzner and M. E. Moffatt, J. Am. Chem. Soc. 1965, 87, 5661] which minimizes racemization by avoiding contact with water. For example, oxidation of the alcohol to the aldehyde is achieved by stirring the alcohol in a reaction inert solvent, preferably a hydrocarbon solvent such as toluene, xylene or, preferably, benzene, with dimethyl sulfoxide, a weak acid such as acetic acid or, preferably, pyridinium trifluoroacetate, and a diimide such as diethyl carbodiimide or, preferably, dimethylaminopropylethylcarbodiimide or, if desired, dimethylaminopropylethylcarbodiimide hydrochloride, at temperatures of about 0° C. to about ambient temperature for about one to about four hours. Alternate methods to achieve oxidation while minimizing racemization of the asymmetric center adjacent to the resulting aldehyde are discussed in detail in Tetrahedron Letters 2000, 41, 1359, and include the usual Pfitzner-Moffatt reaction, oxidation with chromium trioxide-pyridine complex [J. Org. Chem. 1970, 35, 4000], oxidation with Dess-Martin reagent [J. Org. Chem. 1983, 48, 4155] or oxidation with TEMPO-bleach [Tetrahedron Letters 1992, 33, 5029].

The resulting aldehyde is preferably subjected without purification to a Horner-Wittig reaction with the sodium or lithium salt of a phosphonate of Formula 7 of Scheme C (R is lower alkyl, haloalkyl or aryl). The sodium or lithium salts are pre-formed by prior treatment of the phosphonates with a suitable base such as sodium hydride or $NaN(SiMe_3)_2$ in a suitable reaction inert solvent, preferably an aprotic ethereal solvent at a temperature of about 0° C. to about 50° C. A preferred solvent is THF and a preferred temperature is ambient temperature. A solution of the aldehyde is then added to the salt of the phosphonate in a reaction inert solvent, preferably an aprotic solvent at a temperature of about 0° C. to about 50° C. to give enones of Formula 8 of Scheme C. A preferred solvent is THF and a preferred temperature is ambient temperature.

Pat. No. 4,177,346; Tetrahedron Lett. 1989, 30(36), 4787-4790; and Angew. Chem. 1996, 108(3), 366-369. In general, as shown in Scheme C1, the phosphonates of Formula 7 are prepared from reaction of the appropriately substituted arylacetic acid esters or the methoxymethyl amide of the arylacetic acid with the lithium reagent derived from a dialkyl methylphosphonate. These methods are also applicable to cycloalkylacetic esters and methoxymethylamides such as ethyl-cyclohexylacetate and ethyl-cyclopentylacetate. The aryl- and cycloalkyl-acetic acid esters are prepared by esterification of the corresponding acetic acid by methods known to those skilled in the art. The methoxymethylamides are prepared by a standard amide bond forming reaction between the corresponding acetic acid and methoxymethyl amine. Preferably, the coupling of the amine with the carboxylic acid is carried out in a reaction inert solvent such as dichloromethane or DMF by a coupling reagent such as 1-(3-dimethylaminopropyl-3-ethylcarbodiimide hydrochloride (EDC) or 1,3-dicyclohexylcarbodiimide (DCC) in the presence of an acid activating agent such as 1-hydroxybenzotriazole hydrate (HOBT) to generate the methoxymethyl amide. In the case where the amine is present as the hydrochloride salt, it is preferable to add one equivalent of a suitable base such as triethylamine to the reaction mixture. Alternatively, coupling of the amine with the carboxylic acid is effected with a coupling reagent such as benzotriazol-1-yloxy-tris(dimethylamino)-phosphonium hexafluorophosphate (BOP) in a reaction inert solvent such as methanol. Such coupling reactions are generally conducted at temperatures of about −30° C. to about 80° C., preferably about 0° C. to about 25° C. For a discussion of other conditions used for amide couplings, see HeubenWeyl, Vol. XV, part 11, E. Wunsch, Ed., George Theime Verlag, 1974, Stuttgart.

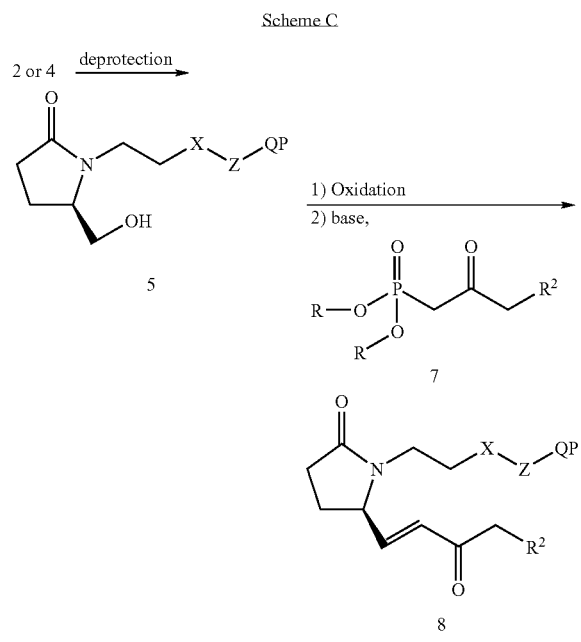

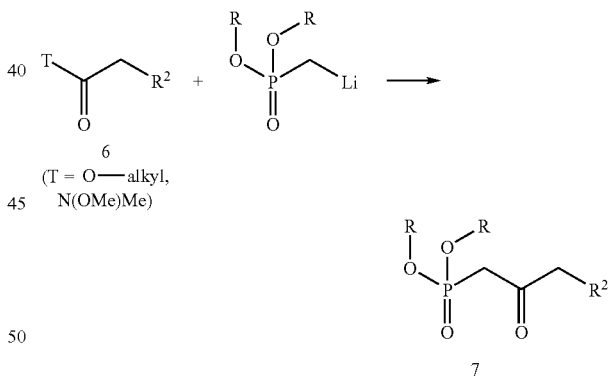

Methods for the preparation of phosphonates of Formula 7 of Scheme C1 can be found in U.S. Pat. No. 3,932,389; U.S.

The requisite arylacetic acids and esters of Formula 6 of Scheme C1 are commercially available or are prepared by methods well known to those skilled in the art. As shown in Scheme C2, many aryl and heteroaryl substituted aryl acetic acids are prepared by Suzuki couplings of the appropriate arylboronic acids or arylboronate esters with the desired aryl halides (for a review of the Suzuki coupling reaction see A. R. Martin and Y. Yang in Acta Chem. Scand. 1993, 47, 221 or J. Am. Chem. Soc. 2000, 122(17), 4020). For example, the 3-pinacolboronate ester of ethyl-3-bromophenylacetate is prepared using the method described by Masuda et al. in J. Org. Chem. 2000, 65, 164. The 3-pinacolboronate ester of ethyl-3-bromophenylacetate is then coupled with the desired aryl halide to give the desired 3-aryl-phenylacetic acid (see Synlett. 2000, 6, 829). Hydroxy substituted aryl acetic esters are alkylated with alkyl halides and benzylic halides by methods well known to those skilled in the art.

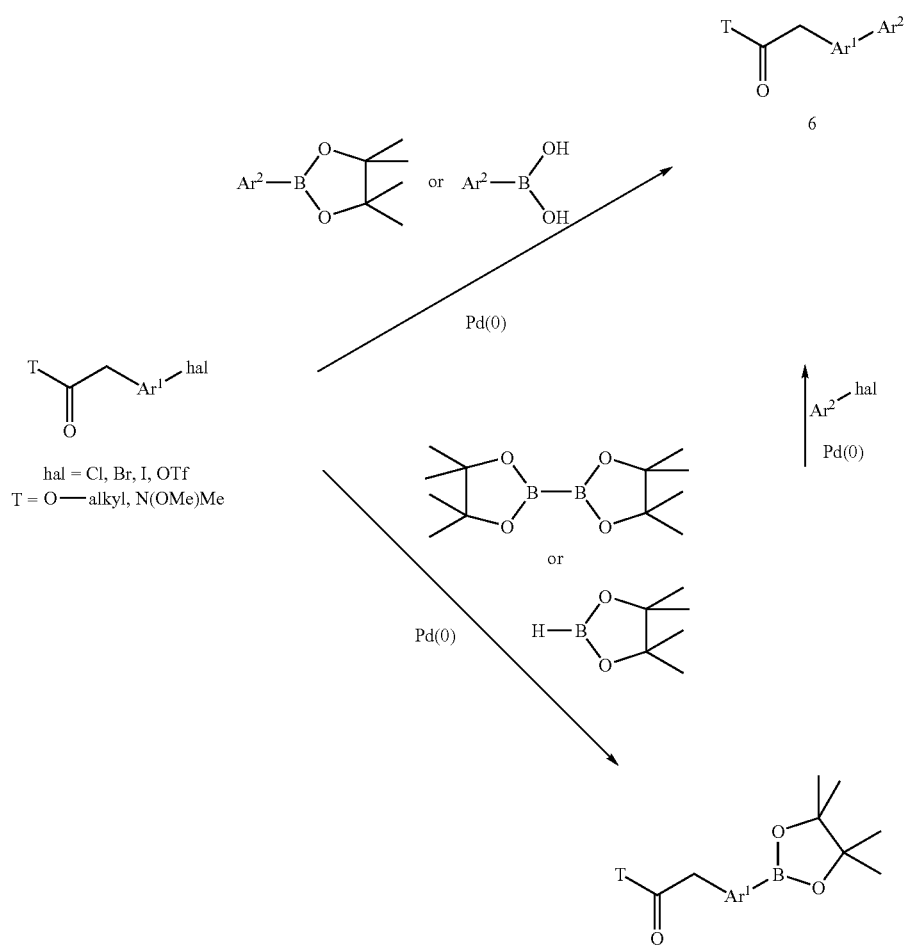

For a review of the preparation of diaryl ethers, see Angew. Chem. Int. Ed. 1999, 38(16), 2345. Aryl acetic acids substituted with an alkylether linkage are prepared using Mitsunobu conditions (for a review see Synthesis 1981, 1). Typically, the coupling between a phenolic component and a benzylic alcohol is achieved by addition of triphenylphosphine and diethyl azodicarboxylate or diisopropyl azodicarboxylate in a reaction inert solvent such as methylene chloride or THF.

Alternatively, phosphonates of Formula 7 of Scheme D are prepared as shown in Scheme D. In general, triethylphosphite is added slowly to epibromo- or epichloro-hydrin (10) at a temperature of about 135° C. As the triethylphosphite is added, the temperature drops to about 105° C. The reaction mixture is refluxed overnight and the product, a compound of Formula 11, is isolated by vacuum distillation (see Phosphorus, Sulfur Silicon Relat. Elem. 1992, 165, 71, or U.S. Pat. No. 2,627,521). The required Grignard solutions are prepared from the appropriate aryl halides according to procedures well known to those skilled in the art in a reaction inert solvent, preferably an ethereal solvent such as THF, and cooled to approximately −30° C. Catalytic copper (I) iodide is added followed by addition of the epoxide of Formula 11 [Phosphorus, Sulfur Silicon Relat. Elem. 1995, 105, 45]. The requisite aryl halides (e.g., 3-bromo-biphenyl) are commercially available or are prepared by methods well known to those skilled in the art.

The resulting alcohols are then oxidized, preferably using a Swern oxidation [Synthesis 1981,165-185] or Dess-Martin reagent [J. Org. Chem. 1983, 48, 4155]. Alternative oxidation procedures such as Pfitzner-Moffatt reaction, chromium trioxide-pyridine complex [R. Ratcliffe, et al., J. Org. Chem. 1970, 35, 4000], TEMPO-bleach [Tet. Lett. 1992, 33, 5029], Jones oxidation, Manganese dioxide, pyridiniumchlorochromate or pyridinium dichromate may also be utilized to prepare keto-phosphonates of Formula 7 of Scheme D.

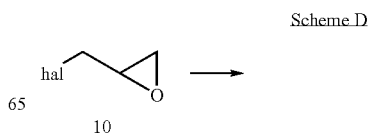

Scheme D

-continued

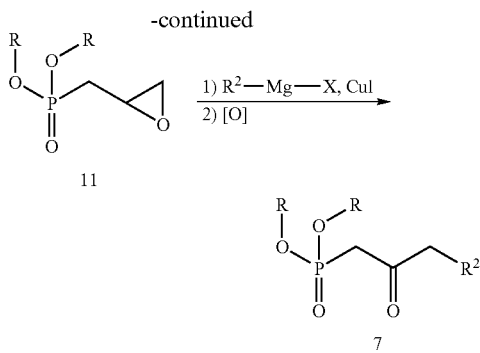

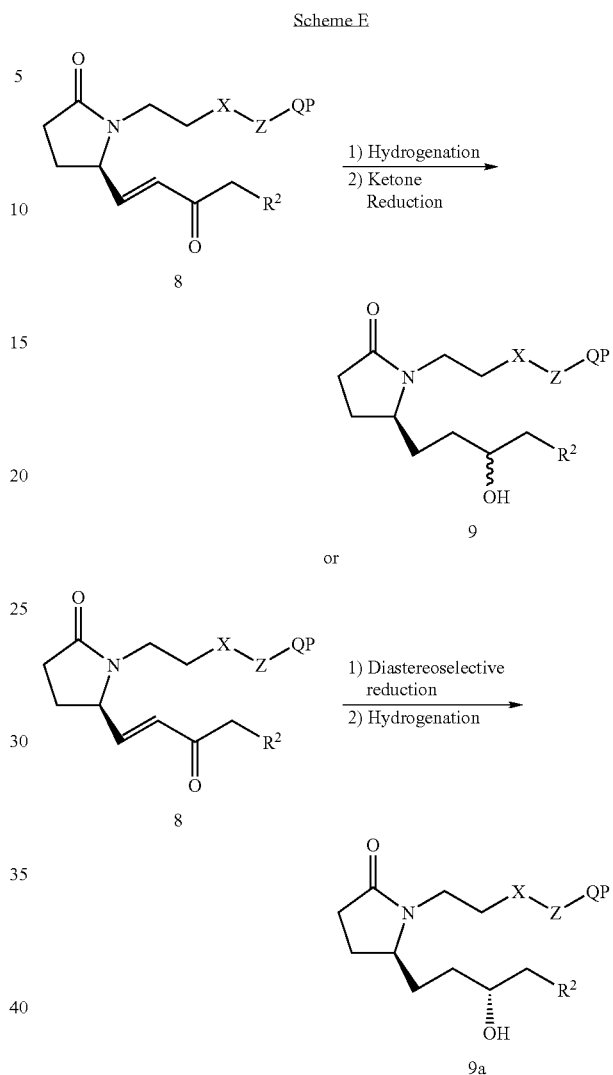

Scheme E

An enone of Formula 8 of Scheme E (which may also be prepared as shown in Scheme C) is reduced to a mixture of alcohol diastereomers of Formula 9 of Scheme E by methods well known to those skilled in the art. In general, the double bond of the enone is first reduced by catalytic hydrogenation. It is preferred that the double bond is reduced by hydrogenation over a noble metal catalyst such as palladium on carbon or platinum oxide in a reaction inert solvent such as ethyl acetate, methanol or ethanol at a temperature of ambient temperature up to about the reflux temperature of the solvent being used under 1 to 4 atmospheres of hydrogen. The resulting ketone is then treated with a reducing agent, preferably sodium borohydride, in a protic solvent, preferably ethanol or methanol, to give alcohols of Formula 9 of Scheme E. Other selective reducing agents well known to those skilled in the art that will reduce the ketone but no other functional groups, such as zinc borohydride or lithium triethylborohydride may also be employed. The temperature selection will be based upon the activity of the reducing agent and will preferably be between about 0° C. to ambient temperature. If desired, the mixture of alcohols of Formula 9 may be separated by preparative chromatography or HPLC to give the desired 15-(R) diastereomer.

In the second sequence shown in Scheme E, an enone of Formula 8 is first treated with a hydride reducing agent in the presence of a chiral catalyst. Where used herein, the term "hydride reducing agent" refers to a compound that is able to reduce a compound having a higher oxidation state by transferring hydrogen to the higher oxidation state compound. A preferred hydride reducing agent is catecholborane. A preferred chiral catalyst for performing such reactions enantioselectively is (R)-2-methyl-CBS-oxazaborolidine reagent (Aldrich Chemical Co., Milwaukee, Wis.) (see the method described in Eur. J. Org. Chem. 1999, 2655). The reduction is carried out in a reaction inert solvent, preferably an aprotic solvent such as methylene chloride, at a temperature of about −100° C. to ambient temperature. A preferred temperature for this reaction is about −40° C. Alternative methods and catalysts which are utilized to effect stereoselective reduction of the enone carbonyl are described in J. Am. Chem. Soc. 1995, 117, 2675; J. Am. Chem. Soc. 1979, 101, 5843; Tett. Lett. 1990, 31, 611; U.S. Pat. No. 6,037,505; and Angew. Chem. Int. Ed. 1998, 37, 1986. The double bond of the allylic alcohol is then reduced to provide the compound of Formula 9a. It is preferred that the double bond is reduced by hydrogenation over a noble metal catalyst such as palladium on carbon or platinum oxide in a reaction inert solvent such as ethyl acetate, methanol or ethanol at ambient temperature to the reflux temperature of the solvent being used under 1 to 4 atmospheres of hydrogen.

A procedure for the preparation of compounds of formula 9b is shown in Scheme F. In general, tetrahydro-pyrrolizine-3,5-dione (the compound of formula 12 of Scheme F) is prepared as described in U.S. Pat. No. 4,663,464 or J. Med. Chem. 1987, 30(3); 498-503. The compound of Formula 12 of Scheme F is then dissolved in a reaction inert solvent, preferably an aprotic solvent at a suitable temperature. It is preferred that said compound is dissolved in methylene chloride at about 0° C. The reaction mixture is then treated with the appropriate Grignard reagent (for additional references on addition of Grignard reagents to Formula 12 of Scheme F, see Syn. Comm. 1988, 18(1), 37-44; Helv. Chim. Acta 1987, 70, 2003-2010). The reaction may be warmed to ambient temperature to effect complete reaction. The resulting ketone is then treated with a reducing agent, preferably sodium borohydride in a protic solvent, preferable ethanol or methanol. Other selective reducing reagents which will reduce the ketone but no other functional groups, e.g., zinc borohydride or lithium triethylborohydride, can also be employed. The temperature selection will be based upon the activity of the reducing agent, preferably from about 0° C. to ambient temperature. The resulting hydroxyl group is then suitably protected. Standard alcohol protecting groups such as tetrahydropyranyl, trimethylsilyl, tert-butyl-dimethylsilyl or benzyl may be utilized. A preferred protecting group is tert-butyl-dimethylsilyl which is installed by standard methods as described in Greene, T. W.; Wuts, P. G. M., Protective Groups in Organic Synthesis, 2$^{nd}$ ed.; John Wiley and Sons Inc.: New York, 1991. Preferred conditions for this reaction include treating the alcohol in DMF at ambient temperature with 0.1 eq. of 4-dimethylaminopyridine, 1.1 eq. of tert-butyl-dimethylsilylchloride and 2 eq. of imidazole.

The resulting compound of Formula 13 of Scheme F is then alkylated on nitrogen with one of a variety of alkylating agents of the formula hal-CH$_2$CH$_2$—X-QP to introduce the desired side chain. The amide nitrogen is first deprotonated with a suitable base in a reaction inert solvent. Preferred bases for this reaction include NaN(SiMe$_3$)$_2$ or sodium hydride in a solvent such as DMF, tetrahydrofuran, dimethoxyethane or dioxane. An especially preferred solvent is DMF. The appropriate temperature range for anion formation is between –78° C. and about the temperature at which the solvent refluxes. It is preferred that the reaction is conducted at ambient temperature. After formation of the anion, the alkylating agent of the formula hal-CH$_2$CH$_2$—X-QP is added, and the solution is stirred at a temperature between –20° C. to about the temperature at which the solvent refluxes. A preferred temperature is between ambient temperature and 100° C. Typical alkylating agents include primary halides and primary sulfonates. Preferably, an alkyl bromide or alkyl iodide is used. The alcohol protecting group is then removed by methods well known to those skilled in the art (see Greene, T. W.; Wuts, P. G. M., Protective Groups in Organic Synthesis, 2$^{nd}$ ed.; John Wiley and Sons Inc.: New York, 1991) to produce compounds of Formula 9b.

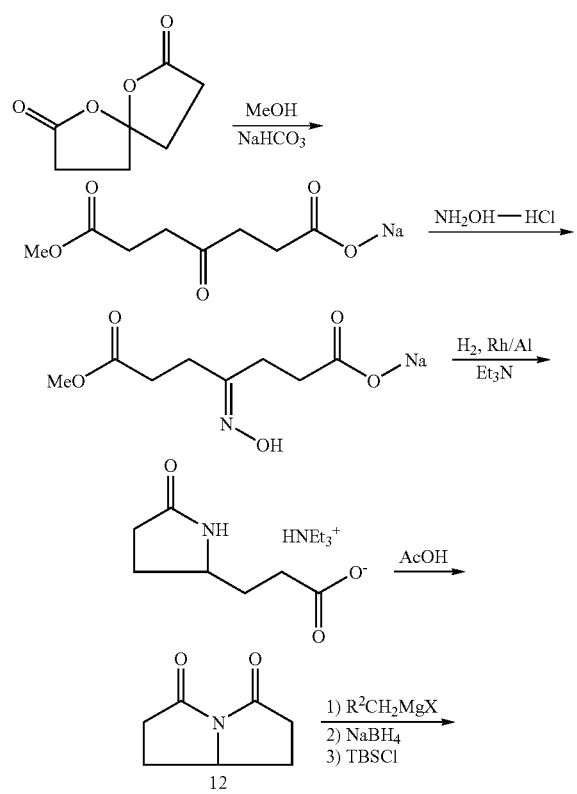

Scheme F

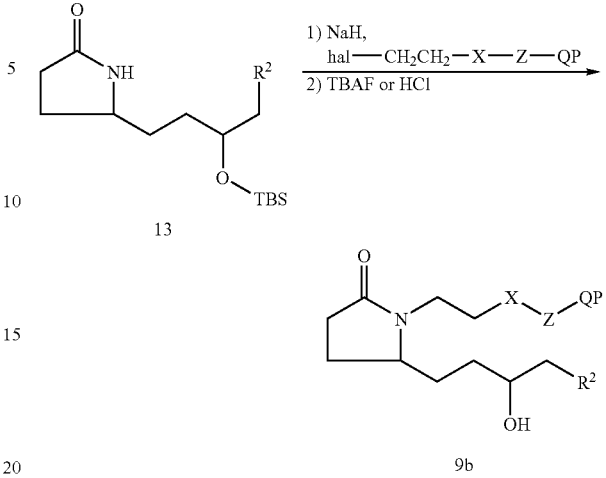

Compounds of Formula 9b of Scheme F are converted to compounds of Formula I by methods well known to those skilled in the art. In cases where the QP group is a carboxylic ester, either acidic or basic aqueous hydrolysis conditions may be utilized. Typically, lower alkyl esters are hydrolyzed by base catalyzed hydrolysis in a reaction inert solvent at ambient temperature to about the reflux temperature of the solvent being used. Preferably the lower alkyl ester is hydrolyzed with aqueous 1 N sodium hydroxide in methanol at a suitable temperature, preferably at ambient temperature. When QP is a benzyl ester or a t-butyl ester, standard deprotection methods are utilized as described in Greene, T. W.; Wuts, P. G. M., Protective Groups in Organic Synthesis, 2$^{nd}$ ed.; John Wiley and Sons Inc.: New York, 1991. When QP is a nitrile and not a protected carboxylic acid, a preferred method for preparation of the tetrazole is treatment of the nitrile with dibutyltin oxide and trimethylsilylazide in refluxing toluene (S. J. Wittenberger and B. G. Donner, J. Org. Chem. 1993, 58, 4139-4141). For a review of alternative preparations of tetrazoles see R. N. Butler, Tetrazoles, in Comprehensive Heterocyclic Chemistry; Potts, K. T. Ed.; Pergamon Press: Oxford, 1984, Vol. 5, p 791-838.

The methods of the present invention for the treatment of hypertension, liver failure, loss of patency of the ductus arteriosis, glaucoma or ocular hypertension in a patient, is demonstrated by the activity of those agonists in conventional assays, including the prostaglandin E$_2$ receptor subtype binding assay, the cyclic AMP assay, and in vivo assays which demonstrate the Formula I compounds hypotensive effect. The methods of the present invention for the treatment of liver failure can be demonstrated in an in vivo liver failure model. Such assays also provide a means by which the activities of the EP$_4$ receptor selective agonists of Formula I can be compared with each other and with the activity of other known compounds and compositions. The results of these comparisons are useful for determining dosage levels of the EP$_4$ selective agonists of Formula I in mammals, including humans, for the treatment of such diseases.

Administration of the selective EP$_4$ receptor agonists according to the methods of this invention can be via any mode that delivers the EP$_4$ receptor selective agonist systemically and/or locally (e.g., at the ductus arteriosus, liver, vasculature, or eye). These methods include oral routes, parenteral, intraduodenal routes, etc. Generally, the compounds of this invention are administered orally, but parenteral administration (e.g., intravenous, intramuscular, transdermal, subcutaneous, rectal or intramedullary) may be utilized, for example, where oral administration is inappropriate for the target or where the patient is unable to ingest the drug.

The methods of this invention are used for the treatment of hypertension, liver failure, loss of patency of the ductus arteriosus, glaucoma or ocular hypertension can be carried out by either systemic or local application (e.g., to the ductus arteriosus, liver, vasculature, or eye) of the selective $EP_4$ receptor agonists. The selective $EP_4$ receptor agonists useful in the methods of this invention are applied to the sites of the vasculature, liver, ductus arteriosus, or eye for example, either by injection of the compound in a suitable solvent, or in cases of open surgery, by local application thereto of the compound in a suitable vehicle, carrier or diluent. In certain instances it may be desirable to administer the selective $EP_4$ receptor agonist via a catheter to the site to be treated. For administration to the eye an ophthalmic preparation, such as a gel, ointment or ophthalmic solution or suspension can be employed.

In any event, the amount and timing of compounds administered will be dependent on the subject being treated, on the severity of the affliction, on the manner of administration and on the judgment of the prescribing physician. Thus, because of patient to patient variability, the dosages given herein are a guideline and the physician may titrate doses of the compound to achieve the treatment (e.g., reduce hypertension) that the physician considers appropriate for the patient. In considering the degree of treatment desired, the physician must balance a variety of factors such as the age of the patient, body weight of the patient, symptom, presence of preexisting disease, the desired therapeutic effect, the route of administration, and the duration of the treatment, etc. In the human adult, the dose administered is generally 1 µg to 100 mg, by oral administration, from once up to several times per day, and from 0.1 µg to 10 mg, by parenteral administration (preferably intravenously) from once up to several times per day, or by continuous administration for from 1 to 24 hours per day by intravenous infusion. For the treatment of neonates the dosage will have to be adjusted accordingly due to the patient's young age and low body weight. In general, in the methods of the present invention, an amount of a compound of Formula I is used that is sufficient to treat hypertension, liver failure, loss of patency of the ductus arteriosus, glaucoma or ocular hypertension. As the doses to be administered depend upon various conditions, there are cases in which doses lower or higher than the ranges specified above can be used.

The compounds used in the methods of this invention are generally administered in the form of a pharmaceutical composition comprising at least one of the compounds of this invention together with a pharmaceutically acceptable carrier, vehicle or diluent. Thus, the selective $EP_4$ receptor agonist can be administered individually in any conventional local, oral, intranasal, parenteral, rectal, topical (including ophthalmic) or transdermal dosage form.

For oral administration the pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tableting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compositions of this invention can be combined with various sweetening agents, flavoring agents, coloring agents, emulsifying agents and/or suspending agents, as well as such diluents as water, ethanol, propylene glycol, glycerin or various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

For purposes of ophthalmic administration, an aqueous solution of the compound of Formula I is generally preferred (typical concentration range is 0.001 to approximately 1% weight/volume). The aqueous solution can then be administered by instilling drops of the solution to the patient's eyes (usually 1 to 2 drops administered 1 to 4 times a day). For compounds of Formula I with less water solubility, an aqueous suspension may be preferred. Other ophthalmic compositions known in the art, such as viscous or semi-viscous gels, or other types of solid or semi-solid compositions containing compounds of Formula I may be employed. The ophthalmic composition may also contain a preservative such as benzalkonium chloride, chlorobutanol, edetate disodium, phenylethyl alcohol, phenylmercuric acetate, phenyl mercuric nitrate, methyl paraben, propyl paraben, polyquaternium-1, sorbic acid, thimerosal, or other known preservatives (typical concentration range of the preservative is 0.001 to 1.0% weight/volume). A surfactant, such as Tween 80, can also be used in the ophthalmic composition. Various vehicles, such as polyvinyl alcohol, povidone, hydroxypropyl methyl cellulose, poloxamers, carboxymethyl cellulose, hydroxyethyl cellulose cyclodextrin and water can be used for the ophthalmic composition. The tonicity of the ophthalmic composition can be adjusted using a tonicity adjustor such as sodium chloride, potassium chloride, mannitol or glycerin. The ophthalmic composition can be buffered, preferably to a range of 4.5 to 8.0, using buffers such as acetate buffers, citrate buffers, phosphate buffers and borate buffers. The pH of the ophthalmic composition can be adjusted, preferably to a range between 4.5 to 8.0, using an appropriate acid or base. Antioxidants, such as sodium metabisulfite, sodium thiosulfate, acetylcysteine, butylated hydroxyanisole and butylated hydroxytoluene can also be used in the ophthalmic composition.

Methods of preparing various pharmaceutical compositions with a certain amount of active ingredient are known, or will be apparent in light of this disclosure, to those skilled in the art. For examples of methods of preparing pharmaceutical compositions, see *Remington: The Science and Practice of Pharmacy*, Alfonso R. Gennaro, Mack Publishing Company, Easton, Pa., 19th Edition (1995).

Advantageously, the present invention also provides kits for use by a consumer to treat hypertension, liver failure, loss of patency of the ductus arteriosus, glaucoma or ocular hypertension. The kits comprise a) a pharmaceutical composition comprising a selective $EP_4$ receptor agonist of Formula I; and b) instructions describing methods of using the pharmaceutical compositions to treat hypertension, liver failure, loss of patency of the ductus arteriosus, glaucoma or ocular hypertension.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or other health care provider, or patient, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter that indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits of the present invention may also include, in addition to a selective $EP_4$ receptor agonist of Formula I, one or more additional pharmaceutically active compounds. Preferably, the additional compound is a HMG-CoA reductase inhibitor or antihypertensive agent. The additional compound or compounds may be administered in the same dosage form as the selective $EP_4$ receptor agonist of Formula I or in different dosage forms. Likewise, the additional compounds can be administered at the same time as the selective $EP_4$ receptor agonist of Formula I or at different times.

In the methods of the present invention it is to be understood that the selective $EP_4$ receptor agonists of Formula I can be administered in combination with other pharmaceutical agents. For example, in the methods for treating hypertension, the selective $EP_4$ receptor agonists of Formula I can be administered in combination with another antihypertensive agent. Certain patients suffering from hypertension also suffer from other disorders such as hypercholesterolemia or hypertriglyceridemia. In cases such as these it is to be understood that the selective $EP_4$ receptor agonists of Formula I can be administered in combination with an HMG-CoA reductase inhibitor. For patients suffering from glaucoma, the selective $EP_4$ receptor agonists can be administered in combination with another anti-glaucoma agent.

Any HMG-CoA reductase inhibitor may be employed as an additional compound in the combination therapy aspect of the present invention. The term "HMG-CoA reductase inhibitor" or "statin" refers to a compound that inhibits the biosynthesis of hydroxymethylglutaryl-coenzyme A to mevalonic acid as catalyzed by the enzyme HMG-CoA reductase. Such inhibition may be determined readily by one of skill in the art according to standard assays (e.g., Methods of Enzymology 1981, 71, 455-509; and the references cited therein). A variety of these compounds are described and referenced below. HMG-CoA reductase inhibitors may be readily prepared by processes known in the chemical arts. Mevastatin, lovastatin, pravastatin, velostatin, simvastatin, fluvastatin, cerivastatin and mevastatin, dalvastatin, fluindostatin and rivastatin may be made in accordance with the process set forth in U.S. Pat. No. 3,983,140, U.S. Pat. No. 4,231,938, U.S. Pat. No. 4,346,227, U.S. Pat. No. 4,448,784, U.S. Pat. No. 4,450,171, U.S. Pat. No. 4,739,073, U.S. Pat. No. 5,177,080, U.S. Pat. No. 5,177,080, European Patent Application No. 738,510 A2, European Patent Application No. 363,934 A1 and EP 491,226 respectively.

Atorvastatin may readily be prepared as described in U.S. Pat. No. 4,681,893. The hemicalcium salt of atorvastatin, which is currently sold as Lipitor®, may readily be prepared as described in U.S. Pat. No. 5,273,995. Other pharmaceutically-acceptable cationic salts of atorvastatin may be readily prepared by reacting the free acid form of atorvastatin with an appropriate base, usually one equivalent, in a co-solvent. Other HMG-CoA reductase inhibitors will be known to those skilled in the art. Examples of marketed products containing HMG-CoA reductase inhibitors that can be used in combination with compounds of Formula I in the methods of the present invention include Lescol®, Lipitor®, Mevacor®, Pravachol® and Zocor®.

It is preferred that said statin is mevastatin, lovastatin, pravastatin, velostatin, simvastatin, fluvastatin, cerivastatin, mevastatin, dalvastatin, fluindostatin or atorvastatin, or a prodrug thereof, or a pharmaceutically acceptable salt of said compound or prodrug.

It is especially preferred that said statin is atorvastatin, most preferably atorvastatin calcium.

The selective $EP_4$ receptor agonists of Formula I can also be administered in combination with antihypertensives in the methods of the present invention for the treatment of hypertension. Examples of classes of compounds that can be used to treat hypertension (antihypertensives) include calcium channel blockers, angiotensin converting enzyme (ACE) inhibitors, diuretics, angiotensin II receptor blockers, β-adrenergic blockers, and α-adrenergic blockers. In addition, combinations of compounds in the above-recited classes have been used to treat hypertension.

Some examples of specific calcium channel blockers that can be used in combination with the selective $EP_4$ receptor agonists of Formula I include amlodipine, including the besylate salt; nifedipine; lercanidipine, verapamil, and diltiazem. Some examples of specific α-adrenergic blockers and related compounds include doxazosin, including the mesylate salt; prazosin, including the hydrochloride salt; and prazosin hydrochloride/polythiazide. Some examples of specific β-adrenergic blockers that can be used in combination with the selective $EP_4$ receptor agonists of Formula I include sotalol, including the hydrochloride salt; timolol, including the maleate salt; propanolol, including the hydrochloride salt; acebutolol, including its hydrochloride salt; betaxolol, including the hydrochloride salt; penbutolol, including its sulfate salt; nadolol; bisoprolol, including the fumarate salt; atenolol; and metoprolol, including the succinate salt. Angiotensin II inhibitors such as candesartan cilexetil, irbesartan, losartan potassium, valsartan, and telmisartan can also be used in combination with the selective $EP_4$ receptor agonists of Formula I. Diuretics such as carbonic anhydrase inhibitors, combination diuretics, loop diuretics, potassium-sparing diuretics and thiazide and related diuretics can be used in combination with the compounds of Formula I. Some examples of specific diuretics that can be used in combination with the compounds of Formula I include hydrochlorothiazide, dichlorphenamide, spironolactone with hydrochlorothiazide, triamterene, hydrochlorothiazide with triamterene, amiloride hydrochloride, amiloride hydrochloride with hydrochlorothiazide, torsemide, ethacrynic acid, furosemide, hydroflumethazide, chlorothiazide, methyclothiazide, indapamide, metolazone, polythiazide and chlorthalidone. Some examples of specific ACE inhibitors including quinapril, captopril, alacepril, moveltipril, zofenopril, enalapril, enalaprilat, delapril, ramipril, spirapril, lisinopril, benazepril, cilazapril, perindopril, fosinopril and trandolapril can also be used in combination with the selective $EP_4$ receptor agonists of Formula I.

Combination therapy can also be used in the methods of the present invention for the treatment of glaucoma or ocular hypertension. For the treatment of glaucoma or ocular hypertension, the selective $EP_4$ receptor agonists of Formula I can be combined with other medicaments known to be useful for the treatment of glaucoma (anti-glaucoma agents), such as β-adrenergic blocking agents, carbonic anhydrase inhibitors, miotics and sympathomimetics. For example, β-adrenergic agents such as betaxolol, including its hydrochloride salt, and timolol, including its maleate salt can be combined with the selective $EP_4$ receptor agonists of Formula I. Some examples of specific carbonic anhydrase inhibitors that can be used in combination with the selective $EP_4$ receptor agonists of Formula I include brinzolamide, dichlorphenamide, and dorzolamide, including its hydrochloride salt. Miotics, such as demecarium bromide, can also be used in combination with the selective $EP_4$ receptor agonists of Formula I. Sympathomimetics, such as brimonidine, including its tartrate salt, pheniramine, including its maleate salt, and phenylephrine, including its hydrochloride salt, can be used in combination with the selective $EP_4$ receptor agonists of Formula I.

In the combination therapy aspect of the methods of the present invention, the selective $EP_4$ receptor agonists of Formula I and any additional compounds, such as the HMG-CoA reductase inhibitors and/or antihypertensive agents or the anti-glaucoma agents, can be administered in the same dosage form or in separate dosage forms. The dosage forms can be the same (e.g., both tablets) or different. Likewise, the compounds can be administered at the same time or at different times. All variations are intended to be included in the methods of the present invention.

The documents cited herein, including any patents and patent applications, are hereby incorporated by reference.

EXPERIMENTAL SECTION

General Experimental Procedures

NMR spectra were recorded on a Varian Unity 400 spectrometer (Varian Co., Palo Alto, Calif.) at about 23° C. at 400 MHz for proton nuclei. Chemical shifts are expressed in parts per million. The peak shapes are denoted as follows: s, singlet; d, doublet; t, triplet; q, quartet; m, multiplet; bs, broad singlet. Atmospheric pressure chemical ionization (APCI) mass spectra were obtained on a Fisons Platform II Spectrometer (Micromass Inc., Beverly, Mass.). Where the intensity of chlorine or bromine-containing ions are described the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Medium pressure chromatography was performed using a Biotage purification system (Biotage, Dyax Corporation, Charlottesville, Va.) under nitrogen pressure. Flash chromatography was performed with either Baker Silica Gel (40 µm) (J. T. Baker, Phillipsburg, N.J.) or Silica Gel 60 (EM Sciences, Gibbstown, N.J.) in glass columns under low nitrogen pressure. Radial Chromatography was performed using a Chromatotron (Harrison Research, Palo Alto, Calif.). Preparative Chromatography was performed using Analtech Uniplates Silica Gel GF (20×20 cm) (Analtech, Inc. Newark, Del.). Dimethylformamide (DMF), tetrahydrofuran (THF), and dichloromethane ($CH_2Cl_2$) used as reaction solvents were the anhydrous grade supplied by Aldrich Chemical Company (Milwaukee, Wis.). The term "concentrated" refers to removal of solvent at water aspirator pressure on a rotary evaporator. The term "EtOAc" means ethyl acetate. The term "$Et_2O$" means diethyl ether. The term "MeOH" means methanol. The abbreviation 'h' stands for hours. The term "TBAF" refers to tetrabutylammonium fluoride. The term "DMAP" refers to dimethylaminopyridine. The terms "dichloromethane" and "methylene chloride" are synonymous and are used interchangeably throughout this description and in the following compounds and preparations section. The following section describes preparations and compounds of Formula I. The compounds described below can be used in the methods of the present invention.

The examples presented herein are intended to illustrate particular embodiments of the invention, and are not intended to limit the specification or the claims in any manner.

Preparation of Specific Embodiments of Formula I Compounds

The following section provides specific embodiments of Formula I compounds (Compounds 1A-1H, 2A-2K, 3A-3M, 4A-4B, and 5A-5B) and preparations (Preparations 1-26) useful for their synthesis. The compounds provided can be used in the methods of the present invention.

Compound 1A

4-{3-[2-(3-Hydroxy-4-phenyl-butyl)-5-oxo-pyrrolidin-1-yl]-propyl}-benzoic acid

Step A: 5-(3-Oxo-4-phenyl-butyl)-pyrrolidin-2-one. To a solution of tetrahydro-pyrrolizine-3,5-dione (5 g, 36 mmol) in $CH_2Cl_2$ (320 mL) at 0° C. was added benzyl magnesium chloride (1M solution in THF, 39 mL, 39 mmol) dropwise. The solution was stirred at 0° C. for 3 h and was quenched with saturated aqueous ammonium chloride. After warming to room temperature, the aqueous solution was extracted with $CH_2Cl_2$ (3×). The combined organic extracts were dried ($MgSO_4$), filtered and concentrated. The residue was purified by medium pressure chromatography eluting with a solvent gradient (1% MeOH in $CH_2Cl_2$ to 2% MeOH in $CH_2Cl_2$) to yield 5.9021 g of 5-(3-oxo-4-phenyl-butyl)-pyrrolidin-2-one. $^1$H NMR ($CDCl_3$) δ 87.35-7.18 (m, 5H), 3.69 (s, 2H), 3.56 (m, 1H), 2.50 (t, 2H), 2.27 (m, 2H), 2.15 (m, 1H), 1.73 (m, 2H), 1.61 (m, 1H).

Step B: 5-(3-Hydroxy-4-phenyl-butyl)-pyrrolidin-2-one. To a solution of 5-(3-oxo-4-phenyl-butyl)-pyrrolidin-2-one (5.902 g, 25.52 mmol) in EtOH (30 mL) at 0° C. was added $NaBH_4$ (485 mg, 12.76 mmol) and the reaction mixture was stirred at 0° C. for 2.5 h. The reaction mixture was quenched with saturated aqueous ammonium chloride. Water and $CH_2Cl_2$ were added. The aqueous layer was washed with $CH_2Cl_2$ (2×) and the combined organic extracts were dried ($MgSO_4$), filtered and concentrated. The residue was purified by medium pressure chromatography with a solvent gradient (1:1 hexanes:EtOAc to EtOAc to 1% MeOH in $CH_2Cl_2$) to yield 4.3 g of 5-(3-hydroxy-4-phenyl-butyl)-pyrrolidin-2-one. $^1$H NMR ($CDCl_3$) δ 7.35-7.16 (m, 5H), 6.02 (m, 1H), 3.80 (m, 1H), 3.63 (m, 1H), 2.79 (m, 1H), 2.64 (m, 1H), 2.26 (m, 3H), 1.72-1.22 (m, 6H).

Step C: 5-[3-(tert-Butyl-dimethyl-silanyloxy)-4-phenyl-butyl]-pyrrolidin-2-one. To a solution of 5-(3-hydroxy-4-phenyl-butyl)-pyrrolidin-2-one (4.3 g, 18.43 mmol) in DMF (86 mL) was added tert-butyldimethylsilyl chloride (3.06 g, 20.3 mmol) followed by imidazole (2.5 g, 37 mmol) and DMAP (225 mg). The reaction mixture was stirred for 24 h and was quenched with saturated aqueous ammonium chloride. The aqueous solution was washed with EtOAc (3×) and the combined organic extracts were dried ($MgSO_4$), filtered and concentrated. The residue was purified by medium pressure chromatography eluting with a solvent gradient ($CH_2Cl_2$ to 1% MeOH in $CH_2Cl_2$ to 2% MeOH in $CH_2Cl_2$) to yield 5.94 g of 5-[3-(tert-butyl-dimethyl-silanyloxy)-4-phenyl-butyl]-pyrrolidin-2-one. $^1$H NMR ($CDCl_3$) δ 7.26-7.10 (m, 5H), 5.68 (m, 1H), 3.83 (m, 1H), 3.54 (m, 1H), 2.69 (m, 2H), 2.30-2.16 (m, 3H), 1.66-1.35 (m, 5H), 0.82 (s, 9H), −0.06 (d, 3H), −0.2 (d, 3H).

Step D: 4-(3-{2-[3-(tert-Butyl-dimethyl-silanyloxy)-4-phenyl-butyl]-5-oxo-pyrrolidin-1-yl}-propyl)-benzoic acid methyl ester. To a solution of 5-[3-(tert-butyl-dimethyl-silanyloxy)-4-phenyl-butyl]-pyrrolidin-2-one (3.20 g, 9.21 mmol) in DMF (30 mL) at 0° C. was added NaHMDS (1M in THF, 11.5 mL, 11.5 mmol). After 1 h, 4-(3-bromo-propyl)-benzoic acid methyl ester (2.84 g, 11.0 mmol) was added and the reaction mixture was stirred at 70° C. for 18 h. The DMF was removed in vacuo and the residue was dissolved in EtOAc. The organic solution was washed with water, dried ($MgSO_4$), filtered and concentrated. The residue was purified by medium pressure chromatography (30% EtOAc in hexanes) to yield 3.39 g of 4-(3-{2-[3-(tert-butyl-dimethyl-silanyloxy)-4-phenyl-butyl]-5-oxo-pyrrolidin-1-yl}-propyl)-benzoic acid methyl ester. $^1$H NMR ($CDCl_3$) (selected peaks) δ 7.92 (m, 2H), 7.25-7.09 (m, 7H), 3.86 (s, 3H), 3.80 (m, 1H), 3.61 (m, 1H), 3.46 (m, 1H), 2.90 (m, 1H), 2.78-2.57 (m, 4H), 2.38-2.18 (m, 2H), 0.83 (s, 9H); MS 524.1 (M+1).

Step E: 4-{3-[2-(3-Hydroxy-4-phenyl-butyl)-5-oxo-pyrrolidin-1-yl]-propyl}-benzoic acid methyl ester. To a solution of 4-(3-{2-[3-(tert-butyl-dimethyl-silanyloxy)-4-phenyl-butyl]-5-oxo-pyrrolidin-1-yl}-propyl)-benzoic acid methyl ester (3.37 g, 6.43 mmol) in THF (40 mL) at 0° C. was added tetra-butylammonium fluoride (1M in THF, 9.6 mL, 9.6 mmol). The reaction mixture was stirred at room temperature for 18 h and the volatiles were removed in vacuo. EtOAc was added and the organic solution was washed with saturated aqueous $NaHCO_3$ (2×), water (1×), and brine (1×). The organic solution was dried ($MgSO_4$), filtered and concentrated. The residue was purified by medium pressure chromatography eluting with EtOAc to yield 2.28 g of 4-{3-[2-(3-hydroxy-4-phenyl-butyl)-5-oxo-pyrrolidin-1-yl]-propyl}-benzoic acid methyl ester. $^1$H NMR ($CDCl_3$) (selected peaks) δ 7.91 (d, 2H), 7.32-7.15 (m, 7H), 3.86 (s, 3H), 3.75 (m, 1H), 3.63 (m, 1H), 3.54 (m, 1H), 2.94 (m, 1H), 2.78 (m, 1H), 2.61 (m, 3H); MS 410.1 (M+1).

Step F: 4-{3-[2-(3-Hydroxy-4-phenyl-butyl)-5-oxo-pyrrolidin-1-yl]-propyl}-benzoic acid. To a solution of 4-{3-[2-(3-hydroxy-4-phenyl-butyl)-5-oxo-pyrrolidin-1-yl]-propyl}-benzoic acid methyl ester (2.28 g, 5.57 mmol) in MeOH (20 mL) was added 2N NaOH (5 mL). The reaction mixture was stirred at room temperature for 20 h and was heated under reflux for 3 h. The volatiles were removed in vacuo and the residue was diluted with $CH_2Cl_2$ and 1N HCl. The aqueous solution was extracted with $CH_2Cl_2$ (2×) and the combined organic extracts were washed with brine. The organic solution was dried ($MgSO_4$), filtered and concentrated to yield the title compound (2.03 g). $^1$H NMR ($CDCl_3$) δ 7.98 (d, 2H), 7.34-7.18 (m, 7H), 3.80 (m, 1H), 3.67 (m, 1H), 3.58 (m, 1H), 2.97 (m, 1H), 2.81 (m, 1H), 2.68 (m, 3H), 2.45-2.27 (m, 2H), 2.13-1.30 (m, 9H); MS 396.3 (M+1), 394.2 (M−1).

Compound 1B 4-(3-{2-[3-Hydroxy-4-(3-trifluoromethyl-phenyl)-butyl]-5-oxo-pyrrolidin-1-yl}-propyl)-benzoic acid Step A: 5-[3-Oxo-4-(3-trifluoromethyl-phenyl)-butyl]-pyrrolidin-2-one Magnesium coils (1.13 g) were stirred under vacuum in a round bottom flask for 60 h. Anhydrous $Et_2O$ (5 mL) was added and the reaction mixture was cooled to 0° C. A solution of 3-trifluoromethylbenzyl chloride (1.0 mL, 7.5 mmol) in $Et_2O$ (25 mL) was added dropwise over 3 h. The reaction mixture was stirred for an additional 2.5 h. The solution was slowly added via a syringe and filtered through a nylon syringe filter into a solution of tetrahydro-pyrrolizine-3,5-dione (650 mg, 4.68 mmol) in $CH_2Cl_2$ (30 mL) at 0° C. After 2 h, the reaction mixture was quenched with 1N HCl and the aqueous solution was washed with $CH_2Cl_2$ (2×). The organic solutions were combined, dried ($MgSO_4$), filtered and concentrated. Medium pressure chromatography (1:1 hexanes:EtOAc) provided 5-[3-oxo-4-(3-trifluoromethylphenyl)-butyl]-pyrrolidin-2-one (1.376 g). $^1$H NMR ($CDCl_3$)

δ 7.38 (m, 4H), 3.78 (s, 2H), 3.61 (m, 1H), 2.58 (t, 2H), 2.30 (m, 2H), 2.20 (m, 1H), 2.86-1.59 (m, 3H).

Step B: 5-[3-Hydroxy-4-(3-trifluoromethyl-phenyl)-butyl]-pyrrolidin-2-one. Analogous to the procedure described for Compound 1A, Step B, 5-[3-oxo-4-(3-trifluoromethyl-phenyl)-butyl]-pyrrolidin-2-one (1.37 g, 4.59 mmol) was reduced with NaBH$_4$ (174 mg) at 0° C. over 2 h. Purification by medium pressure chromatography (2% MeOH in CH$_2$Cl$_2$) provided 5-[3-hydroxy-4-(3-trifluoromethyl-phenyl)-butyl]-pyrrolidin-2-one (1.19 g). $^1$H NMR (CDCl$_3$) δ 7.42 (m, 4H), 6.26 (m, 1H), 3.82 (m, 1H), 3.65 (m, 1H), 2.84 (m, 1H), 2.72 (m, 1H), 2.27 (m, 3H), 1.86 (m, 1H), 1.75-1.42 (m, 5H); MS 302.2 (M+1).

Step C: 5-[3-(tert-Butyl-dimethyl-silanyloxy)-4-(3-trifluoromethyl-phenyl)-butyl]-pyrrolidin-2-one. Analogous to the procedure described for Compound 1A, Step C, 5-[3-hydroxy-4-(3-trifluoromethyl-phenyl)-butyl]-pyrrolidin-2-one (1.19 g, 3.95 mmol) was protected with tert-butyidimethylsilyl chloride (893 mg, 6.22 mmol). Purification by medium pressure chromatography eluting with EtOAc provided 5-[3-(tert-butyl-dimethyl-silanyloxy)-4-(3-trifluoromethyl-phenyl)-butyl]-pyrrolidin-2-one. $^1$H NMR (CDCl$_3$) δ7.47-7.32 (m, 4H), 5.73 (m, 1H), 3.86 (m, 1H), 3.59 (m, 1H), 2.75 (m, 2H), 2.35-2.20 (m, 3H), 1.70-1.40 (m, 5H), 0.81 (s, 9H), −0.05 (d, 3H), −0.3 (d, 3H); MS 416.1 (M+1).

Step D: 4-(3-{2-[3-(tert-Butyl-dimethyl-silanyloxy)-4-(3-trifluoromethyl-phenyl)-butyl]-5-oxo-pyrrolidin-1-yl}-propyl)-benzoic acid methyl ester. Analogous to the procedure described for Compound 1A, Step D, 5-[3-(tert-butyl-dimethyl-silanyloxy)-4-(3-trifluoromethyl-phenyl)-butyl]-pyrrolidin-2-one (250 mg, 0.602 mmol) was alkylated with NaHMDS (1M in THF, 0.72 mL, 0.72 mmol) and 4-(3-bromo-propyl)-benzoic acid methyl ester (170 mg, 0.663 mmol) to yield 4-(3-{2-[3-(tert-butyl-dimethyl-silanyloxy)-4-(3-trifluoromethyl-phenyl)-butyl]-5-oxo-pyrrolidin-1-yl}-propyl)-benzoic acid methyl ester (300 mg). MS 592.1 (M+1).

Step E: 4-(3-{2-[3-Hydroxy-4-(3-trifluoromethyl-phenyl)-butyl]-5-oxo-pyrrolidin-1-yl}-propyl)-benzoic acid methyl ester. 4-(3-{2-[3-Hydroxy-4-(3-trifluoromethyl-phenyl)-butyl]-5-oxo-pyrrolidin-1-yl}-propyl)-benzoic acid methyl ester was prepared Analogous to the procedure described for Compound 1A, Step E. $^1$H NMR (CDCl$_3$) (selected peaks) δ 7.91 (d, 2H), 7.49-7.35 (m, 4H), 7.22 (d, 2H), 3.85 (s, 3H), 3.80 (m, 1H), 3.65 (m, 1H), 3.55 (m, 1H), 2.98-2.61 (m, 5H).

Step F: 4-(3-{2-[3-Hydroxy-4-(3-trifluoromethyl-phenyl)-butyl]-5-oxo-pyrrolidin-1-yl}-propyl)-benzoic acid. Analogous to the procedure described for Compound 1A, Step F, 4-(3-{2-[3-hydroxy-4-(3-trifluoromethyl-phenyl)-butyl]-5-oxo-pyrrolidin-1-yl}propyl)-benzoic acid methyl ester was hydrolyzed at room temperature over 24 h to generate 4-(3-{2-[3-hydroxy-4-(3-trifluoromethyl-phenyl)-butyl]-5-oxo-pyrrolidin-1-yl}-propyl)-benzoic acid. $^1$H NMR (CDCl$_3$) δ 7.98 (d, 2H), 7.52-7.37 (m, 4H), 7.26 (d, 2H), 3.82 (m, 1H), 3.68 (m, 1H), 3.58 (m, 1H), 2.98-2.66 (m, 5H), 2.34 (m, 2H), 2.09 (m, 1H), 1.95-1.37 (m, 7H); MS 464.2 (M+1).

Compound 1C 4-(3-{2-[4-(3-Chloro-phenyl)-3-hydroxy-butyl]-5-oxo-pyrrolidin-1-yl}-propyl)-benzoic acid Step A: 5-[4-(3-Chloro-phenyl)-3-oxo-butyl]-pyrrolidin-2-one. Analogous to the procedure described for Compound 1A, Step A, tetrahydro-pyrrolizine-3,5-dione (2 g, 14 mmol) was reacted with 3-chlorobenzylmagnesium chloride (0.25M in Et$_2$O, 62 mL, 15.5 mmol) over 2 h. Purification by medium pressure chromatography eluting with a solvent gradient (2:1 hexanes:EtOAc to EtOAc to 5% MeOH in CH$_2$Cl$_2$) provided 5-[4-(3-chloro-phenyl)-3-oxo-butyl]-pyrrolidin-2-one (1.9142 g). $^1$H NMR (CDCl$_3$) δ 7.27 (m, 2H), 7.19 (m, 1H), 7.08 (m, 1H), 6.27 (br, 1H), 3.68 (s, 2H), 3.60 (m, 1H), 2.52 (t, 2H), 2.29 (m, 2H), 2.21 (m, 1H), 1.88-1.60 (m, 3H); MS 266.2 (M+1), 264.2 (M−1).

Step B: 5-[4-(3-Chloro-phenyl)-3-hydroxy-butyl]-pyrrolidin-2-one. Analogous to the procedure described for Compound 1A, Step B, 5-[4-(3-chloro-phenyl)-3-oxo-butyl]-pyrrolidin-2-one (1.9 g, 7.15 mmol) was reduced with NaBH$_4$ (135 mg, 3.57 mmol). Purification by medium pressure chromatography eluting with a solvent gradient (1:1 hexanes: EtOAc to EtOAc to 1% MeOH in CH$_2$Cl$_2$ to 4% MeOH in CH$_2$Cl$_2$ to 8% MeOH in CH$_2$Cl$_2$) provided 5-[4-(3-chloro-phenyl)-3-hydroxy-butyl]-pyrrolidin-2-one (1.53 g). $^1$H NMR (CDCl$_3$) δ 7.22 (m, 3H), 7.07 (m, 1H), 6.51 (d, 1H), 3.82 (m, 1H), 3.66 (m, 1H), 2.77 (m, 1H), 2.66 (m, 1H), 2.33-2.19 (m, 3H), 2.04 (d, 1H), 1.74-1.45 (m, 5H); MS 268.2 (M+1).

Step C: 5-[3-(tert-Butyl-dimethyl-silanyloxy)-4-(3-chloro-phenyl)-butyl]-pyrrolidin-2-one. Analogous to the procedure described for Compound 1A, Step C, 5-[4-(3-chloro-phenyl)-3-hydroxy-butyl]-pyrrolidin-2-one (1.53 g, 5.71 mmol) was reacted with tert-butyidimethylsilyl chloride (0.97 g, 6.4 mmol). Purification by medium pressure chromatography using a solvent gradient (1:1 hexanes:EtOAc to EtOAc to 1% MeOH in CH$_2$Cl$_2$ to 2% MeOH in CH$_2$Cl$_2$ to 4% MeOH in CH$_2$Cl$_2$) provided 5-[3-(tert-butyl-dimethyl-silanyloxy)-4-(3-chloro-phenyl)-butyl]-pyrrolidin-2-one (1.77 g). $^1$H NMR (CDCl$_3$) δ7.16 (m, 3H), 7.01 (m, 1H), 5.61 (d, 1H), 3.83 (m, 1H), 3.58 (m, 1H), 2.68 (m, 2H), 2.28 (m, 3H), 1.73-1.36 (m, 5H), 0.84 (s, 9H), −0.05 (s, 3H), −0.2 (d, 3H).

Step D: 4-(3-{2-[3-(tert-Butyl-dimethyl-silanyloxy)-4-(3-chloro-phenyl)-butyl]-5-oxo-pyrrolidin-1-yl}-propyl)-benzoic acid methyl ester. Analogous to the procedure described for Compound 1A, Step D, 5-[3-(tert-butyl-dimethyl-silanyloxy)-4-(3-chloro-phenyl)-butyl]-pyrrolidin-2-one (246.5 mg, 0.645 mmol) was alkylated with NaHMDS (1M in THF, 0.77 mL, 0.77 mmol) and 4-(3-bromo-propyl)-benzoic acid methyl ester (200 mg, 0.767 mmol). Purification by medium pressure chromatography (5:1 hexanes:EtOAc to 1:1 hexanes:EtOAc to EtOAc to 1% MeOH in CH$_2$Cl$_2$ to 5% MeOH in CH$_2$Cl$_2$) provided 5-[3-(tert-butyl-dimethyl-silanyloxy)-4-(3-chloro-phenyl)-butyl]-pyrrolidin-2-one (246.3 mg). $^1$H NMR (CDCl$_3$) δ 7.94 (d, 2H), 7.25-7.13 (m, 5H), 7.01 (m, 1H), 3.88 (s, 3H), 3.82 (m, 1H), 3.66 (m, 1H), 3.50 (m, 1H), 2.94 (m, 1H), 2.73-2.57 (m, 4H), 2.47-2.27 (m, 2H), 2.12-11.23 (m, 8H), 0.84 (s, 9H), −0.05 (d, 3H), −0.2 (d, 3H); MS 558.5 (M+).

Step E: 4-(3-{2-[4-(3-Chloro-phenyl)-3-hydroxy-butyl]-5-oxo-pyrrolidin-1-yl}-propyl)-benzoic acid methyl ester. 4-(3-{2-[4-(3-Chloro-phenyl)-3-hydroxy-butyl]-5-oxo-pyrrolidin-1-yl}-propyl)-benzoic acid methyl ester was prepared Analogous to the procedure described for Compound 1A, Step E after purification by medium pressure chromatography (CH$_2$Cl$_2$ to 1% MeOH in CH$_2$Cl$_2$ to 2% MeOH in CH$_2$Cl$_2$ to 5% MeOH in CH$_2$Cl$_2$). $^1$H NMR (CDCl$_3$) δ 7.94 (d, 2H), 7.25-7.19 (m, 5H), 7.07 (m, 1H), 3.88 (s, 3H), 3.78 (m, 1H), 3.66 (m, 1H), 3.58 (m, 1H), 2.97 (m, 1H), 2.76 (m, 1H), 2.68-2.58 (m, 3H), 2.45-2.27 (m, 2H), 2.07 (m, 1H), 1.95-1.34 (m, 8H).

Step F: 4-(3-{2-[4-(3-Chloro-phenyl)-3-hydroxy-butyl]-5-oxo-pyrrolidin-1-yl}-propyl)-benzoic acid. Analogous to the procedure described for Compound 1A, Step F, 4-(3-{2-[4-(3-chloro-phenyl)-3-hydroxy-butyl]-5-oxo-pyrrolidin-1- yl}-propyl)-benzoic acid methyl ester was hydrolyzed with 6N NaOH at room temperature over 24 h to generate 4-(3-{2-[4-(3-chloro-phenyl)-3-hydroxy-butyl]-5-oxo-pyrrolidin-1-yl}-propyl)-benzoic acid. $^1$H NMR (CDCl$_3$) δ 7.98 (d, 2H), 7.27-7.09 (m, 6H), 3.81 (m, 1H), 3.65 (m, 2H), 2.99 (m, 2H), 2.75 (m, 3H), 2.39 (m, 2H), 2.20-1.30 (m, 9H).

Compound 1D 4-(3-{2-[4-(3-Fluoro-phenyl)-3-hydroxy-butyl]-5-oxo-pyrrolidin-1-yl}-propyl)-benzoic acid Step A: 5-[4-(3-Fluoro-phenyl)-3-oxo-butyl]-pyrrolidin-2-one. Analogous to the procedure described for Compound 1A, Step A, tetrahydro-pyrrolizine-3,5-dione (2 g, 14 mmol) was reacted with 3-fluorobenzylmagnesium chloride (0.25M in Et$_2$O, 62 mL, 15.5 mmol) over 2.5 h. Purification by medium pressure chromatography using a solvent gradient (1:1 hexanes:EtOAc to 2:1 EtOAc:hexanes to EtOAc to 2% MeOH in CH$_2$Cl$_2$ to 10% MeOH in CH$_2$Cl$_2$) provided 5-[4-(3-fluoro-phenyl)-3-oxo-butyl]-pyrrolidin-2-one (2.1730 g). $^1$H NMR (CDCl$_3$) δ 7.32-7.27 (m, 1H), 7.00-6.90 (m, 3H), 6.12 (bs, 1H), 3.69 (s, 2H), 3.59 (m, 1H), 2.52 (t, 2H), 2.30 (m, 2H), 2.19 (m, 1H), 1.75 (m, 2H), 1.65 (m, 1H).

Step B: 5-[4-(3-Fluoro-phenyl)-3-hydroxy-butyl]-pyrrolidin-2-one. Analogous to the procedure described for Compound 1A, Step B, 5-[4-(3-fluoro-phenyl)-3-oxo-butyl]-pyrrolidin-2-one (2.17 g, 8.71 mmol) was reduced with NaBH$_4$ (165 mg, 4.35 mmol). Purification by medium pressure chromatography using a solvent gradient (1:1 hexanes:EtOAc to EtOAc to 1% MeOH in CH$_2$Cl$_2$ to 3% MeOH in CH$_2$Cl$_2$ to 6% MeOH in CH$_2$Cl$_2$) provided 5-[4-(3-fluoro-phenyl)-3-hydroxy-butyl]-pyrrolidin-2-one (2.23 g). $^1$H NMR (CDCl$_3$) δ 7.27 (m, 1H), 6.94 (m, 3H), 6.38 (m, 1H), 3.82 (m, 1H), 3.66 (m, 1H), 2.79 (m, 1H), 2.67 (m, 1H), 2.33-2.21 (m, 3H), 1.92 (d, 1H), 1.75-1.40 (m, 5H); MS 252.2 (M+1).

Step C: 5-[3-(tert-Butyl-dimethyl-silanyloxy)-4-(3-fluoro-phenyl)-butyl]-pyrrolidin-2-one. Analogous to the procedure described for Compound 1A, Step C, 5-[4-(3-fluoro-phenyl)-3-hydroxy-butyl]-pyrrolidin-2-one (2.23 g, 8.87 mmol) was reacted with tert-butyldimethylsilyl chloride (1.47 g, 9.76 mmol). Purification by medium pressure chromatography using a solvent gradient (1:1 hexanes:EtOAc to EtOAc to 1% MeOH in CH$_2$Cl$_2$ to 2% MeOH in CH$_2$Cl$_2$ to 4% MeOH in CH$_2$Cl$_2$) provided 5-[3-(tert-butyl-dimethyl-silanyloxy)-4-(3-fluoro-phenyl)-butyl]-pyrrolidin-2-one (2.84 g). $^1$H NMR (CDCl$_3$) δ 7.23 (m, 1H), 6.88 (m, 3H), 5.75 (m, 1H), 3.85 (m, 1H), 3.57 (m, 1H), 2.71 (m, 2H), 2.30 (m, 2H), 2.25 (m, 1H), 1.70-1.38 (m, 5H), 0.84 (s, 9H), 0 (s, 3H), −0.2 (s, 3H).

Step D: 4-(3-{2-[3-(tert-Butyl-dimethyl-silanyloxy)-4-(3-fluoro-phenyl)-butyl]-5-oxo-pyrrolidin-1-yl}-propyl)-benzoic acid methyl ester. Analogous to the procedure described in Compound 1A, Step D, 5-[3-(tert-butyl-dimethyl-silanyloxy)-4-(3-fluoro-phenyl)-butyl]-pyrrolidin-2-one (254.7 mg, 0.697 mmol) was alkylated with NaHMDS (1M in THF, 0.84 mL, 0.84 mmol) and 4-(3-bromo-propyl)-benzoic acid methyl ester (200 mg, 0.778 mmol). Purificaton by medium pressure chromatography (5:1 hexanes:EtOAc to 1:1 hexanes:EtOAc to EtOAc to 1% MeOH in CH$_2$Cl$_2$ to 5% MeOH in CH$_2$Cl$_2$) provided 4-(3-{2-[3-(tert-butyl-dimethyl-silanyloxy)-4-(3-fluoro-phenyl)-butyl]-5-oxo-pyrrolidin-1-yl}-propyl)-benzoic acid methyl ester (275.3 mg). $^1$H NMR (CDCl$_3$) (selected peaks) δ 7.94 (d, 2H), 7.23 (m, 3H), 6.87 (m, 3H), 3.88 (s, 3H), 3.86 (m, 1H), 3.63 (m, 1H), 3.50 (m, 1H), 2.94 (m, 1H), 0.84 (s, 9H).

Step E: 4-(3-{2-[4-(3-Fluoro-phenyl)-3-hydroxy-butyl]-5-oxo-pyrrolidin-1-yl}-propyl)-benzoic acid methyl ester. Analogous to the procedure described for Compound 1A, Step E, 4-(3-{2-[3-(tert-butyl-dimethyl-silanyloxy)-4-(3-fluoro-phenyl)-butyl]-5-oxo-pyrrolidin-1-yl}-propyl)-benzoic acid methyl ester (275.3 mg, 0.508 mmol) was deprotected to yield 4-(3-{2-[4-(3-fluoro-phenyl)-3-hydroxy-butyl]-5-oxo-pyrrolidin-1-yl}-propyl)-benzoic acid methyl ester (217.2 mg). Purification was performed by medium pressure chromatography eluting with a solvent gradient (CH$_2$Cl$_2$ to 1% MeOH in CH$_2$Cl$_2$ to 2% MeOH in CH$_2$Cl$_2$ to 5% MeOH in CH$_2$Cl$_2$). $^1$H NMR (CDCl$_3$) δ 7.94 (d, J=7.88 Hz, 2H), 7.27 (m, 3H), 6.93 (m, 3H), 3.88 (s, 3H), 3.78 (m, 1H), 3.66 (m, 1H), 3.57 (m, 1H), 2.97 (m, 1H), 2.78 (m, 1H), 2.64 (m, 4H), 2.45-2.25 (m, 2H), 2.07 (m, 1H), 1.95-1.30 (m, 7H).

Step F: 4-(3-{2-[4-(3-Fluoro-phenyl)-3-hydroxy-butyl]-5-oxo-pyrrolidin-1-yl}-propyl)-benzoic acid. Analogous to the procedure described for Compound 1A, Step F, 4-(3-{2-[4-(3-fluoro-phenyl)-3-hydroxy-butyl]-5-oxo-pyrrolidin-1-yl}-propyl)-benzoic acid methyl ester was hydrolyzed with 6N NaOH at room temperature over 24 h to generate 4-(3-{2-[4-(3-fluoro-phenyl)-3-hydroxy-butyl]-5-oxo-pyrrolidin-1-yl}-propyl)-benzoic acid. $^1$H NMR (CDCl$_3$) δ 7.99 (d, 2H), 7.26 (m, 3H), 6.95 (m, 3H), 3.81 (m, 1H), 3.65 (m, 2H), 3.01 (m, 1H), 2.86-2.66 (m, 3H), 2.39 (m, 2H), 2.08 (m, 1H), 200-1.30 (m, 9H).

Compound 1E 4-(3-{2-[3-Hydroxy-4-(3-phenoxy-phenyl)-butyl]-5-oxo-pyrrolidin-1-yl}-propyl)-benzoic acid Step A: 5-[3-Oxo-4-(3-phenoxy-phenyl)-butyl]-pyrrolidin-2-one. Analogous to the procedure described for Compound 1B, Step A, tetrahydro-pyrrolizine-3,5-dione (650 mg, 4.68 mmol) and 3-phenoxybenzyl chloride (1.20 g, 5.49 mmol) were reacted over 3.5 h to provide 5-[3-oxo-4-(3-phenoxy-phenyl)-butyl]-pyrrolidin-2-one (924 mg). $^1$H NMR (CDCl$_3$) δ 7.30 (m, 3H), 7.10 (m, 1H), 6.99 (m, 2H), 6.92-6.84 (m, 3H), 3.66 (s, 2H), 3.57 (m, 1H), 2.52 (t, 2H), 2.27 (m, 2H), 2.17 (m, 1H), 1.80-1.58 (m, 3H).

Step B: 5-[3-Hydroxy-4-(3-phenoxy-phenyl)-butyl]-pyrrolidin-2-one. Analogous to the procedure described for Compound 1A, Step B, 5-[3-oxo-4-(3-phenoxy-phenyl)-butyl]-pyrrolidin-2-one (923.6 mg, 2.86 mmol) was reduced with NaBH$_4$ (54 mg, 1.4 mmol). Purification by medium pressure chromatography (1:1 hexanes:EtOAc to 2% MeOH in CH$_2$Cl$_2$ to 4% MeOH in CH$_2$Cl$_2$ to 10% MeOH in CH$_2$Cl$_2$) provided 5-[3-hydroxy-4-(3-phenoxy-phenyl)-butyl]-pyrrolidin-2-one (668.3 mg). $^1$H NMR (CDCl$_3$) δ 7.31 (m, 2H), 7.23 (m, 1H), 7.08 (m, 1H), 6.97 (d, 2H), 6.91 (d, 1H), 6.84 (m, 2H), 3.80 (m, 1H), 3.73 (m, 1H), 2.77-2.03 (m, 2H), 2.40 (m, 2H), 2.24 (m, 1H), 1.75-1.41 (m, 5H); MS 326.3 (M+1).

Step C: 5-[3-(tert-Butyl-dimethyl-silanyloxy)-4-(3-phenoxy-phenyl)-butyl]-pyrrolidin-2-one. Analogous to the procedure described for Compound 1A, Step C, 5-[3-hydroxy-4-(3-phenoxy-phenyl)-butyl]-pyrrolidin-2-one (668.3 mg, 2.05 mmol) was reacted with tert-butyldimethylsilyl chloride (341 mg, 2.26 mmol). Purification by medium pressure chromatography (CH$_2$Cl$_2$ to 1% MeOH in CH$_2$Cl$_2$ to 2% MeOH in CH$_2$Cl$_2$) provided 5-[3-(tert-butyl-dimethyl-silanyloxy)-4-(3-phenoxy-phenyl)-butyl]-pyrrolidin-2-one (673 mg). $^1$H NMR (CDCl$_3$) δ 7.32 (m, 2H), 7.22 (m, 1H), 7.09 (m, 1H), 6.99 (d, 2H), 6.89 (d, 1H), 6.83 (m, 2H), 3.85 (m, 1H), 3.58

(m, 1H), 2.76-2.62 (m, 2H), 2.32 (m, 2H), 2.23 (m, 1H), 1.73-1.34 (m, 5H), 0.84 (s, 9H), −0.03 (d, 3H), −0.16 (d, 3H); MS 440.7 (M+1).

Step D: 4-(3-{2-[3-(tert-Butyl-dimethyl-silanyloxy)-4-(3-phenoxy-phenyl)-butyl]-5-oxo-pyrrolidin-1-yl}-propyl)-benzoic acid methyl ester. Analogous to the procedure described for Compound 1A, Step D, 5-[3-(tert-butyl-dimethyl-silanyloxy)-4-(3-phenoxy-phenyl)-butyl]-pyrrolidin-2-one (200 mg, 0.455 mmol) was alkylated with NaHMDS (1M in THF, 0.55 mL, 0.55 mmol) and 4-(3-bromo-propyl)-benzoic acid methyl ester (128 mg, 0.501 mmol) to yield 4-(3-{2-[3-(tert-butyl-dimethyl-silanyloxy)-4-(3-phenoxy-phenyl)-butyl]-5-oxo-pyrrolidin-1-yl}-propyl)-benzoic acid methyl ester (173.1 mg). $^1$H NMR (CDCl$_3$) δ 7.94 (d, 2H), 7.32 (m, 2H), 7.25-7.19 (m, 3H), 7.09 (m, 1H), 6.98 (d, 2H), 6.88-6.81 (m, 3H), 3.88 (s, 3H), 3.84 (m, 1H), 3.64 (m, 1H), 3.50 (m, 1H), 2.95 (m, 1H), 2.76-2.57 (m, 4H), 2.37 (m, 2H), 2.03 (m, 1H), 1.92-1.67 (m, 3H), 1.56 (m, 1H), 1.46-1.25 (m, 3H), 0.84 (s, 9H), −0.04 (d, 3H), −0.15 (d, 3H).

Step E: 4-(3-{2-[3-Hydroxy-4-(3-phenoxy-phenyl)-butyl]-5-oxo-pyrrolidin-1-yl}-propyl)-benzoic acid methyl ester. 4-(3-{2-[3-Hydroxy-4-(3-phenoxy-phenyl)-butyl]-5-oxo-pyrrolidin-1-yl}-propyl)-benzoic acid methyl ester was prepared analogous to the procedure described for Compound 1A, Step E after purification by medium pressure chromatography (CH$_2$Cl$_2$ to 1% MeOH in CH$_2$Cl$_2$ to 2% MeOH in CH$_2$Cl$_2$ to 5% MeOH in CH$_2$Cl$_2$). $^1$H NMR (CDCl$_3$) δ 7.94 (d, 2H), 7.35-7.23 (m, 5H), 7.11 (m, 1H), 7.00 (d, 2H), 6.93-6.85 (m, 3H), 3.88 (s, 3H), 3.77 (m, 1H), 3.70-3.53 (m, 2H), 2.97 (m, 1H), 2.77 (m, 1H), 2.62 (m, 3H), 2.46-2.26 (m, 2H), 2.06 (m, 1H), 1.96-1.28 (m, 7H).

Step F: 4-(3-{2-[3-Hydroxy-4-(3-phenoxy-phenyl)-butyl]-5-oxo-pyrrolidin-1-yl}-propyl)-benzoic acid. Analogous to the procedure described for Compound 1A, Step F, 4-(3-{2-[3-hydroxy-4-(3-phenoxy-phenyl)-butyl]-5-oxo-pyrrolidin-1-yl}-propyl)-benzoic acid methyl ester was hydrolyzed with 6N NaOH at room temperature over 24 h to generate 4-(3-{2-[3-hydroxy-4-(3-phenoxy-phenyl)-butyl]-5-oxo-pyrrolidin-1-yl}-propyl)-benzoic acid. $^1$H NMR (CDCl$_3$) δ 7.99 (d, 2H), 7.37-7.26 (m, 5H), 7.12 (m, 1H), 7.03-6.88 (m, 5H), 3.82 (m, 1H), 3.66 (m, 2H), 3.00 (m, 1H), 2.85-2.60 (m, 4H), 2.41 (m, 2H), 2.09 (m, 1H), 2.03-1.28 (m, 8H).

Compound 1F

4-{3-[2-(4-Biphenyl-3-yl-3-hydroxy-butyl)-5-oxo-pyrrolidin-1-yl]-propyl}-benzoic acid Step A: 5-(3-Bromo-3-oxo-butyl)-pyrrolidin-2-one. Analogous to the procedure described for Compound 1A, Step A, tetrahydro-pyrrolizine-3,5-dione (5 g, 36 mmol) was reacted with 3-bromobenzylmagnesium bromide (0.25M in Et$_2$O, 155 mL, 38.8 mmol) over 2 h. Purification by medium pressure chromatography using a solvent gradient (1:1 hexanes:EtOAc to EtOAc to 5% MeOH in CH$_2$Cl$_2$) provided 5-(3-bromo-3-oxo-butyl)-pyrrolidin-2-one (7.84 g). $^1$H NMR (CDCl$_3$) δ 7.41-7.11 (m, 4H), 6.24 (bs, 1H), 3.67 (s, 2H), 3.60 (m, 1H), 2.52 (t, 2H), 2.32 (m, 2H), 2.20 (m, 1H), 1.88-1.60 (m, 3H).

Step B: 5-(3-Bromo-3-hydroxy-butyl)-pyrrolidin-2-one. Analogous to the procedure described for Compound 1A, Step B, 5-(3-bromo-3-oxo-butyl)-pyrrolidin-2-one (7.84 g, 25.3 mmol) was reduced with NaBH$_4$ (480 mg, 12.6 mmol). Purification by medium pressure chromatography using a solvent gradient (1:1 hexanes:EtOAc to EtOAc to 1% MeOH in CH$_2$Cl$_2$ to 3% MeOH in CH$_2$Cl$_2$ to 5% MeOH in CH$_2$Cl$_2$ to 8% MeOH in CH$_2$Cl$_2$) provided 5-(3-bromo-3-hydroxy-butyl)-pyrrolidin-2-one (6.76 g). $^1$H NMR (CDCl$_3$) δ 7.36-7.09 (m, 4H), 6.27 (m, 1H), 3.78 (m, 1H), 3.63 (m, 1H), 2.75 (m, 1H), 2.62 (m, 1H), 2.32-2.18 (m, 3H), 1.88 (m, 1H), 1.73-1.42 (m, 5H); MS 312.2, 314.1 (M+).

Step C: 5-[3-Bromo-3-(tert-butyl-dimethyl-silanyloxy)-butyl]-pyrrolidin-2-one. Analogous to the procedure described for Compound 1A, Step C, 5-(3-bromo-3-hydroxy-butyl)-pyrrolidin-2-one (6.76 g, 21.6 mmol) was reacted with tert-butyldimethylsilyl chloride (3.59 g, 23.8 mmol). Purification by medium pressure chromatography using a solvent gradient (CH$_2$Cl$_2$ to 1% MeOH in CH$_2$Cl$_2$ to 3% MeOH in CH$_2$Cl$_2$ to 5% MeOH in CH$_2$Cl$_2$ to 8% MeOH in CH$_2$Cl$_2$) provided 5-[3-bromo-3-(tert-butyl-dimethyl-silanyloxy)-butyl]-pyrrolidin-2-one (7.45 g). $^1$H NMR (CDCl$_3$) δ 7.30 (m, 2H), 7.12 (m, 1H), 7.04 (m, 1H), 5.71 (m, 1H), 3.81 (m, 1H), 3.56 (m, 1H), 2.66 (m, 2H), 2.32-2.17 (m, 3H), 1.70-1.35 (m, 5H), 0.82 (s, 9H), −0.06 (d, 3H), −0.24 (d, 3H); MS 426.2, 428.2 (M+).

Step D: 5-[4-Biphenyl-3-yl-3-(tert-butyl-dimethyl-silanyloxy)-butyl]-pyrrolidin-2-one. To a solution of 5-[3-bromo-3-(tert-butyl-dimethyl-silanyloxy)-butyl]-pyrrolidin-2-one (750 mg, 1.76 mmol) in DME (15 mL) was added phenylboronic acid (236 mg, 1.93 mmol). Palladium acetate (26.8 mg, 0.120 mmol) and tri-o-tolylphosphine (39.5 mg, 0.130 mmol) were added, followed by a solution of Na$_2$CO$_3$ (373 mg, 3.52 mmol) in water (1.8 mL). The reaction mixture was heated under reflux for 24 h. The reaction mixture was cooled and the volatiles were removed in vacuo. The residue was diluted with brine and EtOAc. The aqueous solution was washed with EtOAc (3×) and the combined organic extracts were dried (MgSO$_4$), filtered and concentrated. Purification by medium pressure chromatography eluting with a solvent gradient (1:1 hexanes:EtOAc to EtOAc to 1% MeOH in CH$_2$Cl$_2$ to 3% MeOH in CH$_2$Cl$_2$ to 5% MeOH in CH$_2$Cl$_2$) provided 5-[4-biphenyl-3-yl-3-(tert-butyl-dimethyl-silanyloxy)-butyl]-pyrrolidin-2-one (717.3 mg). $^1$H NMR (CDCl$_3$) δ 7.57 (m, 2H), 7.43 (m, 2H), 7.33 (m, 3H), 7.11 (m, 2H), 5.78 (m, 1H), 3.91 (m, 1H), 3.59 (m, 1H), 2.76 (m, 2H), 2.27 (m, 3H), 1.73-1.38 (m, 5H), 0.83 (s, 9H), −0.03 (d, 3H), −0.16 (d, 3H); MS 424.3 (M+1).

Step E: 4-(3-{2-[4-Biphenyl-3-yl-3-(tert-butyl-dimethyl-silanyloxy)-butyl]-5-oxo-pyrrolidin-1-yl}-propyl)-benzoic acid methyl ester. Analogous to the procedure described for Compound 1A, Step D, 5-[4-biphenyl-3-yl-3-(tert-butyl-dimethyl-silanyloxy)-butyl]-pyrrolidin-2-one (5.116 g, 12.08 mmol) was alkylated with 4-(3-bromo-propyl)-benzoic acid methyl ester (3.41 g, 13.3 mmol) over 20 h. Purification by medium pressure chromatography using a solvent gradient (5:1 hexanes:EtOAc to 1:1 hexanes:EtOAc to EtOAc to 1% MeOH in CH$_2$Cl$_2$ to 5% MeOH in CH$_2$Cl$_2$) provided 4-(3-{2-[4-biphenyl-3-yl-3-(tert-butyl-dimethyl-silanyloxy)-butyl]-5-oxo-pyrrolidin-1-yl}-propyl)-benzoic acid methyl ester (5.38 g). $^1$H NMR (CDCl$_3$) δ 7.93 (d, 2H), 7.56 (d, 2H), 7.43 (m, 3H), 7.34 (m, 3H), 7.23 (m, 2H), 7.12 (m, 1H), 3.89 (m, 1H), 3.87 (s, 3H), 3.64 (m, 1H), 3.49 (m, 1H), 2.95-2.61 (m, 5H), 2.30 (m, 2H), 2.01 (m, 1H), 1.89-1.70 (m, 3H), 1.59-1.24 (m, 4H), 0.84 (s, 9H), −0.04 (d, 3H), −0.16 (d, 3H).

Step F: 4-{3-[2-(4-Biphenyl-3-yl-3-hydroxy-butyl)-5-oxo-pyrrolidin-1-yl]-propyl}-benzoic acid methyl ester. Analogous to the procedure described for Compound 1A, Step E, 4-(3-{2-[4-biphenyl-3-yl-3-(tert-butyl-dimethyl-silanyloxy)-butyl]-5-oxo-pyrrolidin-1-yl}-propyl)-benzoic acid methyl ester (5.38 g, 8.97 mmol) was deprotected. Purification by medium pressure chromatography using a solvent gradient (hexanes to 2:1 hexanes:EtOAc to 1:1 hexanes:EtOAc to 0.5% MeOH in CH$_2$Cl$_2$ to 1% MeOH in CH$_2$Cl$_2$) provided 4-{3-[2-(4-biphenyl-3-yl-3-hydroxy-butyl)-5-oxopyrrolidin-1-yl]-propyl}-benzoic acid methyl ester (3.70 g). ¹H NMR (CDCl₃) δ 7.93 (d, 2H), 7.57 (d, 2H), 7.40 (m, 6H), 7.24 (m, 2H), 7.17 (m, 1H), 3.86 (s, 3H), 3.80 (m, 1H), 3.66 (m, 1H), 3.56 (m, 1H), 2.97 (m, 1H), 2.90-2.60 (m, 4H), 2.33 (m, 2H), 2.07 (m, 1H), 1.98-1.34 (m, 8H).

Step G: 4-{3-[2-(4-Biphenyl-3-yl-3-hydroxy-butyl)-5-oxo-pyrrolidin-1-yl]-propyl}-benzoic acid. Analogous to the procedure described for Compound 1A, Step F, 4-{3-[2-(4-biphenyl-3-yl-3-hydroxy-butyl)-5-oxo-pyrrolidin-1-yl]-propyl}-benzoic acid methyl ester (3.14 g, 6.47 mmol) was hydrolyzed with 6N NaOH (40 mL) in MeOH (160 mL) at room temperature over 24 h to generate 4-{3-[2-(4-biphenyl-3-yl-3-hydroxy-butyl)-5-oxo-pyrrolidin-1-yl]-propyl}-benzoic acid (2.73 g). ¹H NMR (CDCl₃) δ 7.98 (d, 2H), 7.57 (d, 2H), 7.40 (m, 6H), 7.26 (m, 2H), 7.18 (m, 1H), 3.85 (m, 1H), 3.68 (m, 1H), 3.59 (m, 1H), 2.98 (m, 1H), 2.88 (m, 1H), 2.70 (m, 3H), 2.36 (m, 2H), 2.08 (m, 1H), 1.85 (m, 3H), 1.69-1.35 (m, 4H); MS 470.1 (M−1), 472.2 (M+1).

Compound 1G 4-(3-{2-[4-(4-Fluoro-phenyl)-3-hydroxy-butyl]-5-oxo-pyrrolidin-1-yl}-propyl)-benzoic acid Step A: 5-[4-(4-Fluoro-phenyl)-3-oxo-butyl]-pyrrolidin-2-one. Analogous to the procedure described for Compound 1A, Step A, tetrahydro-pyrrolizine-3,5-dione (1.41 g, 10.1 mmol) was reacted with 4-fluorobenzylmagnesium chloride (0.25M in Et₂O, 50 mL, 12.5 mmol) over 5 h. Purification by medium pressure chromatography (2% MeOH in CH₂Cl₂) provided 5-[4-(4-fluoro-phenyl)-3-oxo-butyl]-pyrrolidin-2-one (2.64 g). ¹H NMR (CDCl₃) δ 7.18 (m, 2H), 7.03 (m, 2H), 6.34 (m, 1H), 3.70 (s, 2H), 3.62 (m, 1H), 2.54 (t, 2H), 2.34-2.15 (m, 3H), 1.82-1.61 (m, 3H).

Step B: 5-[4-(4-Fluoro-phenyl)-3-hydroxy-butyl]-pyrrolidin-2-one. Analogous to the procedure described for Compound 1A, Step B, 5-[4-(4-fluoro-phenyl)-3-oxo-butyl]-pyrrolidin-2-one (2.64 g, 10.6 mmol) was reduced with NaBH₄ (400 mg, 10.5 mmol) at room temperature for 1 h. Additional NaBH₄ (150 mg, 3.95 mmol) was added and the reaction mixture was stirred for 20 h. Purification by medium pressure chromatography using a solvent gradient (CH₂Cl₂ to 2% MeOH in CH₂Cl₂ to 4% MeOH in CH₂Cl₂) provided 5-[4-(4-fluoro-phenyl)-3-hydroxy-butyl]-pyrrolidin-2-one (2.01 g). ¹H NMR (CDCl₃) δ 7.14 (m, 2H), 6.98 (m, 2H), 6.78 (m, 1H), 3.76 (m, 1H), 3.65 (m, 1H), 2.76 (m, 1H), 2.64 (m, 1H), 2.32-2.18 (m, 4H), 1.72-1.47 (m, 5H).

Step C: 5-[3-(tert-Butyl-dimethyl-silanyloxy)-4-(4-fluoro-phenyl)-butyl]-pyrrolidin-2-one. Analogous to the procedure described for Compound 1A, Step C, 5-[4-(4-fluoro-phenyl)-3-hydroxy-butyl]-pyrrolidin-2-one (1.95 g, 7.79 mmol) was reacted with tert-butyldimethylsilyl chloride (1.47 g, 9.76 mmol). Purification by medium pressure chromatography (1% MeOH in CH₂Cl₂) provided 5-[3-(tert-butyl-dimethyl-silanyloxy)-4-(4-fluoro-phenyl)-butyl]-pyrrolidin-2-one. ¹H NMR (CDCl₃) δ 7.12 (m, 2H), 6.97 (m, 2H), 5.75 (m, 1H), 3.83 (m, 1H), 3.60 (m, 1H), 2.71 (m, 2H), 2.36-2.24 (m, 3H), 1.70-1.38 (m, 5H), 0.84 (s, 9H), −0.05 (d, 3H), −0.2 (d, 3H).

Step D: 4-(3-{2-[3-(tert-Butyl-dimethyl-silanyloxy)-4-(4-fluoro-phenyl)-butyl]-5-oxo-pyrrolidin-1-yl}-propyl)-benzoic acid methyl ester. Analogous to the procedure described for Compound 1A, Step D, 5-[3-(tert-butyl-dimethyl-silanyloxy)-4-(4-fluoro-phenyl)-butyl]-pyrrolidin-2-one (296 mg, 0.809 mmol) was alkylated with 4-(3-bromo-propyl)-benzoic acid methyl ester (276 mg, 1.07 mmol) over 72 h. Purification by medium pressure chromatography (1:1 hexanes:EtOAc) provided 4-(3-{2-[3-(tert-butyl-dimethyl-silanyloxy)-4-(4-fluoro-phenyl)-butyl]-5-oxo-pyrrolidin-1-yl}-propyl)-benzoic acid methyl ester (250 mg). ¹H NMR (CDCl₃) (selected peaks) δ 7.92 (d, 2H), 7.21 (d, 2H), 7.05 (m, 2H), 6.92 (m, 2H), 3.86 (s, 3H), 3.76 (m, 1H), 3.62 (m, 1H), 3.45 (m, 1H), 0.81 (s, 9H).

Step E: 4-(3-{2-[4-(4-Fluoro-phenyl)-3-hydroxy-butyl]-5-oxo-pyrrolidin-1-yl}-propyl)-benzoic acid methyl ester. Analogous to the procedure described for Compound 1A, Step E, 4-(3-{2-[3-(tert-butyl-dimethyl-silanyloxy)-4-(4-fluoro-phenyl)-butyl]-5-oxo-pyrrolidin-1-yl}-propyl)-benzoic acid methyl ester (241.2 mg, 0.445 mmol) was deprotected to yield, after medium pressure chromatography (1:1 hexanes:EtOAc to EtOAc to 1% MeOH in CH₂Cl₂ to 3% MeOH in CH₂Cl₂ to 5% MeOH in CH₂Cl₂), 4-(3-{2-[4-(4-fluoro-phenyl)-3-hydroxy-butyl]-5-oxo-pyrrolidin-1-yl}-propyl)-benzoic acid methyl ester (61.1 mg). ¹H NMR (CDCl₃) (selected peaks) δ 7.93 (d, 2H), 7.24 (d, 2H), 7.14 (m, 2H), 7.00 (m, 2H), 3.88 (s, 3H), 3.80-3.51 (m, 3H), 2.98 (m, 1H), 2.32 (m, 2H).

Step F: 4-(3-{2-[4-(4-Fluoro-phenyl)-3-hydroxy-butyl]-5-oxo-pyrrolidin-1-yl}-propyl)-benzoic acid. Analogous to the procedure described for Compound 1A, Step F, 4-(3-{2-[4-(4-fluoro-phenyl)-3-hydroxy-butyl]-5-oxo-pyrrolidin-1-yl}-propyl)-benzoic acid methyl ester (61.1 mg, 0.143 mmol) was hydrolyzed with 6N NaOH (1 mL) in MeOH (5 mL) at room temperature over 24 h. Purification by medium pressure chromatography eluting with a solvent gradient (CH₂Cl₂ to 2% MeOH in CH₂Cl₂ to 4% MeOH in CH₂Cl₂ to 6% MeOH in CH₂Cl₂ to 10% MeOH in CH₂Cl₂) provided the title compound (45 mg). ¹H NMR (CDCl₃) δ 7.97 (d, 2H), 7.25 (m, 2H), 7.14 (m, 2H), 6.99 (m, 2H), 3.75-3.58 (m, 3H), 2.97 (m, 1H), 2.69 (m, 4H), 2.40 (m, 2H), 2.15-1.35 (m, 9H); MS 413.8 (M+).

Compound 1H

4-{2-[2-(3-Hydroxy-4-phenyl-butyl)-5-oxo-pyrrolidin-1-yl]-ethoxy}-benzoic acid

Step A: 4-(2-{2-[3-(tert-Butyl-dimethyl-silanyloxy)-4-phenyl-butyl]-5-oxo-pyrrolidin-1-yl}-ethoxy)-benzoic acid ethyl ester. Analogous to the procedure described for Compound 1A, Step D, 5-[3-(tert-butyl-dimethyl-silanyloxy)-4-phenyl-butyl]-pyrrolidin-2-one (prepared in Compound 1A, Step C) (250 mg, 0.719 mmol) was alkylated with NaHMDS (1M in THF, 0.86 mL, 0.86 mmol) and 4-(2-bromo-ethoxy)-benzoic acid ethyl ester (216 mg, 0.791 mmol). The reaction temperature was maintained at 50° C. over 24 h. Purification by radial chromatography (hexanes to 4:1 hexanes:EtOAc) provided 4-(2-{2-[3-(tert-butyl-dimethyl-silanyloxy)-4-phenyl-butyl]-5-oxo-pyrrolidin-1-yl}-ethoxy)-benzoic acid ethyl ester (66.4 mg). ¹H NMR (CDCl₃) (selected peaks) δ 7.96 (m, 2H), 7.29-7.13 (m, 5H), 6.84 (m, 2H), 4.33 (q, 2H), 4.12 (m, 2H), 3.90 (m, 2H), 3.68 (m, 1H), 3.34 (m, 1H), 2.73 (m, 2H), 2.32 (m, 2H), 1.36 (t, 3H), 0.85 (s, 9H), −0.03 (s, 3H), −0.15 (d, 3H).

Step B: 4-{2-[2-(3-Hydroxy-4-phenyl-butyl)-5-oxo-pyrrolidin-1-yl]-ethoxy}-benzoic acid ethyl ester. Analogous to the procedure described for Compound 1A, Step E, 4-(2-{2-[3-(tert-butyl-dimethyl-silanyloxy)-4-phenyl-butyl]-5-oxo-pyrrolidin-1-yl}-ethoxy)-benzoic acid ethyl ester (66.4 mg, 0.122 mmol) was deprotected to provide 4-{2-[2-(3-hydroxy-4-phenyl-butyl)-5-oxo-pyrrolidin-1-yl]-ethoxy}-benzoic acid ethyl ester (52 mg) after purification by radial chromatography (CH₂Cl₂ to 2% MeOH in CH₂Cl₂). ¹H NMR (CDCl₃) δ 7.94 (m, 2H), 7.31-7.16 (m, 5H), 6.83 (m, 2H), 4.30 (q, 2H), 4.12 (m, 2H), 3.90 (m, 1H), 3.76 (m, 2H), 3.38 (m, 1H), 2.80 (m, 1H), 2.64 (m, 1H), 2.33 (m, 2H), 2.10 (m, 1H), 1.69-1.37 (m, 6H), 1.34 (t, 3H).

Step C: 4-{2-[2-(3-Hydroxy-4-phenyl-butyl)-5-oxo-pyrrolidin-1-yl]-ethoxy}-benzoic acid. Analogous to the procedure described for Compound 1A, Step F, 4-{2-[2-(3-hydroxy-4-phenyl-butyl)-5-oxo-pyrrolidin-1-yl]-ethoxy}-benzoic acid ethyl ester (52 mg, 0.122 mmol) was hydrolyzed with 6N NaOH (1 mL) to yield the title compound (41.5 mg). $^1$H NMR (CDCl$_3$) δ 7.98 (d, 2H), 7.32-7.16 (m, 5H), 6.85 (m, 2H), 4.13 (m, 2H), 3.92 (m, 1H), 3.81 (m, 1H), 3.75 (m, 1H), 3.40 (m, 1H), 2.82 (m, 1H), 2.66 (m, 1H), 2.36 (m, 2H), 2.10 (m, 2H), 1.70-1.34 (m, 5H); MS 398.4 (M+1), 396.3 (M−1).

Compound 2A

7-{2S-[3R-Hydroxy-4-(3-methoxymethyl-phenyl)-butyl]-5-oxo-pyrrolidin-1-yl}-heptanoic acid Step A: 7-(2R-Formyl-5-oxo-pyrrolidin-1-yl)-heptanoic acid ethyl ester. To a solution of 7-(2R-hydroxymethyl-5-oxo-pyrrolidin-1-yl)-heptanoic acid ethyl ester (1.63 g, 6.01 mmol) in anhydrous benzene (50 mL) was added 1-(3-dimethylaminopropyl)-3-ethylcarbodiimide hydrochloride (3.46 g, 18.03 mmol) and DMSO (1.5 mL, 24.04 mmol). The solution was cooled to 0° C. and pyridinium trifluoroacetate (1.28 g, 6.61 mmol) was added. The reaction mixture was stirred at 0° C. for 15 minutes and at room temperature for 2 h. The solution was decanted from the oily residue. The residue was washed with benzene (3×) and the combined benzene washes were concentrated in vacuo to provide 7-(2R-formyl-5-oxo-pyrrolidin-1-yl)-heptanoic acid ethyl ester, which was used in Step B without further purification.

Step B: 7-{2R-[4-(3-Methoxymethyl-phenyl)-3-oxo-but-1-enyl]-5-oxo-pyrrolidin-1-yl}-heptanoic acid ethyl ester. To a solution of [3-(3-methoxymethyl-phenyl)-2-oxo-propyl]-phosphonic acid diethyl ester (1.715 g, 5.46 mmol) in THF (43 mL) at 0° C. was added NaH (60% by weight in oil, 240 mg, 6.00 mmol) portionwise. The reaction mixture was stirred at room temperature for 45 minutes. The reaction mixture was cooled to 0° C. and a solution of 7-(2R-formyl-5-oxo-pyrrolidin-1-yl)-heptanoic acid ethyl ester (prepared in Step A, assumed 6.01 mmol) in THF (32 mL) was added dropwise. The reaction mixture was stirred at 0° C. for 15 minutes and at room temperature for 24 h. The reaction mixture was cooled to 0° C. and acetic acid was added until a pH of 5 was achieved. EtOAc and water were added and the aqueous solution was washed with EtOAc (3×). The organic solutions were combined, washed with water, dried (MgSO$_4$), filtered and concentrated. The residue was purified by medium pressure chromatography eluting with a solvent gradient (2:1 hexanes:EtOAc to 1:1 hexanes:EtOAc to 1% MeOH in CH$_2$Cl$_2$ to 3% MeOH in CH$_2$Cl$_2$) to provide 7-{2R-[4-(3-methoxymethyl-phenyl)-3-oxo-but-1-enyl]-5-oxo-pyrrolidin-1-yl}-heptanoic acid ethyl ester (1.4 g). $^1$H NMR (CDCl$_3$) δ 7.29 (m, 1H), 7.22 (m, 1H), 7.16 (s, 1H), 7.09 (d, 1H), 6.62 (dd, 1H), 6.19 (d, 1H), 4.41 (s, 2H), 4.10 (m, 3H), 3.82 (s, 2H), 3.51 (m, 1H), 3.36 (s, 2H), 2.67 (m, 1H), 2.43-2.18 (m, 5H), 1.75 (m, 1H), 1.56 (m, 2H), 1.42-1.17 (m, 9H).

Step C: 7-{2R-[3S-Hydroxy-4-(3-methoxymethyl-phenyl)-but-1-enyl]-5-oxo-pyrrolidin-1-yl}-heptanoic acid ethyl ester. To a solution of 7-{2R-[4-(3-methoxymethyl-phenyl)-3-oxo-but-1-enyl]-5-oxo-pyrrolidin-1-yl}-heptanoic acid ethyl ester (1.40 g, 3.26 mmol) in anhydrous CH$_2$Cl$_2$ (200 mL) was added (R)-2-methyl-CBS-oxazaborolidine (1M in toluene, 0.49 mL, 0.49 mmol) and the solution was cooled to −45° C. The reaction mixture was stirred for 20 minutes and catecholborane (1M in THF, 9.8 mL, 9.8 mmol) was added. The reaction mixture was stirred for 24 h at −45° C. and THF (100 mL) and HCl (1N, 100 mL) were added. The reaction mixture was stirred at room temperature for 24 h and at 40-45° C. for 1.5 h. The solution was diluted with CH$_2$Cl$_2$ and water and the layers were separated. The organic solution was cooled to 0° C. and was washed with ice-cold NaOH (0.5N) followed by brine. The organic solution was again washed with ice-cold NaOH (0.5 N) followed by brine and was dried (MgSO$_4$), filtered and concentrated. Purification by medium pressure chromatography eluting with a solvent gradient (5:1 hexanes:EtOAc to 2:1 hexanes:EtOAc to 1:1 hexanes:EtOAc to EtOAc to 2% MeOH in CH$_2$Cl$_2$) provided 7-{2R-[3S-hydroxy-4-(3-methoxymethyl-phenyl)-but-1-enyl]-5-oxo-pyrrolidin-1-yl}-heptanoic acid ethyl ester (1.2 g) as an approximate 12:1 mixture of 3S:3R alcohol diasteromers by HPLC analysis. $^1$H NMR (CDCl$_3$) (selected peaks) δ 7.26-7.07 (m, 4H), 5.67 (m, 1H), 5.43 (m, 1H), 4.39 (s, 2H), 4.36 (m, 1H), 4.06 (q, 2H), 3.98 (m, 1H), 3.41 (m, 1H), 3.35 (s, 3H); MS 432.3 (M+1), 430.3 (M−1).

Step D: 7-{2S-[3R-Hydroxy-4-(3-methoxymethyl-phenyl)-butyl]-5-oxo-pyrrolidin-1-yl}-heptanoic acid ethyl ester. To a solution of 7-{2R-[3S-hydroxy-4-(3-methoxymethyl-phenyl)-but-1-enyl]-5-oxo-pyrrolidin-1-yl}-heptanoic acid ethyl ester (1.2 g, 2.78 mmol) in EtOH (100 mL) was added 10% palladium on carbon (120 mg). The reaction mixture was hydrogenated on a Parr shaker at 45 psi for 24 h. The catalyst was removed via filtration through Celite® with the aid of EtOH. Purification by medium pressure chromatography eluting with a solvent gradient (CH$_2$Cl$_2$ to 2% MeOH in CH$_2$Cl$_2$ to 5% MeOH in CH$_2$Cl$_2$) (2×) provided 7-{2S-[3R-hydroxy-4-(3-methoxymethyl-phenyl)-butyl]-5-oxo-pyrrolidin-1-yl}-heptanoic acid ethyl ester (1.1 g). $^1$H NMR (CDCl$_3$) δ 7.28 (m, 1H), 7.18 (m, 2H), 7.11 (m, 1H), 4.42 (s, 2H), 4.08 (q, 2H), 3.82 (m, 1H), 3.58 (m, 2H), 3.38 (s, 3H), 2.84 (m, 2H), 2.66 (m, 1H), 2.41-2.23 (m, 4H), 2.08 (m, 1H), 1.78 (m, 1H), 1.64-1.37 (m, 9H), 1.28 (m, 4H), 1.22 (t, 3H).

Step E: 7-{2S-[3R-Hydroxy-4-(3-methoxymethyl-phenyl)-butyl]-5-oxo-pyrrolidin-1-yl}-heptanoic acid. To a solution of 7-{2S-[3R-hydroxy-4-(3-methoxymethyl-phenyl)-butyl]-5-oxo-pyrrolidin-1-yl}-heptanoic acid ethyl ester (1.1 g, 2.53 mmol) in EtOH (32 mL) was added NaOH (6N, 16 mL). The reaction mixture was stirred for 24 h and 1N HCl was added to obtain a pH of about 2. Brine and CH$_2$Cl$_2$ were added and the layers were separated. The aqueous solution was washed with 5% MeOH in CH$_2$Cl$_2$ (2 times). The combined organic layers were dried (MgSO$_4$), filtered and concentrated to provide the title compound of Example 2A (990 mg). $^1$H NMR (CDCl$_3$) δ 7.28 (m, 1H), 7.18 (m, 2H), 7.11 (m, 1H), 4.43 (s, 2H), 3.83 (m, 1H), 3.57 (m, 2H), 3.40 (s, 3H), 2.91 (m, 1H), 2.79 (m, 1H), 2.66 (m, 1H), 2.43-2.25 (m, 4H), 2.10 (m, 1H), 1.83 (m, 1H), 1.66-1.22 (m, 13H); MS 406.3 (M+1), 404.3 (M−1).

Compound 2B

7-[2R-(3-Hydroxy-4-naphthalen-2-yl-butyl)-5-oxo-pyrrolidin-1-yl]-heptanoic acid

Step A: 7-[2R-(4-Naphthalen-2-yl-3-oxo-but-1-enyl)-5-oxo-pyrrolidin-1-yl]-heptanoic acid ethyl ester. Analogous to the procedure described for Compound 2A, Step B, the anion derived from (3-naphthalen-2-yl-2-oxo-propyl)-phosphonic acid dimethyl ester (646 mg, 2.21 mmol) and NaH (60% by weight in oil, 81 mg, 2.02 mmol) was reacted with 7-(2R-formyl-5-oxo-pyrrolidin-1-yl)-heptanoic acid ethyl ester (assumed 1.84 mmol) over 163 h. Purification by medium pressure chromatography (1:1 hexanes:EtOAc to EtOAc) provided 7-[2R-(4-naphthalen-2-yl-3-oxo-but-1-enyl)-5-oxo-pyrrolidin-1-yl]-heptanoic acid ethyl ester (340 mg). $^1$H NMR (CDCl$_3$) δ 7.78 (m, 3H), 7.65 (s, 1H), 7.46 (m, 2H), 7.30 (d, 1H), 6.66 (dd, 1H), 6.24 (d, 1H), 4.10 (m, 3H), 3.99 (s, 2H), 3.45 (m, 1H), 2.63 (m, 1H), 2.44-2.18 (m, 5H), 1.75 (m, 1H), 1.52 (m, 2H), 1.37-1.06 (m, 9H); MS 436.1 (M+1), 434.1 (M−1).

Step B: 7-[2S-(4-Naphthalen-2-yl-3-oxo-butyl)-5-oxo-pyrrolidin-1-yl]-heptanoic acid ethyl ester. Analogous to the procedure described for Compound 2A, Step D, a mixture of 7-[2R-(4-naphthalen-2-yl-3-oxo-but-1-enyl)-5-oxo-pyrrolidin-1-yl]-heptanoic acid ethyl ester (337 mg, 0.774 mmol) and 10% palladium on carbon (50 mg) in EtOH (50 mL) was hydrogenated at 50 psi for 3 h. Medium pressure chromatography (1:1 hexanes:EtOAc to EtOAc) provided 7-[2S-(4-naphthalen-2-yl-3-oxo-butyl)-5-oxo-pyrrolidin-1-yl]-heptanoic acid ethyl ester (290 mg). $^1$H NMR (CDCl$_3$) δ 7.80 (m, 3H), 7.66 (s, 1H), 7.47 (m, 2H), 7.30 (m, 1H), 4.10 (q, 2H), 3.85 (s, 2H), 3.52 (m, 2H), 2.77 (m, 1H), 2.47 (m, 2H), 2.26 (m, 4H), 1.98 (m, 2H), 1.61-1.16 (m, 13H); MS 438.1 (M+1), 436.1 (M−1).

Step C: 7-[2S-(3-Hydroxy-4-naphthalen-2-yl-butyl)-5-oxo-pyrrolidin-1-yl]-heptanoic acid ethyl ester. To a solution of 7-[2S-(4-naphthalen-2-yl-3-oxo-butyl)-5-oxo-pyrrolidin-1-yl]-heptanoic acid ethyl ester (367 mg, 0.839 mmol) in EtOH (20 mL) was added NaBH$_4$ (32 mg, 0.839 mmol). The reaction mixture was stirred for 2 h and water (5 mL) was added. The volatiles were removed in vacuo and the remaining aqueous solution was washed with CHCl$_3$ (4×10 mL). The organic solutions were combined, dried (MgSO$_4$), filtered and concentrated. Purification by medium pressure chromatography (1:1 hexanes:EtOAc to EtOAc) provided 7-[2S-(3-hydroxy-4-naphthalen-2-yl-butyl)-5-oxo-pyrrolidin-1-yl]-heptanoic acid ethyl ester (332 mg). $^1$H NMR (CDCl$_3$) δ 7.80 (m, 3H), 7.65 (s, 1H), 7.46 (m, 2H), 7.33 (m, 1H), 4.07 (m, 2H), 3.91 (m, 1H), 3.60 (m, 2H), 2.98 (m, 1H), 2.84 (m, 2H), 2.35 (m, 2H), 2.25 (t, 2H), 2.10 (m, 1H), 2.01 (m, 1H), 1.81 (m, 1H), 1.70 (d, 1H), 1.68-1.37 (m, 7H), 1.36-1.20 (m, 7H); MS 440.1 (M+1).

Step D: 7-[2S-(3-Hydroxy-4-naphthalen-2-yl-butyl)-5-oxo-pyrrolidin-1-yl]-heptanoic acid. A solution of 7-[2S-(3-hydroxy-4-naphthalen-2-yl-butyl)-5-oxo-pyrrolidin-1-yl]-heptanoic acid ethyl ester (327 mg, 0.744 mmol), NaOH (1M, 0.8 mL), and MeOH (15 mL) was heated under reflux for 4 h. The volatiles were removed in vacuo and water (15 mL) was added. The aqueous solution was acidified to a pH of 5 with 1N HCl and the acidic solution was washed with CHCl$_3$ (4×10 mL). The organic solutions were combined, dried (MgSO$_4$), filtered and concentrated to provide 7-[2S-(3-hydroxy-4-naphthalen-2-yl-butyl)-5-oxo-pyrrolidin-1-yl]-heptanoic acid (180 mg). $^1$H NMR (CDCl$_3$) δ 7.80 (m, 3H), 7.65 (s, 1H), 7.46 (m, 2H), 7.33 (m, 1H), 3.94 (m, 1H), 3.58 (m, 2H), 3.02-2.80 (m, 3H), 2.34 (m, 4H), 2.08 (m, 2H), 1.67-1.23 (m, 13H); MS 412.1 (M+1), 410.2 (M−1).

Step E: Sodium salt of 7-[2S-(3-hydroxy-4-naphthalen-2-yl-butyl)-5-oxo-pyrrolidin-1-yl]-heptanoic acid. To a solution of 7-[2S-(3-hydroxy-4-naphthalen-2-yl-butyl)-5-oxo-pyrrolidin-1-yl]-heptanoic acid (35 mg, 0.0851 mmol) in MeOH (5 mL) at 0° C. was added NaOH (1M, 0.085 mL). The reaction mixture was stirred for 1.5 h at 0° C. and was concentrated in vacuo, azeotroping with CHCl$_3$ (3×5 mL) to yield the sodium salt of the title compound of Example 2B (37 mg). $^1$H NMR (CDCl$_3$) δ 7.69-7.24 (m, 7H), 3.78 (m, 1H), 3.40 (m, 2H), 2.80 (m, 6H), 2.16-1.70 (m, 4H), 1.43-1.18 (m, 12H).

Compound 2C

7-[2R-(4-Benzo[1,3]dioxol-5-yl-3-hydroxy-but-1-enyl)-5-oxo-pyrrolidin-1-yl]-heptanoic acid Step A: 7-[2R-(4-Benzo[1,3]dioxol-5-yl-3-oxo-but-1-enyl)-5-oxo-pyrrolidin-1-yl]-heptanoic acid ethyl ester. Analogous to the procedure described for Compound 2A, Step B, the anion generated from (3-benzo[1,3]dioxol-5-yl-2-oxo-propyl)-phosphonic acid dimethyl ester (12.65 g, 44.2 mmol) and NaH (60% by weight in oil, 1.62 g, 40.5 mmol) was reacted with 7-(2R-formyl-5-oxo-pyrrolidin-1-yl)-heptanoic acid ethyl ester (assumed 36.8 mmol) over 24 h. Purification by medium pressure chromatography (10% EtOAc in hexanes to 40% EtOAc in hexanes) provided 7-[2R-(4-benzo[1,3]dioxol-5-yl-3-oxo-but-1-enyl)-5-oxo-pyrrolidin-1-yl]-heptanoic acid ethyl ester (4.18 g). $^1$H NMR (CDCl$_3$) δ 6.76 (d, 1H), 6.63 (m, 3H), 6.20 (d, 1H), 5.94 (s, 2H), 4.13 (m, 3H), 3.74 (s, 2H), 3.52 (m, 1H), 2.71 (m, 1H), 2.38 (m, 2H), 2.26 (m, 3H), 1.78 (m, 1H), 1.58 (m, 5H), 1.46-1.19 (m, 6H).

Step B: 7-[2R-(4-Benzo[1,3]dioxol-5-yl-3-hydroxy-but-1-enyl)-5-oxo-pyrrolidin-1-yl]-heptanoic acid ethyl ester. Analogous to the procedure described for Compound 2B, Step C, 7-[2R-(4-benzo[1,3]dioxol-5-yl-3-oxo-but-1-enyl)-5-oxo-pyrrolidin-1-yl]-heptanoic acid ethyl ester (4.18 g, 9.74 mmol) was reacted with NaBH$_4$ (369 mg, 9.74 mmol) in EtOH (32 mL). The NaBH$_4$ addition was performed at 0° C. and the reaction mixture was stirred at room temperature for 3 h. Purification by medium pressure chromatography (EtOAc) provided 7-[2R-(4-benzo[1,3]dioxol-5-yl-3-hydroxy-but-1-enyl)-5-oxo-pyrrolidin-1-yl]-heptanoic acid ethyl ester (3.36 g).

Step C: 7-[2R-(4-Benzo[1,3]dioxol-5-yl-3-hydroxy-but-1-enyl)-5-oxo-pyrrolidin-1-yl]-heptanoic acid. Analogous to the procedure described for Compound 2A, Step E, 7-[2R-(4-benzo[1,3]dioxol-5-yl-3-hydroxy-but-1-enyl)-5-oxo-pyrrolidin-1-yl]-heptanoic acid ethyl ester (3.36 g, 7.79 mmol) was hydrolyzed with 2N NaOH (11 mL) in MeOH. Purification by medium pressure chromatography (50% EtOAc in hexanes to EtOAc to 5% MeOH in CH$_2$Cl$_2$) followed by a second column eluting with a solvent gradient (1% MeOH to CH$_2$Cl$_2$ to 5% MeOH in CH$_2$Cl$_2$) provided 7-[2R-(4-benzo[1,3]dioxol-5-yl-3-hydroxy-but-1-enyl)-5-oxo-pyrrolidin-1-yl]-heptanoic acid (2.26 g). $^1$H NMR (CDCl$_3$) δ 6.66 (m, 3H), 5.91 (s, 2H), 5.69 (m, 1H), 5.44 (m, 1H), 4.31 (m, 1H), 4.01 (m, 1H), 3.45 (m, 1H), 2.76 (m, 3H), 2.34 (m, 4H), 2.15 (m, 1H). 1.70-1.20 (m, 10H); MS 404.3 (M+1), 402.1 (M−1).

Step D: Sodium salt of 7-[2R-(4-Benzo[1,3]dioxol-5-yl-3-hydroxy-but-1-enyl)-5-oxo-pyrrolidin-1-yl]-heptanoic acid. The sodium salt was prepared by addition of NaHCO$_3$ (470 mg, 5.60 mmol) in water to a solution of 7-[2R-(4-benzo[1,3]dioxol-5-yl-3-hydroxy-but-1-enyl)-5-oxo-pyrrolidin-1-yl]-heptanoic acid (2.26 g, 5.60 mmol) in EtOH. The reaction mixture was stirred for 3 h and was concentrated in vacuo to provide the sodium salt of the title compound, Compound 2C. $^1$H NMR (CD$_3$OD) δ 6.65 (m, 3H), 5.85 (s, 2H), 5.67 (m, 1H), 5.34 (m, 1H), 4.24 (m, 1H), 4.09 (m, 1H), 3.45 (m, 1H), 2.79 (m, 2H), 2.61 (m, 2H), 2.29 (m, 2H), 2.16 (m, 3H), 1.68-1.17 (m, 9H).

Compound 2D

7-[2S-(4-Benzo[1,3]dioxol-5-yl-3-hydroxy-butyl)-5-oxo-pyrrolidin-1-yl]-heptanoic acid Step A: 7-[2S-(4-Benzo[1,3]dioxol-5-yl-3-hydroxy-butyl)-5-oxo-pyrrolidin-1-yl]-heptanoic acid. Analogous to the procedure described for Compound 2A, Step D, a mixture of 7-[2R-(4-benzo[1,3]dioxol-5-yl-3-hydroxy-but-1-enyl)-5-oxo-pyrrolidin-1-yl]-heptanoic acid (120 mg, 2.96 mmol), MeOH (30 mL), and 10% palladium on carbon (14 mg) was hydrogenated at 50 psi for 18 h to provide 7-[2S-(4-benzo[1,3]dioxol-5-yl-3-hydroxy-butyl)-5-oxo-pyrrolidin-1-yl]-heptanoic acid (71.3 mg). $^1$H NMR (CDCl$_3$) δ 6.68 (m, 3H), 5.92 (s, 2H), 3.74 (m, 1H), 3.57 (m, 2H), 2.87 (m, 1H), 2.72 (m, 1H), 2.54 (m, 1H), 2.31 (m, 4H), 2.10 (m, 1H), 1.99 (m, 1H), 1.66-1.19 (m, 13H); MS 406.3 (M+1), 404.3 (M−1).

Compound 2E

4-{3-[2R-(4-Benzo[1,3]dioxol-5-yl-3-hydroxy-but-1-enyl)-5-oxo-pyrrolidin-1-yl]-propyl}-benzoic acid Step A: 4-{3-[2R-(4-Benzo[1,3]dioxol-5-yl-3-oxo-but-1-enyl)-5-oxo-pyrrolidin-1-yl]-propyl}-benzoic acid methyl ester. Analogous to the procedure described for Compound 2A, Step B, the anion derived from (3-benzo[1,3]dioxol-5-yl-2-oxo-propyl)-phosphonic acid dimethyl ester (356 mg, 1.28 mmol) and NaH (60% in oil, 46 mg, 1.14 mmol) was reacted with 4-[3-(2R-formyl-5-oxo-pyrrolidin-1-yl)-propyl]-benzoic acid methyl ester (assumed 1.04 mmol) over 24 h. Purification by medium pressure chromatography (30% hexane in EtOAc to EtOAc) provided 4-{3-[2R-(4-benzo[1,3]dioxol-5-yl-3-oxo-but-1-enyl)-5-oxo-pyrrolidin-1-yl]-propyl}-benzoic acid methyl ester (202 mg). $^1$H NMR (CDCl$_3$) δ 7.92 (d, 2H), 7.18 (d, 2H), 6.73 (d, 1H), 6.60 (m, 3H), 6.15 (d, 1H), 5.91 (s, 2H), 4.08 (m, 1H), 3.87 (s, 3H), 3.68 (s, 2H), 3.56 (m, 1H), 2.79 (m, 1H), 2.59 (t, 2H), 2.34 (m, 2H), 2.14 (m, 1H), 1.72 (m, 3H); MS 450.1 (M+1).

Step B: 4-{3-[2R-(4-Benzo[1,3]dioxol-5-yl-3-hydroxy-but-1-enyl)-5-oxo-pyrrolidin-1-yl]-propyl}-benzoic acid methyl ester. Analogous to the procedure described for Compound 2B, Step C, 4-{3-[2R-(4-benzo[1,3]dioxol-5-yl-3-oxo-but-1-enyl)-5-oxo-pyrrolidin-1-yl]-propyl}-benzoic acid methyl ester (202 mg, 0.449 mmol) was reacted with NaBH$_4$ (17 mg, 0.45 mmol) in MeOH (8 mL) at 0° C. over 2 h. Purification by medium pressure chromatography (EtOAc to 2% MeOH in CH$_2$Cl$_2$) provided 4-{3-[2R-(4-benzo[1,3]dioxol-5-yl-3-hydroxy-but-1-enyl)-5-oxo-pyrrolidin-1-yl]-propyl}-benzoic acid methyl ester (156 mg). $^1$H NMR (CDCl$_3$) δ 7.94 (d, 2H), 7.23 (d, 2H), 6.67 (m, 3H), 5.92 (s, 2H), 5.66 (m, 1H), 5.45 (m, 1H), 4.28 (m, 1H), 3.99 (m, 1H), 3.87 (s, 3H), 3.55 (m, 1H), 2.88-2.59 (m, 5H), 2.50-1.61 (m, 7H); MS 452.1 (M+1).

Step C: 4-{3-[2R-(4-Benzo[1,3]dioxol-5-yl-3-hydroxy-but-1-enyl)-5-oxo-pyrrolidin-1-yl]-propyl}-benzoic acid. Analogous to the procedure described for Compound 2A, Step E, 4-{3-[2R-(4-benzo[1,3]dioxol-5-yl-3-hydroxy-but-1-enyl)-5-oxo-pyrrolidin-1-yl]-propyl}-benzoic acid methyl ester (156 mg, 0.345 mmol) was hydrolyzed with 2N NaOH in MeOH (5 mL) to provide the title compound of Example 2E (120 mg). $^1$H NMR (CDCl$_3$) δ 7.99 (d, 2H), 7.26 (m, 2H), 6.74 (d, 1H), 6.63 (m, 2H), 5.91 (s, 2H), 5.67 (m 1H), 5.46 (m, 1H), 4.29 (m, 1H), 3.99 (m, 1H), 3.57 (m, 1H), 2.94-2.60 (m, 5H), 2.36 (m, 2H), 2.14 (m, 1H), 1.87-1.62 (m, 4H); MS 436.2 (M−1).

Compound 2F

4-{3-[2S-(4-Benzo[1,3]dioxol-5-yl-3-hydroxy-butyl)-5-oxo-pyrrolidin-1-yl]-propyl}-benzoic acid Step A: 4-{3-[2S-(4-Benzo[1,3]dioxol-5-yl-3-hydroxy-butyl)-5-oxo-pyrrolidin-1-yl]-propyl}-benzoic acid. Analogous to the procedure described for Compound 2A, Step D, 4-{3-[2R-(4-benzo[1,3]dioxol-5-yl-3-hydroxy-but-1-enyl)-5-oxo-pyrrolidin-1-yl]-propyl}-benzoic acid (116 mg, 0.265 mmol) was hydrogenated to provide 4-{3-[2S-(4-benzo[1,3]dioxol-5-yl-3-hydroxy-butyl)-5-oxo-pyrrolidin-1-yl]-propyl}-benzoic acid (101 mg). $^1$H NMR (CDCl$_3$) δ 7.99 (d, 2H), 7.26 (m, 2H), 6.74 (d, 1H), 6.63 (m, 2H), 5.91 (s, 2H), 5.68 (m, 1H), 5.46 (m, 1H), 4.29 (m, 1H), 3.99 (m, 1H), 3.56 (m, 1H), 2.91 (m, 4H), 2.84-2.60 (m, 4H), 2.36 (m, 2H), 2.14 (m, 1H), 1.87-1.62 (m, 4H); MS 438.2 (M−1).

Compound 2G

7-{2S-[3R-Hydroxy-4-(3-trifluoromethoxy-phenyl)-butyl]-5-oxo-pyrrolidin-1-yl}-heptanoic acid Step A: 7-{2-Oxo-5R-[3-oxo-4-(3-trifluoromethoxy-phenyl)-but-1-enyl]-pyrrolidin-1-yl}-heptanoic acid ethyl ester. Analogous to the procedure described for Compound 2A, Step B, the anion derived from [2-oxo-3-(3-trifluoromethoxy-phenyl)-propyl]-phosphonic acid dimethyl ester (370 mg, 1.13 mmol) and NaH (60% in oil, 45 mg, 1.13 mmol) was reacted with 7-(2R-formyl-5-oxo-pyrrolidin-1-yl)-heptanoic acid ethyl ester (assumed 1.13 mmol) over 16 h. Medium pressure chromatography (19:1 hexanes:EtOAc to 6:4 hexanes:EtOAc to 1:1 hexanes:EtOAc to EtOAc) provided 7-{2-oxo-5R-[3-oxo-4-(3-trifluoromethoxy-phenyl)-but-1-enyl]-pyrrolidin-1-yl}-heptanoic acid ethyl ester (132 mg). $^1$H NMR (CDCl$_3$) δ 7.35 (m, 1H), 7.12 (m, 2H), 7.05 (s, 1H), 6.66 (dd, 1H), 6.21 (d, 1H), 4.18 (m, 1H), 4.10 (q, 2H), 3.86 (s, 2H), 3.54 (m, 1H), 2.70 (m, 1H), 2.47-2.22 (m, 5H), 1.78 (m, 1H), 1.57 (m, 2H), 1.61-1.21 (m, 9H); MS 470.2 (M+1), 468.1 (M−1).

Step B: 7-{2R-[3S-Hydroxy-4-(3-trifluoromethoxy-phenyl)-but-1-enyl]-5-oxo-pyrrolidin-1-yl}-heptanoic acid ethyl ester. To a solution of 7-{2-oxo-5R-[3-oxo-4-(3-trifluoromethoxy-phenyl)-but-1-enyl]-pyrrolidin-1-yl}-heptanoic acid ethyl ester (169 mg, 0.360 mmol) and (R)-2-methyl-CBS-oxazaborolidine (1M in toluene, 0.054 mL, 0.054 mmol) in CH$_2$Cl$_2$ (25.0 mL) at −45° C. was added catecholborane (1M in THF, 1.08 mL, 1.08 mmol) dropwise. The reaction mixture was stirred at −45° C. for 19 h. methanol (5 mL) was added and the reaction mixture was warmed to room temperature and was concentrated in vacuo. The residue was dissolved in CHCl$_3$ and the organic solution was washed with 1M NaOH (4×10 mL), 1M HCl (1×10 mL), and water (1×10 mL). The organic solution was dried (MgSO$_4$), filtered and concentrated. Purification by medium pressure chromatography (9:1 hexanes:EtOAc to 1:1 hexanes:EtOAc to EtOAc) provided 7-{2R-[3S-hydroxy-4-(3-trifluoromethoxy-phenyl)-but-1-enyl]-5-oxo-pyrrolidin-1-yl}-heptanoic acid ethyl ester (90 mg) as a 9:1 mixture (3S:3R) of alcohol diastereomers by HPLC analysis. $^1$H NMR (CDCl$_3$) δ 7.32 (m, 1H), 7.10 (m, 3H), 5.70 (dd, 1H), 5.50 (dd, 1H), 4.41 (m, 1H), 4.09 (q, 2H), 4.01 (m, 1H), 3.45 (m, 1H), 2.85 (d, 2H), 2.70 (m, 1H), 2.41-2.24 (m, 4H), 2.17 (m, 1H), 1.71-1.54 (m, 5H), 1.47-1.21 (m, 8H); MS 472.3 (M+1), 470.2 (M−1).

Step C: 7-{2S-[3R-Hydroxy-4-(3-trifluoromethoxy-phenyl)-butyl]-5-oxo-pyrrolidin-1-yl}-heptanoic acid ethyl ester. Analogous to the procedure described for Compound 2A, Step D, a solution of 7-{2R-[3S-hydroxy-4-(3-trifluoromethoxy-phenyl)-but-1-enyl]-5-oxo-pyrrolidin-1-yl}-heptanoic acid ethyl ester (86 mg, 0.182 mmol) in EtOH (40 mL) was hydrogenated in the presence of 10% palladium on carbon (50 mg) at 50 psi for 2.5 h. Purification by medium pressure chromatography (9:1 hexanes:EtOAc to 1:1 hexanes:EtOAc to EtOAc) provided 7-{2S-[3R-hydroxy-4-(3-trifluoromethoxy-phenyl)-butyl]-5-oxo-pyrrolidin-1-yl}-heptanoic acid ethyl ester (49 mg). $^1$H NMR (CDCl$_3$) δ 7.33 (m, 1H), 7.11 (m, 3H), 4.09 (q, 2H), 3.84 (m, 1H), 3.59 (m, 2H), 2.85 (m, 2H), 2.72 (m, 1H), 2.42-2.24 (m, 4H), 2.10 (m, 1H), 1.79 (m, 1H), 1.68-1.21 (m, 16H); MS 474.2 (M+1).

Step D: 7-{2S-[3R-Hydroxy-4-(3-trifluoromethoxy-phenyl)-butyl]-5-oxo-pyrrolidin-1-yl}-heptanoic acid. Analogous to the procedure described for Compound 2A, Step E, 7-{2S-[3R-hydroxy-4-(3-trifluoromethoxy-phenyl)-butyl]-5-oxo-pyrrolidin-1-yl}-heptanoic acid ethyl ester (45 mg, 0.095 mmol) was hydrolyzed with 1M NaOH (0.95 mL) in MeOH (20 mL) under reflux over 4 h to provide the title compound of Example 2G (35 mg). $^1$H NMR (CDCl$_3$) δ 7.33 (m, 1H), 7.10 (m, 3H), 3.86 (m, 1H), 3.58 (m, 2H), 2.90 (m, 1H), 2.81 (m, 1H), 2.73 (m, 1H), 2.34 (m, 4H), 2.10 (m, 1H), 1.80 (m, 1H), 1.66-1.24 (m, 13H); MS 446.3 (M+1), 444.2 (M−1).

Compound 2H

7-{2S-[4-(3-Cyano-phenyl)-3R-hydroxy-butyl]-5-oxo-pyrrolidin-1-yl}-heptanoic acid Step A: 7-{2R-[4-(3-Bromo-phenyl)-3-oxo-but-1-enyl]-5-oxo-pyrrolidin-1-yl}-heptanoic acid ethyl ester. Analogous to the procedure described for Compound 2A, Step B, the anion derived from [3-(3-bromo-phenyl)-2-oxo-propyl]-phosphonic acid dimethyl ester (2.90 g, 9.03 mmol) and NaH (60% in oil, 489 mg, 12.23 mmol) was reacted with 7-(2R-formyl-5-oxo-pyrrolidin-1-yl)-heptanoic acid ethyl ester (assumed 11.06 mmol) over 24 h. Flash chromatography (EtOAc to 5% MeOH in EtOAc) provided 7-{2R-[4-(3-bromo-phenyl)-3-oxo-but-1-enyl]-5-oxo-pyrrolidin-1-yl}-heptanoic acid ethyl ester (2.63 g). $^1$H NMR (CDCl$_3$) δ 7.40 (d, 1H), 7.35 (s, 1H), 7.20 (m, 1H), 7.12 (d, 1H), 6.66 (dd, 1H), 6.21 (d, 1H), 4.17 (m, 1H), 4.11 (q, 2H), 3.81 (s, 2H), 3.54 (m, 1H), 2.71 (m, 1H), 2.48-2.21 (m, 5H), 1.79 (m, 1H), 1.58 (m, 2H), 1.47-1.20 (m, 9H); MS 466.1 (M+1).

Step B: 7-{2R-[4-(3-Bromo-phenyl)-3S-hydroxy-but-1-enyl]-5-oxo-pyrrolidin-1-yl}-heptanoic acid ethyl ester. To a solution of 7-{2R-[4-(3-bromo-phenyl)-3-oxo-but-1-enyl]-5-oxo-pyrrolidin-1-yl}-heptanoic acid ethyl ester (2.63 g, 5.66 mmol) and (R)-2-methyl-CBS-oxazaborolidine (1M in toluene, 0.85 mL, 0.85 mmol) in CH$_2$Cl$_2$ (225 mL) at −45° C. was added catecholborane (1M in THF, 17.0 mL, 17.0 mmol) dropwise. The reaction mixture was stirred at −45° C. for 17 h. Aqueous HCl (1N, 17 mL) was added and the reaction mixture was warmed to room temperature. The organic solution was washed consecutively with 1N HCl (1×100 mL), water (2×100 mL) and brine (1×100 mL). The organic solution was dried (MgSO$_4$), filtered and concentrated. Purification by flash chromatography (EtOAc to 5% MeOH in EtOAc) provided 7-{2R-[4-(3-bromo-phenyl)-3S-hydroxy-but-1-enyl]-5-oxo-pyrrolidin-1-yl}-heptanoic acid ethyl ester (705 mg) as an approximate 95:5 ratio of 3S:3R alcohol diastereomers by $^1$H NMR. $^1$H NMR (CDCl$_3$) δ 7.36 (m, 2H), 7.15 (m, 2H), 5.70 (dd, 1H), 5.48 (dd, 1H), 4.40 (m, 1H), 4.10 (q, 2H), 4.03 (m, 1H), 3.46 (m, 1H), 2.81 (d, 2H), 2.72 (m, 1H), 2.39 (m, 2H), 2.27 (t, 2H), 2.20 (m, 1H), 1.84-1.22 (m, 13H).

Step C: 7-{2R-[4-(3-Cyano-phenyl)-3S-hydroxy-but-1-enyl]-5-oxo-pyrrolidin-1-yl}-heptanoic acid ethyl ester. Nitrogen was bubbled into a solution of 7-{2R-[4-(3-bromo-phenyl)-3S-hydroxy-but-1-enyl]-5-oxo-pyrrolidin-1-yl}-heptanoic acid ethyl ester (700 mg, 1.50 mmol) in DMF (2.6 mL) for 5 minutes. Zinc cyanide (108 mg, 0.92 mmol) and tetrakis(triphenylphosphine)palladium(0) (58 mg, 0.05 mmol) were added and nitrogen was bubbled into the reaction mixture for 5 minutes. The reaction mixture was heated at 105° C. for 24 h. Additional tetrakis(triphenylphosphine)palladium(0) (58 mg, 0.050 mmol) was added and heating was continued for 1.5 h. The reaction mixture was poured into water (50 mL) and the aqueous solution was washed with Et$_2$O (3×50 mL). The combined ethereal layers were dried (MgSO$_4$), filtered and concentrated in vacuo. Medium pressure chromatography (EtOAc to 5% MeOH in EtOAc to 10% MeOH in EtOAc) provided 7-{2R-[4-(3-cyano-phenyl)-3S-hydroxy-but-1-enyl]-5-oxo-pyrrolidin-1-yl}-heptanoic acid ethyl ester (323 mg). $^1$H NMR (CDCl$_3$) δ7.53 (m, 2H), 7.48-7.39 (m, 2H), 5.72 (dd, 1H), 5.51 (dd, 1H), 4.41 (m, 1H), 4.10 (q, 2H), 4.03 (m, 1H), 3.46 (m, 1H), 2.86 (m, 2H), 2.73 (m, 1H), 2.36 (m, 2H), 2.27 (t, 2H), 2.20 (m, 1H), 1.71-1.22 (m, 13H); MS 413.3 (M+1).

Step D: 7-{2S-[4-(3-Cyano-phenyl)-3R-hydroxy-butyl]-5-oxo-pyrrolidin-1-yl}-heptanoic acid ethyl ester. Analogous to the procedure described for Compound 2A, Step D, a solution of 7-{2R-[4-(3-cyano-phenyl)-3S-hydroxy-but-1-enyl]-5-oxo-pyrrolidin-1-yl}-heptanoic acid ethyl ester (150 mg, 0.36 mmol) in EtOH (13 mL) was hydrogenated in the presence of 10% palladium on carbon (16 mg) at 45 psi for 3.5 h to provide 7-{2S-[4-(3-cyano-phenyl)-3R-hydroxy-butyl]-5-oxo-pyrrolidin-1-yl}-heptanoic acid ethyl ester (150 mg). $^1$H NMR (CDCl$_3$) δ 7.54 (m, 2H), 7.44 (m, 2H), 4.09 (q, 2H), 3.84 (m, 1H), 3.60 (m, 2H), 2.95-2.71 (m, 3H), 2.36 (m, 2H), 2.27 (t, 2H), 2.11 (m, 1H), 1.79 (m, 1H), 1.68-1.20 (m, 16H); MS 415.2 (M+1).

Step E: 7-{2S-[4-(3-Cyano-phenyl)-3R-hydroxy-butyl]-5-oxo-pyrrolidin-1-yl}-heptanoic acid. Analogous to the procedure described for Compound 2A, Step E, 7-{2S-[4-(3-cyano-phenyl)-3R-hydroxy-butyl]-5-oxo-pyrrolidin-1-yl}-heptanoic acid ethyl ester (150 mg, 0.36 mmol) was hydrolyzed with 5M NaOH (3 mL) in EtOH (5 mL) at room temperature over 24 h to provide the title compound of Example 2H (119 mg). $^1$H NMR (CDCl$_3$) δ 7.52 (m, 2H), 7.43 (m, 2H), 3.84 (m, 1H), 3.56 (m, 2H), 2.93-2.70 (m, 3H), 2.32 (m, 4H), 2.09 (m, 1H), 1.78 (m, 1H), 1.65-1.21 (m, 13H); MS 387.2 (M×1).

Compound 2I 7-(2S-{3R-Hydroxy-4-[3-(2-methoxy-ethyl)-phenyl]-butyl}-5-oxo-pyrrolidin-1-yl)-heptanoic acid Step A: 7-(2R-{4-[3-(2-Methoxy-ethyl)-phenyl]-3-oxo-but-1-enyl}-5-oxo-pyrrolidin-1-yl)-heptanoic acid ethyl ester. Analogous to the procedure described for Compound 2A, Step B, the anion derived from {3-[3-(2-methoxy-ethyl)-phenyl]-2-oxo-propyl}-phosphonic acid diethyl ester (130 mg, 0.396 mmol) and NaH (60% in oil, 17 mg, 0.425 mmol) was reacted with 7-(2R-formyl-5-oxo-pyrrolidin-1-yl)-heptanoic acid ethyl ester (assumed 0.461 mmol) over 24 h. Medium pressure chromatography (50% EtOAc in hexanes to EtOAc) provided 7-(2R-{4-[3-(2-methoxy-ethyl)-phenyl]-3-oxo-but-1-enyl}-5-oxo-pyrrolidin-1-yl)-heptanoic acid ethyl ester (101 mg). $^1$H NMR (CDCl$_3$) δ 7.23 (m, 1H), 7.11 (m, 1H), 7.02 (m, 2H), 6.62 (dd, 1H), 6.20 (d, 1H), 4.12 (m, 3H), 3.80 (s, 2H), 3.56 (t, 2H), 3.51 (m, 1H), 3.32 (s, 3H), 2.84 (t, 2H), 2.68 (m, 1H), 2.37 (m, 2H), 2.24 (m, 3H), 1.75 (m, 1H), 1.56 (m, 2H), 1.42-1.17 (m, 9H); MS 444.2 (M+1).

Step B: 7-(2R-{3S-Hydroxy-4-[3-(2-methoxy-ethyl)-phenyl]-but-1-enyl}-5-oxo-pyrrolidin-1-yl)-heptanoic acid ethyl ester. To a solution of 7-(2R-{4-[3-(2-methoxy-ethyl)-phenyl]-3-oxo-but-1-enyl}-5-oxo-pyrrolidin-1-yl)-heptanoic acid acid ethyl ester (88 mg, 0.198 mmol) and (R)-2-methyl-CBS-oxazaborolidine (1M in toluene, 0.200 mL, 0.200 mmol) in CH$_2$Cl$_2$ (10 mL) at −45° C. was added catecholborane (1M in THF, 0.60 mL, 0.60 mmol) dropwise. The reaction mixture was stirred at −45° C. for 24 h. Aqueous HCl (1N, 10 mL) was added and the reaction mixture was warmed to room temperature and was stirred for 1.5 h. The organic solution was washed with cold 1N NaOH (3×15 mL) followed by brine (1×20 mL). The organic solution was dried (MgSO$_4$), filtered and concentrated. Purification by medium pressure chromatography (50% EtOAc in hexanes to 75% EtOAc in hexanes to EtOAc) provided 7-(2R-{3S-hydroxy-4-[3-(2-methoxy-ethyl)-phenyl]-but-1-enyl}-5-oxo-pyrrolidin-1-yl)-heptanoic acid ethyl ester (45 mg) as an approximate 4:1 mixture of 3S:3R alcohol diasteromers by $^1$H NMR. $^1$H NMR (CDCl$_3$) δ 7.22 (m, 1H), 7.09 (m, 1H), 7.04 (m, 2H), 5.72 (dd, 1H), 5.49 (dd, 1H), 4.38 (m, 1H), 4.10 (q, 2H), 4.02 (m, 1H), 3.58 (t, 2H), 3.46 (m, 1H), 3.34 (s, 3H), 2.87-2.68 (m, 5H), 2.41-2.24 (m, 4H), 2.18 (m, 1H), 1.70 (m, 2H), 1.59 (m, 2H), 1.48-1.21 (m, 9H); MS 446.4 (M+1).

Step C: 7-(2S-{3R-Hydroxy-4-[3-(2-methoxy-ethyl)-phenyl]-butyl}-5-oxo-pyrrolidin-1-yl)-heptanoic acid ethyl ester. Analogous to the procedure described for Compound 2A, Step D, a solution of 7-(2R-{3S-hydroxy-4-[3-(2-methoxy-ethyl)-phenyl]-but-1-enyl}-5-oxo-pyrrolidin-1-yl)-heptanoic acid ethyl ester (43 mg, 0.0965 mmol) in EtOH (20 mL) was hydrogenated in the presence of 10% palladium on carbon (20 mg) at 50 psi for 18 h. Purification by medium pressure chromatography (50% EtOAc in hexanes to EtOAc to 10% MeOH in CH$_2$Cl$_2$) provided 7-(2S-{3R-hydroxy-4-[3-(2-methoxy-ethyl)-phenyl]-butyl}-5-oxo-pyrrolidin-1-yl)-heptanoic acid ethyl ester (16 mg). MS 448.3 (M+1).

Step D: 7-(2S-{3R-Hydroxy-4-[3-(2-methoxy-ethyl)-phenyl]-butyl}-5-oxo-pyrrolidin-1-yl)-heptanoic acid. Analogous to the procedure described for Compound 2A, Step E, 7-(2S-{3R-hydroxy-4-[3-(2-methoxy-ethyl)-phenyl]-butyl}-5-oxo-pyrrolidin-1-yl)-heptanoic acid ethyl ester (15 mg, 0.034 mmol) was hydrolyzed with 6M NaOH (0.20 mL) in EtOH (0.50 mL) at room temperature over 18 h to provide the title compound, Compound 2I (14 mg). $^1$H NMR (CDCl$_3$) δ 7.22 (m, 1H), 7.05 (m, 3H), 3.82 (m, 1H), 3.56 (m, 4H), 3.32 (s, 3H), 2.93-2.82 (m, 3H), 2.76 (m, 1H), 2.62 (m, 1H), 2.42-2.25 (m, Compound 2J 7-{2R-[3-Hydroxy-4-(3-phenoxy-phenyl)-but-1-enyl]-5-oxo-pyrrolidin-1-yl}-heptanoic acid Step A: 7-{2-Oxo-5R-[3-oxo-4-(3-phenoxy-phenyl)-but-1-enyl]-pyrrolidin-1-yl}-heptanoic acid ethyl ester. Analogous to the procedure described for Compound 2A, Step B, the anion derived from [2-oxo-3-(3-phenoxy-phenyl)-propyl]-phosphonic acid dimethyl ester (633 mg, 1.98 mmol) and NaH (60% in oil, 70 mg, 1.74 mmol) was reacted with 7-(2R-formyl-5-oxo-pyrrolidin-1-yl)-heptanoic acid ethyl ester (assumed 1.58 mmol) over 24 h. Medium pressure chromatography (EtOAc) provided 7-{2-oxo-5R-[3-oxo-4-(3-phenoxy-phenyl)-but-1-enyl]-pyrrolidin-1-yl}-heptanoic acid ethyl ester (215 mg). $^1$H NMR (CDCl$_3$) δ 7.28 (m, 3H), 7.08 (m, 1H), 6.97 (m, 2H), 6.89 (m, 2H), 6.83 (m, 1H), 6.62 (dd, 1H), 6.19 (d, 1H), 4.13 (m, 1H), 4.08 (q, 2H), 3.79 (s, 2H), 3.51 (m, 1H), 2.68 (m, 1H), 2.35 (m, 2H), 2.24 (m, 3H), 2.24 (m, 3H), 1.75 (m, 1H), 1.54 (m, 2H), 1.43-1.20 (m, 9H).

Step B: 7-{2R-[3-hydroxy-4-(3-phenoxy-phenyl)-but-1-enyl]-5-oxo-pyrrolidin-1-yl}-heptanoic acid ethyl ester. Analogous to the procedure described for Compound 2B, Step C, 7-{2-oxo-5R-[3-oxo-4-(3-phenoxy-phenyl)-but-1-enyl]-pyrrolidin-1-yl}-heptanoic acid ethyl ester (215 mg, 0.451 mmol) was reacted with NaBH$_4$ (17 mg, 0.45 mmol) in EtOH (3 mL) at 0° C. over 4 h. Purification by medium pressure chromatography (EtOAc) provided 7-{2R-[3-hydroxy-4-(3-phenoxy-phenyl)-but-1-enyl]-5-oxo-pyrrolidin-1-yl}-heptanoic acid ethyl ester (167 mg). $^1$H NMR (CDCl$_3$) δ 7.33 (m, 2H), 7.25 (m, 1H), 7.10 (m, 1H), 6.99 (m, 2H), 6.93 (m, 1H), 6.86 (m, 2H), 5.72 (m, 1H), 5.45 (m, 1H), 4.37 (m, 1H), 4.10 (q, 2H), 3.47 (m, 1H), 2.82 (m, 3H), 2.35 (m, 2H), 2.26 (t, 2H), 2.15 (m, 1H), 1.70-1.21 (m, 13H).

Step C: 7-{2R-[3-Hydroxy-4-(3-phenoxy-phenyl)-but-1-enyl]-5-oxo-pyrrolidin-1-yl}-heptanoic acid. Analogous to the procedure described for Compound 2A, Step E, 7-{2R-[3-hydroxy-4-(3-phenoxy-phenyl)-but-1-enyl]-5-oxo-pyrrolidin-1-yl}-heptanoic acid ethyl ester (29 mg, 0.060 mmol) was hydrolyzed with 2M NaOH in EtOH (4.0 mL) at room temperature over 24 h to provide the title compound of Example 2J (20 mg). $^1$H NMR (CDCl$_3$) δ 7.33-7.21 (m, 3H), 7.08 (m, 1H), 6.98-6.84 (m, 5H), 5.70 (m, 1H), 5.44 (m, 1H), 4.36 (m, 1H), 4.00 (m, 1H), 3.44 (m, 1H), 2.85-2.51 (m, 3H), 2.32 (m, 4H), 2.14 (m, 1H), 1.68-1.18 (m, 10H).

Compound 2K

7-{2S-[3-Hydroxy-4-(3-phenoxy-phenyl)-butyl]-5-oxo-pyrrolidin-1-yl}-heptanoic acid Step A: 7-{2S-[3-Hydroxy-4-(3-phenoxy-phenyl)-butyl]-5-oxo-pyrrolidin-1-yl}-heptanoic acid ethyl ester. Analogous to the procedure described for Compound 2A, Step D, a mixture of 7-{2R-[3-hydroxy-4-(3-phenoxy-phenyl)-but-1-enyl]-5-oxo-pyrrolidin-1-yl}-heptanoic acid ethyl ester (139 mg, 0.290 mmol), MeOH (30 mL), and 10% palladium on carbon (14 mg) was hydrogenated on a Parr shaker at 50 psi for 18 h. Purification by medium pressure chromatography (1:1 hexanes:EtOAc) provided 7-{2S-[3-hydroxy-4-(3-phenoxy-phenyl)-butyl]-5-oxo-pyrrolidin-1-yl}-heptanoic acid ethyl ester (86 mg). $^1$H NMR (CDCl$_3$) δ 7.35-7.24 (m, 3H), 7.10 (m, 1H), 6.99 (m, 2H), 6.93 (m, 1H), 6.87 (m, 2H), 4.09 (q, 2H), 3.80 (m, 1H), 2H), 2.82 (m, 2H), 2.64 (m, 1H), 2.42-2.24 (m, 4H), 2.10 (m, 1H), 1.77 (m, 1H), 1.66-1.21 (m, 16H).

Step B: 7-{2S-[3-Hydroxy-4-(3-phenoxy-phenyl)-butyl]-5-oxo-pyrrolidin-1-yl}-heptanoic acid. Analogous to the procedure described for Compound 2A, Step E, 7-{2S-[3-hydroxy-4-(3-phenoxy-phenyl)-butyl]-5-oxo-pyrrolidin-1-yl}-heptanoic acid ethyl ester (86 mg, 1.79 mmol) was hydrolyzed with 2N NaOH in MeOH (4 mL) over 18 h to provide the title compound of Example 2K (62 mg). $^1$H NMR (CDCl$_3$) δ 7.33-7.23 (m, 3H), 7.09 (m, 1H), 6.98 (m, 2H), 6.91 (m, 1H), 6.86 (m, 2H), 3.80 (m, 1H), 3.56 (m, 2H), 2.88 (m, 1H), 2.77 (m, 1H), 2.64 (m, 1H), 2.38-2.28 (m, 4H), 2.09 (m, 1H), 1.77 (m, 1H), 1.64-1.21 (m, 13H).

Compound 3A

5-{3-[2S-(3-Hydroxy-4-thiophen-2-yl-butyl)-5-oxo-pyrrolidin-1-yl]-propyl}-thiophene-2-carboxylic acid Step A: 5-{3-[2-Oxo-5R-(3-oxo-4-thiophen-2-yl-but-1-enyl)-pyrrolidin-1-yl]-propyl}-thioihene-2-carboxylic acid methyl ester. Analogous to the procedure described for Compound 2A, Step B, the anion derived from (2-oxo-3-thiophen-2-yl-propyl)-phosphonic acid dimethyl ester (101 mg, 0.407 mmol) and NaH (60% by weight in oil, 16 mg, 0.41 mmol) was reacted with 5-[3-(2R-formyl-5-oxo-pyrrolidin-1-yl)- propyl]-thiophene-2-carboxylic acid methyl ester (prepared from 5-[3-(2R-hydroxymethyl-5-oxo-pyrrolidin-1-yl)-propyl]-thiophene-2-carboxylic acid methyl ester analogous to the procedure described for Compound 2A, Step A) (assumed 0.34 mmol) over 17 h. Purification by medium pressure chromatography (1:1 hexanes:EtOAc to EtOAc) provided 5-{3-[2-oxo-5R-(3-oxo-4-thiophen-2-yl-but-1-enyl)-pyrrolidin-1-yl]-propyl}-thiophene-2-carboxylic acid methyl ester (74 mg). $^1$H NMR (CDCl$_3$) δ 7.60 (d, 1H), 7.21 (m, 1H), 6.96 (m, 1H), 6.88 (m, 1H), 6.78 (d, 1H), 6.65 (dd, 1H), 6.23 (d, 1H), 4.14 (m, 1H), 4.01 (s, 2H), 3.84 (s, 3H), 3.58 (m, 1H), 2.88-2.77 (m, 3H), 2.46-2.17 (m, 3H), 1.82 (m, 3H); MS 418.0 (M+1), 416.0 (M−1).

Step B: 5-{3-[2-Oxo-5S-(3-oxo-4-thiophen-2-yl-butyl)-pyrrolidin-1-yl]-propyl}-thiophene-2-carboxylic acid methyl ester. Analogous to the procedure described for Compound 2A, Step D, 5-{3-[2-oxo-5R-(3-oxo-4-thiophen-2-yl-but-1-enyl)-pyrrolidin-1-yl]-propyl}-thiophene-2-carboxylic acid methyl ester (71 mg, 0.17 mmol) was hydrogenated in EtOH (20 mL) in the presence of 10% palladium on carbon (50 mg) at 50 psi for 2 h. Additional catalyst was added (50 mg) and the reaction mixture was hydrogenated at 50 psi for an additional 1 h to provide 5-{3-[2-oxo-5S-(3-oxo-4-thiophen-2-yl-butyl)-pyrrolidin-1-yl]-propyl}-thiophene-2-carboxylic acid methyl ester (63 mg). $^1$H NMR (CDCl$_3$) δ 7.61 (d, 1H), 7.22 (m, 1H), 6.97 (m, 1H), 6.88 (m, 1H), 6.80 (d, 1H), 3.88 (s, 2H), 3.84 (s, 3H), 3.65 (m, 1H), 3.52 (m, 1H), 2.95 (m, 1H), 2.81 (t, 2H), 2.48 (m, 1H), 2.30 (m, 2H), 2.07-1.80 (m, 4H), 1.55 (m, 3H); MS 419.9 (M+1), 418.0 (M−1).

Step C: 5-{3-[2S-(3-Hydroxy-4-thiophen-2-yl-butyl)-5-oxo-pyrrolidin-1-yl]-propyl}-thiophene-2-carboxylic acid methyl ester. Analogous to the procedure described for Compound 2B, Step C, 5-{3-[2-oxo-5S-(3-oxo-4-thiophen-2-yl-butyl)-pyrrolidin-1-yl]-propyl}-thiophene-2-carboxylic acid methyl ester (60 mg, 0.143 mmol) was reduced with NaBH$_4$ (5 mg, 0.132 mmol) over 2 h. Purification by preparative thin layer chromatography (EtOAc) provided 5-{3-[2S-(3-hydroxy-4-thiophen-2-yl-butyl)-5-oxo-pyrrolidin-1-yl]-propyl}-thiophene-2-carboxylic acid methyl ester (10 mg). $^1$H NMR (CDCl$_3$) δ 7.61 (d, 1H), 7.18 (d, 1H), 6.96 (m, 1H), 6.85 (d, 1H), 6.81 (d, 1H), 3.83 (s, 3H), 3.80 (m, 1H), 3.61 (m, 2H), 3.00 (m, 2H), 2.89 (m, 1H), 2.83 (t, 2H), 2.34 (m, 2H), 2.10 (m, 1H), 1.98-1.23 (m, 8H); MS 422.2 (M+1).

Step D: 5-{3-[2S-(3-Hydroxy-4-thiophen-2-yl-butyl)-5-oxo-pyrrolidin-1-yl]-propyl}-thiophene-2-carboxylic acid. Analogous to the procedure described for Compound 2A, Step E, 5-{3-[2S-(3-hydroxy-4-thiophen-2-yl-butyl)-5-oxo-pyrrolidin-1-yl]-propyl}-thiophene-2-carboxylic acid methyl ester (10 mg, 0.024 mmol) was hydrolyzed with NaOH (1M, 0.03 mL) in MeOH (5 mL) over 29 h to provide the title compound, Compound 3A (10 mg). $^1$H NMR (CDCl$_3$) δ 7.68 (d, 1H), 7.18 (m, 1H), 6.96 (m, 1H), 6.85 (m, 2H), 3.80 (m, 1H), 3.63 (m, 2H), 3.01 (m, 2H), 2.91 (m, 1H), 2.85 (t, 2H), 2.36 (m, 2H), 2.11 (m, 1H), 2.00-1.18 (m, 8H).

Compound 3B 5-(3-{2S-[4-(4-Chloro-phenyl)-3-hydroxy-butyl]-5-oxo-pyrrolidin-1-yl}-propyl)-thiophene-2-carboxylic acid Step A: 5-(3-{2R-[4-(4-Chloro-phenyl)-3-oxo-but-1-enyl]-5-oxo-pyrrolidin-1-yl}-propyl)-thiophene-2-carboxylic acid methyl ester. Analogous to the procedure described for Compound 2A, Step B, the anion derived from [3-(4-chloro-phenyl)-2-oxo-propyl]-phosphonic acid dimethyl ester (113 mg, 0.407 mmol) and NaH (60% by weight in oil, 16 mg, 0.41 mmol) was reacted with 5-[3-(2R-formyl-5-oxo-pyrrolidin-1-yl)-propyl]-thiophene-2-carboxylic acid methyl ester (assumed 0.34 mmol) over 17 h. Purification by medium pressure chromatography (1:1 hexanes:EtOAc to EtOAc) provided 5-(3-{2R-[4-(4-chloro-phenyl)-3-oxo-but-1-enyl]-5-oxo-pyrrolidin-1-yl}-propyl)-thiophene-2-carboxylic acid methyl ester (94 mg). $^1$H NMR (CDCl$_3$) δ 7.61 (d, 1H), 7.29 (m, 2H), 7.10 (d, 2H), 6.78 (d, 1H), 6.62 (dd, 1H), 6.18 (d, 1H), 4.13 (m, 1H), 3.84 (s, 3H), 3.79 (s, 2H), 3.56 (m, 1H), 2.87-2.77 (m, 3H), 2.47-2.16 (m, 3H), 1.80 (m, 3H).

Step B: 5-(3-{2S-[4-(4-Chloro-phenyl)-3-oxo-butyl]-5-oxo-pyrrolidin-1-yl}-propyl)-thiophene-2-carboxylic acid methyl ester. Analogous to the procedure described for Compound 2A, Step D, 5-(3-{2R-[4-(4-chloro-phenyl)-3-oxo-but-1-enyl]-5-oxo-pyrrolidin-1-yl}-propyl)-thiophene-2-carboxylic acid methyl ester (91 mg, 0.204 mmol) was hydrogenated in EtOH (20 mL) in the presence of 10% palladium on carbon (50 mg) at 50 psi for 2 h to provide 5-(3-{2S-[4-(4-chloro-phenyl)-3-oxo-butyl]-5-oxo-pyrrolidin-1-yl}-propyl)-thiophene-2-carboxylic acid methyl ester (84 mg). $^1$H NMR (CDCl$_3$) δ 7.61 (d, 1H), 7.30 (d, 2H), 7.11 (d, 2H), 6.80 (d, 1H), 3.84 (s, 3H), 3.66 (s, 2H), 3.64 (m, 1H), 3.51 (m, 1H), 2.94 (m, 1H), 2.81 (t, 2H), 2.42 (m, 2H), 2.29 (m, 2H), 2.04-1.79 (m, 4H), 1.56 (m, 2H); MS 448.0 (M+1), 446.0 (M−1).

Step C: 5-(3-{2S-[4-(4-Chloro-phenyl)-3-hydroxy-butyl]-5-oxo-pyrrolidin-1-yl}-propyl)-thiophene-2-carboxylic acid methyl ester. Analogous to the procedure described for Compound 2B, Step C, 5-(3-{2S-[4-(4-chloro-phenyl)-3-oxo-butyl]-5-oxo-pyrrolidin-1-yl}-propyl)-thiophene-2-carboxylic acid methyl ester (81 mg, 0.181 mmol) was reduced with NaBH$_4$ (7 mg, 0.181 mmol) over 2 h. Purification by preparative thin layer chromatography (EtOAc, 2×) provided 5-(3-{2S-[4-(4-chloro-phenyl)-3-hydroxy-butyl]-5-oxo-pyrrolidin-1-yl}-propyl)-thiophene-2-carboxylic acid methyl ester (54 mg). $^1$H NMR (CDCl$_3$) δ 7.61 (d, 1H), 7.28 (d, 2H), 7.12 (d, 2H), 6.81 (d, 1H), 3.82 (s, 3H), 3.77 (m, 1H), 3.60 (m, 2H), 2.99 (m, 1H), 2.83 (t, 2H), 2.77 (m, 1H), 2.62 (m, 1H), 2.34 (m, 2H), 2.09 (m, 1H), 1.97-1.30 (m, 8H); MS 450.0 (M+1).

Step D: 5-(3-{2S-[4-(4-Chloro-phenyl)-3-hydroxy-butyl]-5-oxo-pyrrolidin-1-yl}-propyl)-thiophene-2-carboxylic acid. Analogous to the procedure described for Compound 2A, Step E, 5-(3-{2S-[4-(4-chloro-phenyl)-3-hydroxy-butyl]-5-oxo-pyrrolidin-1-yl}-propyl)-thiophene-2-carboxylic acid methyl ester (52 mg, 0.116 mmol) was hydrolyzed with NaOH (1M, 0.14 mL) in MeOH (5 mL) under reflux over 29 h to provide 5-(3-{2S-[4-(4-chloro-phenyl)-3-hydroxy-butyl]-5-oxo-pyrrolidin-1-yl}-propyl)-thiophene-2-carboxylic acid (16 mg). $^1$H NMR (CDCl$_3$) δ 7.67 (d, 1H), 7.28 (d, 2H), 7.12 (d, 2H), 6.84 (d, 1H), 3.78 (m, 1H), 3.62 (m, 1H), 3.01 (m, 1H), 2.85 (t, 2H), 2.77 (m, 1H), 2.63 (m, 1H), 2.36 (m, 2H), 2.10 (m, 1H), 1.90 (m, 3H), 1.75 (m, 1H), 1.69-1.24 (m, 4H); MS 434.0 (M−1).

Compound 3C 5-(3-{2S-[3-Hydroxy-4-(2-trifluoromethyl-phenyl)-butyl]-5-oxo-pyrrolidin-1-yl}-propyl)-thiophene-2-carboxylic acid Step A: 5-(3-{2-Oxo-5R-[3-oxo-4-(2-trifluoromethyl-phenyl)-but-1-enyl]-pyrrolidin-1-yl}-propyl)-thiophene-2-carboxylic acid methyl ester. Analogous to the procedure described for Compound 2A, Step B, the anion derived from [2-oxo-3-(2-trifluoromethyl-phenyl)-propyl]-phosphonic acid dimethyl ester (74 mg, 0.239 mmol) and NaH (60% by weight in oil, 10 mg, 0.239 mmol) was reacted with 5-[3-(2R-formyl-5-oxo-pyrrolidin-1-yl)-propyl]-thiophene-2-carboxylic acid methyl ester (assumed 0.239 mmol) over 17 h. Purification by medium pressure chromatography (1:1 hexanes:EtOAc to EtOAc) provided 5-(3-{2-oxo-5R-[3-oxo-4-(2-trifluoromethyl-phenyl)-but-1-enyl]-pyrrolidin-1-yl}-propyl)-thiophene-2-carboxylic acid methyl ester (32 mg). $^{1}$H NMR (CDCl$_{3}$) δ 7.66 (d, 1H), 7.60 (m, 1H), 7.51 (m, 1H), 7.39 (m, 1H), 7.28 (m, 1H), 6.79 (m, 1H), 6.64 (dd, 1H), 6.22 (d, 1H), 4.16 (m, 1H), 3.83 (s, 3H), 3.78 (s, 2H), 3.60 (m, 1H), 2.93-2.79 (m, 3H), 2.48-2.20 (m, 3H), 1.83 (m, 3H); MS 479.9 (M+1). 478.0 (M−1).

Step B: 5-(3-{2-Oxo-5S-[3-oxo-4-(2-trifluoromethyl-phenyl)-butyl]-pyrrolidin-1-yl}-propyl)-thiophene-2-carboxylic acid methyl ester. Analogous to the procedure described for Compound 2A, Step D, 5-(3-{2-oxo-5R-[3-oxo-4-(2-trifluoromethyl-phenyl)-but-1-enyl]-pyrrolidin-1-yl}-propyl)-thiophene-2-carboxylic acid methyl ester (29 mg, 0.060 mmol) was hydrogenated in EtOH (20 mL) in the presence of 10% palladium on carbon (40 mg) at 50 psi for 2 h to provide 5-(3-{2-oxo-5S-[3-oxo-4-(2-trifluoromethyl-phenyl)-butyl]-pyrrolidin-1-yl}-propyl)-thiophene-2-carboxylic acid methyl ester (29 mg). $^{1}$H NMR (CDCl$_{3}$) δ 7.66 (d, 1H), 7.59 (m, 1H), 7.52 (m, 1H), 7.39 (m, 1H), 7.27 (m, 1H), 6.80 (d, 1H), 3.83 (s, 3H), 3.78 (s, 2H), 3.64 (m, 1H), 3.55 (m, 1H), 2.97 (m, 1H), 2.81 (t, 2H), 2.48 (m, 1H), 2.33 (m, 2H), 2.05 (m, 2H), 1.87 (m, 2H), 1.56 (m, 3H); MS 482.0 (M+1), 480.0 (M−1).

Step C: 5-(3-{2S-[3-Hydroxy-4-(2-trifluoromethyl-phenyl)-butyl]-5-oxo-pyrrolidin-1-yl}-propyl)-thiophene-2-carboxylic acid methyl ester. Analogous to the procedure described for Compound 2B, Step C, 5-(3-{2-oxo-5S-[3-oxo-4-(2-trifluoromethyl-phenyl)-butyl]-pyrrolidin-1-yl}-propyl)-thiophene-2-carboxylic acid methyl ester (26 mg, 0.054 mmol) was reduced with NaBH$_{4}$ (2 mg, 0.054 mmol) over 2 h. Purification by preparative thin layer chromatography (EtOAc) provided 5-(3-{2S-[3-hydroxy-4-(2-trifluoromethyl-phenyl)-butyl]-5-oxo-pyrrolidin-1-yl}-propyl)-thiophene-2-carboxylic acid methyl ester (10 mg). $^{1}$H NMR (CDCl$_{3}$) δ 7.65 (d, 1H), 7.59 (m, 1H), 7.49 (m, 1H), 7.36 (m, 2H), 6.81 (d, 1H), 3.81 (s, 3H), 3.81 (m, 1H), 3.62 (m, 2H), 3.02 (m, 2H), 2.83 (t, 2H), 2.78 (m, 1H), 2.34 (m, 2H), 2.12 (m, 1H), 2.01-1.35 (m, 8H); MS 484.0 (M+1).

Step D: 5-(3-{2S-[3-Hydroxy-4-(2-trifluoromethyl-phenyl)-butyl]-5-oxo-pyrrolidin-1}-propyl)-thiophene-2-carboxylic acid. Analogous to the procedure described for Compound 2A, Step E, 5-(3-{2S-[3-hydroxy-4-(2-trifluoromethyl-phenyl)-butyl]-5-oxo-pyrrolidin-1-yl}-propyl)-thiophene-2-carboxylic acid methyl ester (10 mg, 0.0207 mmol) was hydrolyzed with NaOH (1M, 0.07 mL) in MeOH (5 mL) heated under reflux for 29 h to provide 5-(3-{2S-[3-hydroxy-4-(2-trifluoromethyl-phenyl)-butyl]-5-oxo-pyrrolidin-1-yl}-propyl)-thiophene-2-carboxylic acid (13 mg). $^{1}$H NMR (CDCl$_{3}$) δ 7.66 (m, 1H), 7.50 (m, 1H), 7.37 (m, 3H), 6.84 (d, 1H), 3.83 (m, 1H), 3.64 (m, 2H), 3.04 (m, 2H), 2.85 (t, 2H), 2.78 (m, 1H), 2.37 (m, 2H), 2.12 (m, 1H), 2.02-1.24 (m, 8H); MS 470.1 (M+1), 468.0 (M−1).

Compound 3D 5-(3-{2S-[4-(4-Fluoro-phenyl)-3-hydroxy-butyl]-5-oxo-pyrrolidin-1-yl}-propyl)-thiophene-2-carboxylic acid Step A: 5-(3-{2R-[4-(4-Fluoro-phenyl)-3-oxo-but-1-enyl]-5-oxo-pyrrolidin-1-yl}-propyl)-thiophene-2-carboxylic acid methyl ester. Analogous to the procedure described for Compound 2A, Step B, the anion derived from [3-(4-fluoro-phenyl)-2-oxo-propyl]-phosphonic acid dimethyl ester (106 mg, 0.407 mmol) and NaH (60% by weight in oil, 16 mg, 0.407 mmol) was reacted with 5-[3-(2R-formyl-5-oxo-pyrrolidin-1-yl)-propyl]-thiophene-2-carboxylic acid methyl ester (assumed 0.407 mmol) over 17 h. Purification by medium pressure chromatography (1:1 hexanes:EtOAc to EtOAc) provided 5-(3-{2R-[4-(4-fluoro-phenyl)-3-oxo-but-1-enyl]-5-oxo-pyrrolidin-1-yl}-propyl)-thiophene-2-carboxylic acid methyl ester (77 mg). $^{1}$H NMR (CDCl$_{3}$) δ (d, 1H), 7.16 (m, 2H), 7.00 (m, 2H), 6.77 (d, 1H), 6.62 (dd, 1H), 6.19 (d, 1H), 4.13 (m, 1H), 3.84 (s, 3H), 3.79 (s, 2H), 3.57 (m, 1H), 2.87-2.77 (m, 3H), 2.37 (m, 2H), 2.20 (m, 1H), 1.80 (m, 3H); MS 430.0 (M+1), 428.1 (M−1).

Step B: 5-(3-{2S-[4-(4-Fluoro-phenyl)-3-oxo-butyl]-5-oxo-pyrrolidin-1-yl}-propyl)-thiophene-2-carboxylic acid methyl ester. Analogous to the procedure described for Compound 2A, Step D, 5-(3-{2R-[4-(4-fluoro-phenyl)-3-oxo-but-1-enyl]-5-oxo-pyrrolidin-1-yl}-propyl)-thiophene-2-carboxylic acid methyl ester (74 mg, 0.172 mmol) was hydrogenated in EtOH (20 mL) in the presence of 10% palladium on carbon (50 mg) at 50 psi for 2 h to provide 5-(3-{2S-[4-(4-fluoro-phenyl)-3-oxo-butyl]-5-oxo-pyrrolidin-1-yl}-propyl)-thiophene-2-carboxylic acid methyl ester (72 mg). $^{1}$H NMR (CDCl$_{3}$) δ 7.61 (d, 1H), 7.14 (m, 2H), 7.01 (m, 2H), 6.80 (d, 1H), 3.84 (s, 3H), 3.66 (s, 2H), 3.64 (m, 1H), 3.51 (m, 1H), 2.94 (m, 1H), 2.81 (t, 2H), 2.43 (m, 2H), 2.30 (m, 2H), 2.05-1.79 (m, 4H), 1.56 (m, 2H); MS 432.0 (M+1), 430.1 (M−1).

Step C: 5-(3-{2S-[4-(4-Fluoro-phenyl)-3-hydroxy-butyl]-5-oxo-pyrrolidin-1-yl}-propyl)-thiophene-2-carboxylic acid methyl ester. Analogous to the procedure described for Compound 2B, Step C, 5-(3-{2S-[4-(4-fluoro-phenyl)-3-oxo-butyl]-5-oxo-pyrrolidin-1-yl}-propyl)-thiophene-2-carboxylic acid methyl ester (69 mg, 0.160 mmol) was reduced with NaBH$_{4}$ (6 mg, 0.160 mmol) over 2 h. Purification by preparative thin layer chromatography (EtOAc) provided 5-(3-{2S-[4-(4-fluoro-phenyl)-3-hydroxy-butyl]-5-oxo-pyrrolidin-1-yl}-propyl)-thiophene-2-carboxylic acid methyl ester (37 mg). $^{1}$H NMR (CDCl$_{3}$) δ 7.61 (d, 1H), 7.15 (m, 2H), 7.00 (m, 2H), 6.81 (d, 1H), 3.82 (s, 3H), 3.75 (m, 1H), 3.60 (m, 2H), 2.99 (m, 1H), 2.83 (t, 2H), 2.77 (m, 1H), 2.34 (m, 2H), 2.10 (m, 1H), 2.00-1.80 (m, 4H), 1.75 (m, 1H), 1.68-1.34 (m, 4H); MS 434.3 (M+1).

Step D: 5-(3-{2S-[4-(4-Fluoro-phenyl)-3-hydroxy-butyl]-5-oxo-pyrrolidin-1-yl}-propyl)-thiophene-2-carboxylic acid. Analogous to the procedure described for Compound 2A, Step E, 5-(3-{2S-[4-(4-fluoro-phenyl)-3-hydroxy-butyl]-5-oxo-pyrrolidin-1-yl}-propyl)-thiophene-2-carboxylic acid methyl ester (35 mg, 0.0807 mmol) was hydrolyzed with NaOH (1M, 0.10 mL) in MeOH (5 mL) heated under reflux over 29 h to provide 5-(3-{2S-[4-(4-fluoro-phenyl)-3-hydroxy-butyl]-5-oxo-pyrrolidin-1-yl}-propyl)-thiophene-2-carboxylic acid (36 mg). $^{1}$H NMR (CDCl$_{3}$) δ 7.67 (d, 1H), 7.15 (m, 2H), 7.00 (m, 2H), 6.84 (d, 1H), 3.77 (m, 1H), 3.62 (m, 2H), 3.01 (m, 1H), 2.85 (t, 2H), 2.78 (m, 1H), 2.62 (m, 1H), 2.36 (m, 2H), 2.10 (m, 1H), 2.00-1.72 (m, 4H), 1.69-1.34 (m, 4H); MS 420.1 (M+1), 417.7 (M−1).

Compound 3E 5-(3-{2S-[4-(4-Fluoro-phenyl)-3R-hydroxy-butyl]-5-oxo-pyrrolidin-1-yl}-propyl)-thiophene-2-carboxylic acid Step A: 5-(3-{2R-[4-(4-Fluoro-phenyl)-3S-hydroxy-but-1-enyl]-5-oxo-pyrrolidin-1-yl}-propyl)-thiophene-2-carboxylic acid methyl ester. To a solution of 5-(3-{2R-[4-(4-fluoro-phenyl)-3-oxo-but-1-enyl]-5-oxo-pyrrolidin-1-yl}-propyl)-thiophene-2-carboxylic acid methyl ester (20 mg, 0.047 mmol) and (R)-2-methyl-CBS-oxazaborolidine (1M in toluene, 0.047 mL, 0.047 mmol) in anhydrous toluene (3.0 mL) at −45° C. was added catecholborane (1M in THF, 0.14 mL, 0.14 mmol) dropwise. The reaction mixture was stirred at −45° C. for 17 h. Methanol (1 mL) was added and the reaction mixture was warmed to room temperature and was concentrated in vacuo. The residue was dissolved in CHCl$_3$ and the organic solution was washed with 1M NaOH (4×5 mL), 1M HCl (1×5 mL), and water (1×5 mL). The organic solution was dried (MgSO$_4$), filtered and concentrated. Purification by preparative thin layer chromatography (EtOAc) provided 5-(3-{2R-[4-(4-fluoro-phenyl)-3S-hydroxy-but-1-enyl]-5-oxo-pyrrolidin-1-yl}-propyl)-thiophene-2-carboxylic acid methyl ester as an approximate 39:1 ratio of 3S:3R alcohol diastereomers by HPLC. MS 432.1 (M+1).

Step B: 5-(3-{2S-[4-(4-Fluoro-phenyl)-3R-hydroxy-butyl]-5-oxo-pyrrolidin-1-yl}-propyl)-thiophene-2-carboxylic acid methyl ester. Analogous to the procedure described for Compound 2A, Step D, 5-(3-{2R-[4-(4-fluoro-phenyl)-3S-hydroxy-but-1-enyl]-5-oxo-pyrrolidin-1-yl}-propyl)-thiophene-2-carboxylic acid methyl ester (15 mg, 0.035 mmol) was hydrogenated in ethanol (10 mL) in the presence of 10% palladium on carbon (5 mg) at 50 psi for 2 h to provide 5-(3-{2S-[4-(4-fluoro-phenyl)-3R-hydroxy-butyl]-5-oxo-pyrrolidin-1-yl}-propyl)-thiophene-2-carboxylic acid methyl ester (11 mg). $^1$H NMR (CDCl$_3$) δ 7.60 (d, 1H), 7.14 (m, 2H), 7.00 (m, 2H), 6.81 (d, 1H), 3.82 (s, 3H), 3.77 (m, 1H), 3.60 (m, 2H), 3.00 (m, 1H), 2.83 (t, 2H), 2.76 (dd, 1H), 2.63 (dd, 1H), 2.34 (m, 2H), 2.08 (m, 1H), 1.98-1.42 (m, 8H); MS 434.1 (M+1).

Step C: 5-(3-{2S-[4-(4-Fluoro-phenyl)-3R-hydroxy-butyl]-5-oxo-pyrrolidin-1-yl}-propyl)-thiophene-2-carboxylic acid. Analogous to the procedure described for Compound 2A, Step E, 5-(3-{2S-[4-(4-fluoro-phenyl)-3R-hydroxy-butyl]-5-oxo-pyrrolidin-1-yl}-propyl)-thiophene-2-carboxylic acid methyl ester (11 mg, 0.0254 mmol) was hydrolyzed with NaOH (1M, 0.25 mL) in MeOH (4 mL) heated under reflux for 3 h to provide 5-(3-{2S-[4-(4-fluoro-phenyl)-3R-hydroxy-butyl]-5-oxo-pyrrolidin-1-yl}-propyl)-thiophene-2-carboxylic acid (9 mg). $^1$H NMR (CDCl$_3$) δ 7.67 (d, 1H), 7.14 (m, 2H), 6.99 (m, 2H), 6.83 (d, 1H), 3.78 (m, 1H), 3.62 (m, 2H), 3.02 (m, 1H), 2.85 (t, 2H), 2.76 (dd, 1H), 2.64 (dd, 1H), 2.37 (m, 2H), 2.09 (m, 1H), 2.00-1.42 (m, 8H); MS 420.1 (M+1), 418.0 (M−1).

Compound 3F

5-{3-[2S-(3-Hydroxy-4-naphthalen-2-yl-butyl)-5-oxo-pyrrolidin-1-yl]-propyl}-thiophene-2-carboxylic acid Step A: 5-{3-[2R-(4-Naphthalen-2-yl-3-oxo-but-1-enyl)-5-oxo-pyrrolidin-1-yl]-propyl}-thiophene-2-carboxylic acid tert-butyl ester. Analogous to the procedure described for Compound 2A, Step B, the anion derived from (3-naphthalen-2-yl-2-oxo-propyl)-phosphonic acid dimethyl ester (208 mg, 0.71 mmol) and NaH (60% by weight in oil, 26 mg, 0.65 mmol) was reacted with 5-[3-(2R-formyl-5-oxo-pyrrolidin-1-yl)-propyl]-thiophene-2-carboxylic acid tert-butyl ester (assumed 0.589 mmol) over 18 h. Purification by medium pressure chromatography (1:1 hexanes:EtOAc to EtOAc) provided 5-{3-[2R-(4-naphthalen-2-yl-3-oxo-but-1-enyl)-5-oxo-pyrrolidin-1-yl]-propyl}-thiophene-2-carboxylic acid tert-butyl ester (181 mg). $^1$H NMR (CDCl$_3$) δ 7.79 (m, 3H), 7.65 (s, 1H), 7.47 (m, 3H), 7.29 (m, 1H), 6.63 (m, 2H), 6.22 (d, 1H), 4.08 (m, 1H), 3.98 (s, 2H), 3.49 (m, 1H), 2.73 (m, 1H), 2.63 (m, 2H), 2.36 (m, 2H), 2.19 (m, 1H), 1.72 (m, 3H), 1.54 (s, 9H); MS 504.1 (M+1), 502.0 (M−1).

Step B: 5-{3-[2S-(4-Naphthalen-2-yl-3-oxo-butyl)-5-oxo-pyrrolidin-1-yl]-Propyl}-thiophene-2-carboxylic acid tert-butyl ester. Analogous to the procedure described for Compound 2A, Step D, 5-{3-[2R-(4-naphthalen-2-yl-3-oxo-but-1-enyl)-5-oxo-pyrrolidin-1-yl]-propyl}-thiophene-2-carboxylic acid tert-butyl ester (178 mg, 0.353 mmol) was hydrogenated in EtOH (40 mL) in the presence of 10% palladium on carbon (75 mg) at 50 psi for 3 h. Purification by medium pressure chromatography (1:1 hexanes:EtOAc to EtOAc) provided 5-{3-[2S-(4-naphthalen-2-yl-3-oxo-butyl)-5-oxo-pyrrolidin-1-yl]-propyl}-thiophene-2-carboxylic acid tert-butyl ester (144 mg). $^1$H NMR (CDCl$_3$) δ 7.80 (m, 3H), 7.66 (s, 1H), 7.48 (m, 3H), 7.30 (m, 1H), 6.74 (d, 1H), 3.85 (s, 2H), 3.59 (m, 1H), 3.48 (m, 1H), 2.89 (m, 1H), 2.73 (t, 2H), 2.47 (m, 2H), 2.26 (m, 2H), 2.04-1.74 (m, 4H), 1.53 (s, 9H), 1.50 (m, 2H); MS 506.1 (M+1), 503.8 (M−1).

Step C: 5-{3-[2S-(3-Hydroxy-4-naphthalen-2-yl-butyl)-5-oxo-pyrrolidin-1-yl]-propyl}-thiophene-2-carboxylic acid tert-butyl ester. Analogous to the procedure described for Compound 2B, Step C, 5-{3-[2S-(4-naphthalen-2-yl-3-oxo-butyl)-5-oxo-pyrrolidin-1-yl]-propyl}-thiophene-2-carboxylic acid tert-butyl ester (142 mg, 0.281 mmol) was reduced with NaBH$_4$ (11 mg, 0.281 mmol) over 2 h. Purification by medium pressure chromatography (1:1 hexanes:EtOAc to EtOAc) provided 5-{3-[2S-(3-hydroxy-4-naphthalen-2-yl-butyl)-5-oxo-pyrrolidin-1-yl]-propyl}-thiophene-2-carboxylic acid tert-butyl ester (125 mg). $^1$H NMR (CDCl$_3$) δ 7.79 (m, 3H), 7.65 (s, 1H), 7.52 (d, 1H), 7.46 (m, 2H), 7.32 (d, 1H), 6.76 (d, 1H), 3.90 (m, 1H), 3.62 (m, 2H), 2.98 (m, 2H), 2.81 (m, 3H), 2.34 (m, 2H), 2.10 (m, 1H), 2.04-1.75 (m, 2H), 1.70-1.36 (m, 6H), 1.52 (s, 9H); MS 508.0(M+1).

Step D: 5-{3-[2S-(3-Hydroxy-4-naphthalen-2-yl-butyl)-5-oxo-pyrrolidin-1-yl]-propyl}-thiophene-2-carboxylic acid. To a solution of 5-{3-[2S-(3-hydroxy-4-naphthalen-2-yl-butyl)-5-oxo-pyrrolidin-1-yl]-propyl}-thiophene-2-carboxylic acid tert-butyl ester (123 mg, 0.242 mmol) in CH$_2$Cl$_2$ (20 mL) at 0° C. was added TFA (0.19 mL, 0.247 mmol). The reaction mixture was stirred at room temperature for 23 h and was concentrated in vacuo. The residue was purified by preparative thin layer chromatography (EtOAc) to provide the title compound, Compound 3F (47 mg). $^1$H NMR (CDCl$_3$) δ 7.78 (m, 3H), 7.63 (m, 2H), 7.44 (m, 2H), 7.31 (m, 1H), 6.78 (m, 1H), 3.89 (m, 1H), 3.57 (m, 2H), 2.94 (m, 2H), 2.79 (m, 3H), 2.32 (m, 2H), 2.10-1.17 (m, 9H); MS 452.3 (M+1), 450.2 (M−1).

Compound 3G

5-{3-[2S-(4-Biphenyl-3-yl-3-hydroxy-butyl)-5-oxo-pyrrolidin-1-yl]-propyl}-thiophene-2-carboxylic acid Step A: 5-{3-[2R-(4-Biphenyl-3-yl-3-oxo-but-1-enyl)-5-oxo-pyrrolidin-1-yl]propyl}-thiophene-2-carboxylic acid methyl ester. Analogous to the procedure described for Compound 2A, Step B, the anion derived from (3-biphenyl-3-yl-2-oxo-propyl)-phosphonic acid dimethyl ester (3.217 g, 10.09 mmol) and NaH (60% by weight in oil, 404 mg, 10.09 mmol) was reacted with 5-[3-(2R-formyl-5-oxo-pyrrolidin-1-yl)-propyl]-thiophene-2-carboxylic acid methyl ester (assumed 10.09 mmol) over 17 h. Purification by medium pressure chromatography (solvent gradient 9:1 hexanes:EtOAc to EtOAc) provided 5-{3-[2R-(4-biphenyl-3-yl-3-oxo-but-1-enyl)-5-oxo-pyrrolidin-1-yl]-propyl}-thiophene-2-carboxylic acid methyl ester (4.0 g). ¹H NMR (CDCl₃) δ 7.56 (m, 3H), 7.49 (m, 1H), 7.42 (m, 4H), 7.34 (m, 1H), 7.16 (d, 1H), 6.73 (d, 1H), 6.62 (dd, 1H), 6.22 (d, 1H), 4.11 (m, 1H), 3.88 (s, 2H), 3.82 (s, 3H), 3.54 (m, 1H), 2.79 (m, 1H), 2.73 (t, 2H), 2.36 (m, 2H), 2.20 (m, 1H), 1.76 (m, 3H); MS 488.1 (M+1), 486.0 (M−1).

Step B: 5-{3-[2S-(4-Biphenyl-3-yl-3-oxo-butyl)-5-oxo-pyrrolidin-1-yl]-propyl}-thiophene-2-carboxylic acid methyl ester. Analogous to the procedure described for Compound 2A, Step D, a mixture of 5-{3-[2R-(4-biphenyl-3-yl-3-oxo-but-1-enyl)-5-oxo-pyrrolidin-1-yl]-propyl}-thiophene-2-carboxylic acid methyl ester (3.535 g, 7.25 mmol), 10% palladium on carbon (750 mg), and EtOH (250 mL) was hydrogenated at 50 psi for 2 h to provide 5-{3-[2S-(4-biphenyl-3-yl-3-oxo-butyl)-5-oxo-pyrrolidin-1-yl]-propyl}-thiophene-2-carboxylic acid methyl ester which was used without further purification in Step C. MS 490.1 (M+1).

Step C: 5-{3-[2S-(4-Biphenyl-3-yl-3-hydroxy-butyl)-5-oxo-pyrrolidin-1-yl]-propyl}-thiophene-2-carboxylic acid ethyl ester. Analogous to the procedure described for Compound 2B, Step C, 5-{3-[2S-(4-biphenyl-3-yl-3-oxo-butyl)-5-oxo-pyrrolidin-1-yl]-propyl}-thiophene-2-carboxylic acid methyl ester (7.25 mmol) was treated with NaBH₄ (274 mg, 7.25 mmol) in EtOH at room temperature for 1 h. Purification by medium pressure chromatography (1:1 hexanes:EtOAc to EtOAc) provided 5-{3-[2S-(4-biphenyl-3-yl-3-hydroxy-butyl)-5-oxo-pyrrolidin-1-yl]-propyl}-thiophene-2-carboxylic acid ethyl ester (1.68 g). ¹H NMR (CDCl₃) δ 7.58 (m, 3H), 7.40 (m, 6H), 7.17 (d, 1H), 6.79 (d, 1H), 4.27 (q, 2H), 3.85 (m, 1H), 3.62 (m, 2H), 3.00 (m, 1H), 2.86 (m, 3H), 2.71 (m, 1H), 2.34 (m, 2H), 2.10 (m, 1H), 2.01-1.75 (m, 4H), 1.70-1.35 (m, 4H), 1.31 (t, 3H); MS 506.1 (M+1).

Step D: 5-{3-[2S-(4-Biphenyl-3-yl-3-hydroxy-butyl)-5-oxo-pyrrolidin-1-yl]-propyl}-thiophene-2-carboxylic acid. Analogous to the procedure described for Compound 2A, Step E, 5-{3-[2S-(4-biphenyl-3-yl-3-hydroxy-butyl)-5-oxo-pyrrolidin-1-yl]-propyl}-thiophene-2-carboxylic acid ethyl ester (1.882 g, 3.72 mmol) was hydrolyzed with NaOH (1M, 5.6 mL) in MeOH (100 mL) over 3 h under reflux to provide the title compound of Example 3G (1.741 g). ¹H NMR (CDCl₃) δ 7.66 (d, 1H), 7.56 (d, 2H), 7.40 (m, 6H), 7.17 (d, 1H), 6.82 (d, 1H), 3.85 (m, 1H), 3.63 (m, 2H), 3.02 (m, 1H), 2.86 (m, 3H), 2.72 (m, 1H), 2.36 (m, 2H), 2.11 (m, 1H), 2.01-1.75 (m, 4H), 1.71-1.35 (m, 4H); MS 478.1 (M+1), 476.0 (M−1).

Compound 3H 5-(3-{2S-[4-(3-Fluoro-phenyl)-3-hydroxy-butyl]-5-oxo-pyrrolidin-1-yl}-propyl)-thiophene-2-carboxylic acid Step A: 5-(3-{2R-[4-(3-Fluoro-phenyl)-3-oxo-but-1-enyl]-5-oxo-pyrrolidin-1-yl}-propyl)-thiophene-2-carboxylic acid methyl ester. Analogous to the procedure described for Compound 2A, Step B, the anion derived from [3-(3-fluoro-phenyl)-2-oxo-propyl]-phosphonic acid dimethyl ester (3.236 g, 12.4 mmol) and NaH (60% in oil, 458 mg, 11.4 mmol) was reacted with 5-[3-(2R-formyl-5-oxo-pyrrolidin-1-yl)-propyl]-thiophene-2-carboxylic acid methyl ester (assumed 10.4 mmol) over 18 h. Purification by medium pressure chromatography eluting with 20% EtOAc in hexanes to 80% EtOAc in hexanes followed by a second column eluting with 20% acetone in toluene to 30% acetone in toluene provided 5-(3-{2R-[4-(3-fluoro-phenyl)-3-oxo-but-1-enyl]-5-oxo-pyrrolidin-1-yl}-propyl)-thiophene-2-carboxylic acid methyl ester (2.95 g). ¹H NMR (CDCl₃) δ 7.60 (d, 1H), 7.27 (m, 1H), 6.92 (m, 3H), 6.76 (d, 1H), 6.60 (dd, 1H), 6.18 (d, 1), 4.12 (m, 1H), 3.83 (s, 3H), 3.80 (s, 2H), 3.56 (m, 1H), 2.82 (m, 1H), 2.77 (t, 2H), 2.37 (m, 2H), 2.22 (m, 1H), 1.78 (m, 3H).

Step B: 5-(3-{2S-[4-(3-Fluoro-phenyl)-3-oxo-butyl]-5-oxo-pyrrolidin-1-yl}-propyl)-thiophene-2-carboxylic acid methyl ester. Analogous to the procedure described for Compound 2A, Step D, 5-(3-{2R-[4-(3-fluoro-phenyl)-3-oxo-but-1-enyl]-5-oxo-pyrrolidin-1-yl}-propyl)-thiophene-2-carboxylic acid methyl ester (2.95 g, 6.87 mmol) was hydrogenated in MeOH (60 mL) in the presence of 10% palladium on carbon (500 mg) at 50 psi for 2 h. Purification by medium pressure chromatography (50% EtOAc in hexanes to EtOAc) provided 5-(3-{2S-[4-(3-fluoro-phenyl)-3-oxo-butyl]-5-oxo-pyrrolidin-1-yl}-propyl)-thiophene-2-carboxylic acid methyl ester (2.60 g). ¹H NMR (CDCl₃) δ 7.60 (d, 1H), 7.28 (m, 1H), 6.92 (m, 3H), 6.79 (d, 1H), 3.82 (s, 3H), 3.67 (s, 2H), 3.62 (m, 1H), 3.50 (m, 1H), 2.93 (m, 1H), 2.80 (t, 2H), 2.43 (m, 2H), 2.27 (m, 2H), 2.04-1.76 (m, 4H), 1.50 (m, 2H); MS 432.2 (M+1), 430.1 (M−1).

Step C: 5-(3-{2S-[4-(3-Fluoro-phenyl)-3-hydroxy-butyl]-5-oxo-pyrrolidin-1-yl}-propyl)-thiophene-2-carboxylic acid methyl ester. Analogous to the procedure described for Compound 2B, Step C, 5-(3-{2S-[4-(3-fluoro-phenyl)-3-oxo-butyl]-5-oxo-pyrrolidin-1-yl}-propyl)-thiophene-2-carboxylic acid methyl ester (2.60 g, 6.03 mmol) was reacted with NaBH₄ (114 mg, 3.01 mmol) in MeOH (30 mL) at 0° C. for 3 h. Purification by medium pressure chromatography (EtOAc to 2% MeOH in CH₂Cl₂) provided 5-(3-{2S-[4-(3-fluoro-phenyl)-3-hydroxy-butyl]-5-oxo-pyrrolidin-1-yl}-propyl)-thiophene-2-carboxylic acid methyl ester (2.43 g). MS 434.0 (M+1).

Step D: 5-(3-{2S-[4-(3-Fluoro-phenyl)-3-hydroxy-butyl]-5-oxo-pyrrolidin-1-yl}-propyl)-thiophene-2-carboxylic acid. Analogous to the procedure described for Compound 2A, Step E, 5-(3-{2S-[4-(3-fluoro-phenyl)-3-hydroxy-butyl]-5-oxo-pyrrolidin-1-yl}-propyl)-thiophene-2-carboxylic acid methyl ester (2.43 g) was hydrolyzed with 2N NaOH in MeOH (30 mL) over 18 h to provide 5-(3-{2S-[4-(3-fluoro-phenyl)-3-hydroxy-butyl]-5-oxo-pyrrolidin-1-yl}-propyl)-thiophene-2-carboxylic acid (2.06 g).

Step E: Sodium salt of 5-(3-{2S-[4-(3-Fluoro-phenyl)-3-hydroxy-butyl]-5-oxo-Pyrrolidin-1-yl}-propyl)-thiophene-2-carboxylic acid. Analogous to the procedure described for Compound 2D, Step E, 5-(3-{2S-[4-(3-fluoro-phenyl)-3-hydroxy-butyl]-5-oxo-pyrrolidin-1-yl}-propyl)-thiophene-2-carboxylic acid (2.058 g, 4.905 mmol) was reacted with NaHCO₃ (412 mg, 4.906 mmol) to yield the sodium salt of the title compound of Example 3H. ¹H NMR (CD₃OD) δ 7.35 (d, 1H), 7.26 (m, 1H), 6.96 (m, 3H), 6.75 (d, 1H), 3.76 (m, 1H), 3.67 (m, 1H), 3.57 (m, 1H), 3.02 (m, 1H), 2.76 (m, 3H), 2.30 (m, 2H), 2.10 (m, 1H), 1.98-1.28 (m, 9H).

Compound 3I 5-(3-{2S-[4-(4-Ethyl-phenyl)-3-hydroxy-butyl]-5-oxo-pyrrolidin-1-yl}-propyl)-thiophene-2-carboxylic acid Step A: 5-(3-{2R-[4-(4-Ethyl-phenyl)-3-oxo-but-1-enyl]-5-oxo-pyrrolidin-1-yl}-propyl)-thiophene-2-carboxylic acid methyl ester. Analogous to the procedure described for Compound 2A, Step B, the anion derived from [3-(4-ethyl-phenyl)-2-oxo-propyl]-phosphonic acid diethyl ester (274 mg, 0.915 mmol) and NaH (60% by weight in oil, 41 mg, 1.01 mmol) was reacted with 5-[3-(2R-formyl-5-oxo-pyrrolidin-1-yl)-propyl]-thiophene-2-carboxylic acid methyl ester (assumed 1.01 mmol) over 18 h. Purification by medium pressure chromatography (1:1 hexanes:EtOAc to EtOAc) provided 5-(3-{2R-[4-(4-ethyl-phenyl)-3-oxo-but-1-enyl]-5-oxo-pyrrolidin-1-yl}-thiophene-2-carboxylic acid methyl ester (227 mg). $^1$H NMR (CDCl$_3$) δ 7.59 (d, 1H), 7.13 (d, 2H), 7.07 (d, 2H), 6.75 (d, 1H), 6.58 (dd, 1H), 6.18 (d, 1H), 4.10 (m, 1H), 3.83 (s, 3H), 3.77 (s, 2H), 3.53 (m, 1H), 2.78 (m, 3H), 2.59 (q, 2H), 2.36 (m, 2H), 2.19 (m, 1H), 1.76 (m, 3H), 1.19 (t, 3H); MS 440.2 (M+1).

Step B: 5-(3-{2S-[4-(4-Ethyl-phenyl)-3-oxo-butyl]-5-oxo-pyrrolidin-1-yl}-propyl)-thiophene-2-carboxylic acid methyl ester. Analogous to the procedure described for Compound 2A, Step D, 5-(3-{2R-[4-(4-ethyl-phenyl)-3-oxo-but-1-enyl]-5-oxo-pyrrolidin-1-yl}-propyl)-thiophene-2-carboxylic acid methyl ester (227 mg, 0.517 mmol) was hydrogenated in MeOH (30 mL) in the presence of 10% palladium on carbon at 50 psi for 1.5 h. Purification by medium pressure chromatography (1:1 hexanes:EtOAc to EtOAc) provided 5-(3-{2S-[4-(4-ethyl-phenyl)-3-oxo-butyl]-5-oxo-pyrrolidin-1-yl}-propyl)-thiophene-2-carboxylic acid methyl ester (119 mg). $^1$H NMR (CDCl$_3$) δ 7.62 (d, 1H), 7.16 (d, 2H), 7.10 (d, 2H), 6.81 (d, 1H), 3.84 (s, 3H), 3.65 (s, 2H), 3.63 (m, 1H), 3.49 (m, 1H), 2.95 (m, 1H), 2.80 (t, 2H), 2.62 (q, 2H), 2.43 (m, 2H), 2.31 (m, 2H), 2.06-1.79 (m, 4H), 1.48 (m, 2H), 1.21 (t, 3H); MS 442.2 (M+1).

Step C: 5-(3-{2S-[4-(4-Ethyl-phenyl)-3-hydroxy-butyl]-5-oxo-pyrrolidin-1-yl}-propyl)-thioihene-2-carboxylic acid methyl ester. Analogous to the procedure described for Compound 2B, Step C, 5-(3-{2S-[4-(4-ethyl-phenyl)-3-oxo-butyl]-5-oxo-pyrrolidin-1-yl}-propyl)-thiophene-2-carboxylic acid methyl ester (109 mg, 0.247 mmol) was reduced with NaBH$_4$ (5 mg, 0.132 mmol) in MeOH (7 mL) at 0° C. to room temperature over 3 h. Purification by medium pressure chromatography (1:1 hexanes:EtOAc to EtOAc) provided 5-(3-{2S-[4-(4-ethyl-phenyl)-3-hydroxy-butyl]-5-oxo-pyrrolidin-1-yl}-propyl)-thiophene-2-carboxylic acid methyl ester (77 mg). $^1$H NMR (CDCl$_3$) δ 7.61 (d, 1H), 7.16 (d, 2H), 7.10 (d, 2H), 6.81 (d, 1H), 3.83 (s, 3H), 3.77 (m, 1H), 3.62 (m, 2H), 3.01 (m, 1H), 2.83 (t, 2H), 2.77 (m, 1H), 2.60 (m, 3H), 2.35 (m, 2H), 2.09 (m, 1H), 1.99-1.34 (m, 8H), 1.22 (t, 3H); MS 444.3 (M+1).

Step D: 5-(3-{2S-[4-(4-Ethyl-phenyl)-3-hydroxy-butyl]-5-oxo-pyrrolidin-1-yl}-propyl)-thiophene-2-carboxylic acid. Analogous to the procedure described for Compound 2A, Step E, 5-(3-{2S-[4-(4-ethyl-phenyl)-3-hydroxy-butyl]-5-oxo-pyrrolidin-1-yl}-propyl)-thiophene-2-carboxylic acid methyl ester (76 mg) was hydrolyzed with 2N NaOH in MeOH (7 mL) over 18 h to provide the title compound of Example 3(58 mg). $^1$H NMR (CD$_3$OD) δ 7.57 (m, 1H), 7.08 (d, 4H), 6.88 (d, 1H), 3.72 (m, 1H), 3.63 (m, 1H), 3.52 (m, 1H), 2.99 (m, 1H), 2.81 (t, 2H), 2.68 (m, 2H), 2.56 (q, 2H), 2.27 (m, 2H), 2.06 (m, 1H), 1.95-1.25 (m, 6H), 1.16 (t, 3H); MS 430.3 (M+1), 428.5 (M−1).

Compound 3J 5-(3-{2S-[4-(4-Fluoro-3-methyl-phenyl)-3-hydroxy-butyl]-5-oxo-pyrrolidin-1-yl}-propyl)-thiophene-2-carboxylic acid Step A: 5-(3-{2R-[4-(4-Fluoro-3-methyl-phenyl)-3-oxo-but-1-enyl]-5-oxo-pyrrolidin-1-yl}-propyl)-thiophene-2-carboxylic acid methyl ester. Analogous to the procedure described for Compound 2A, Step B, the anion derived from [3-(4-fluoro-3-methyl-phenyl)-2-oxo-propyl]-phosphonic acid diethyl ester (273 mg, 0.903 mmol) and NaH (60% by weight in oil, 41 mg, 1.01 mmol) was reacted with 5-[3-(2R-formyl-5-oxo-pyrrolidin-1-yl)-propyl]-thiophene-2-carboxylic acid methyl ester (assumed 1.01 mmol) over 18 h. Purification by medium pressure chromatography (20% EtOAc in hexanes to EtOAc) provided 5-(3-{2R-[4-(4-fluoro-3-methyl-phenyl)-3-oxo-but-1-enyl]-5-oxo-pyrrolidin-1-yl}-propyl)-thiophene-2-carboxylic acid methyl ester (174 mg). $^1$H NMR (CDCl$_3$) δ 7.59 (d, 1H), 6.97 (d, 1H), 6.93 (d, 2H), 6.76 (d, 1H), 6.60 (dd, 1H), 6.18 (d, 1H), 4.11 (m, 1H), 3.82 (s, 3H), 3.73 (s, 2H), 3.56 (m, 1H), 2.82 (m, 1H), 2.77 (t, 2H), 2.36 (m, 2H), 2.22 (s, 3H), 2.19 (m, 1H), 1.78 (m, 3H); MS 444.2 (M+1); 442.2 (M−1).

Step B: 5-(3-{2S-[4-(4-Fluoro-3-methyl-phenyl)-3-oxo-butyl]-5-oxo-pyrrolidin-1-yl}-propyl)-thiophene-2-carboxylic acid methyl ester. Analogous to the procedure described for Compound 2A, Step D, 5-(3-{2R-[4-(4-fluoro-3-methyl-phenyl)-3-oxo-but-1-enyl]-5-oxo-pyrrolidin-1-yl}-propyl)-thiophene-2-carboxylic acid methyl ester (174 mg, 0.392 mmol) was hydrogenated in MeOH (30 mL) in the presence of 10% palladium on carbon (70 mg) at 50 psi for 1.5 h. Purification by medium pressure (30% EtOAc in hexanes to EtOAc) provided 5-(3-{2S-[4-(4-fluoro-3-methyl-phenyl)-3-oxo-butyl]-5-oxo-pyrrolidin-1-yl}-propyl)-thiophene-2-carboxylic acid methyl ester (114 mg). $^1$H NMR (CDCl$_3$) δ 7.60 (d, 1H), 6.97 (d, 1H), 6.93 (d, 2H), 6.79 (d, 1H), 3.82 (s, 3H), 3.63 (m, 1H), 3.60 (s, 2H), 3.50 (m, 1H), 2.93 (m, 1H), 2.79 (t, 2H), 2.42 (m, 2H), 2.33-2.21 (m, 5H), 2.02-1.78 (m, 4H), 1.50 (m, 2H); MS 446.1 (M+1).

Step C: 5-(3-{2S-[4-(4-Fluoro-3-methyl-phenyl)-3-hydroxy-butyl]-5-oxo-pyrrolidin-1-yl}-propyl)-thiophene-2-carboxylic acid methyl ester. Analogous to the procedure described for Compound 2B, Step C, 5-(3-{2S-[4-(4-fluoro-3-methyl-phenyl)-3-oxo-butyl]-5-oxo-pyrrolidin-1-yl}-propyl)-thiophene-2-carboxylic acid methyl ester (114 mg, 0.256 mmol) was reduced with NaBH$_4$ (5 mg, 0.132 mmol) in MeOH (10 mL) at 0° C. to room temperature over 2.5 h. Purification by medium pressure chromatography (1:1 hexanes:EtOAc to EtOAc) provided 5-(3-{2S-[4-(4-fluoro-3-methyl-phenyl)-3-hydroxy-butyl]-5-oxo-pyrrolidin-1-yl}-propyl)-thiophene-2-carboxylic acid methyl ester (80 mg). $^1$H NMR (CDCl$_3$) δ 7.59 (d, 1H), 6.98 (d, 1H), 6.93 (m, 2H), 6.80 (d, 1H), 3.81 (s, 3H), 3.74 (m, 1H), 3.60 (m, 2H), 2.99 (m, 1H), 2.82 (t, 2H), 2.72 (m, 1H), 2.54 (m, 1H), 2.33 (m, 2H), 2.22 (s, 3H), 2.08 (m, 1H), 1.96-1.32 (m, 8H); MS 448.1 (M+1).

Step D: 5-(3-{2S-[4-(4-Fluoro-3-methyl-phenyl)-3-hydroxy-butyl]-5-oxo-pyrrolidin-1-yl}-propyl)-thiophene-2-carboxylic acid. Analogous to the procedure described for Compound 2A, Step E, 5-(3-{2S-[4-(4-fluoro-3-methyl-phenyl)-3-hydroxy-butyl]-5-oxo-pyrrolidin-1-yl}-propyl)-thiophene-2-carboxylic acid methyl ester (80 mg, 0.179 mmol) was hydrolyzed with 2N NaOH in MeOH (6 mL) over 18 h to provide the title compound of Example 3J (56 mg). $^1$H NMR (CD$_3$OD) δ 7.58 (d, 1H), 7.08-6.98 (m, 2H), 6.90 (m, 2H), 3.69 (m, 2H), 3.55 (m, 1H), 3.04 (m, 1H), 2.84 (t, 2H), 2.67 (m, 2H), 2.31 (m, 2H), 2.21 (s, 3H), 2.11 (m, 1H), 1.98-1.27 (m, 7H); MS 432.4 (M−1).

Compound 3K

5-{3-[2S-(3-Hydroxy-4-phenyl-butyl)-5-oxo-pyrrolidin-1-yl]-propyl}-thiophene-2-carboxylic acid Step A: 5-{3-[2-oxo-5R-(3-oxo-4-phenyl-but-1-enyl)-pyrrolidin-1-yl]-propyl}-thiophene-2-carboxylic acid methyl ester. Analogous to the procedure described for Compound 2A, Step B, the anion derived from (2-oxo-3-phenyl-propyl)-phosphonic acid dimethyl ester (543 mg, 2.24 mmol) and NaH (60% by weight in oil, 94 mg, 2.35 mmol) was reacted with 5-[3-(2R-formyl-5-oxo-pyrrolidin-1-yl)-propyl]-thiophene-2-carboxylic acid methyl ester (assumed 2.36 mmol) over 18 h. Purification by medium pressure chromatography (20% EtOAc in hexanes to 70% EtOAc in hexanes) provided 5-{3-[2-oxo-5R-(3-oxo-4-phenyl-but-1-enyl)-pyrrolidin-1-yl]-propyl}-thiophene-2-carboxylic acid methyl ester (315 mg). $^1$H NMR (CDCl$_3$) δ 7.61 (d, 1H), 7.34-7.15 (m, 5H), 6.77 (m, 1H), 6.61 (dd, 1H), 6.19 (d, 1H), 4.12 (m, 1H), 3.85 (s, 3H), 3.82 (s, 2H), 3.54 (m, 1H), 2.81 (m, 3H), 2.37 (m, 2H), 2.20 (m, 1H), 1.78 (m, 3H); MS 411.8 (M+1); 409.7 (M−1).

Step B: 5-{3-[2-Oxo-5S-(3-oxo-4-phenyl-butyl)-pyrrolidin-1-yl]-propyl}-thiophene-2-carboxylic acid methyl ester. Analogous to the procedure described for Compound 2A, Step D, 5-{3-[2-oxo-5R-(3-oxo-4-phenyl-but-1-enyl)-pyrrolidin-1-yl]-propyl}-thiophene-2-carboxylic acid methyl ester (305 mg, 0.741 mmol) was hydrogenated in MeOH (30 mL) in the presence of 10% palladium on carbon (100 mg) at 50 psi for 1.5 h. Purification by medium pressure (1:1 hexanes:EtOAc to EtOAc) provided 5-{3-[2-oxo-5S-(3-oxo-4-phenyl-butyl)-pyrrolidin-1-yl]-propyl}-thiophene-2-carboxylic acid methyl ester (235 mg). $^1$H NMR (CDCl$_3$) δ 7.62 (d, 1H), 7.35-7.18 (m, 5H), 6.81 (d, 1H), 3.84 (s, 3H), 3.69 (s, 2H), 3.62 (m, 1H), 3.48 (m, 1H), 2.94 (m, 1H), 2.80 (t, 2H), 2.43 (m, 2H), 2.26 (m, 2H), 2.04-1.78 (m, 4H), 1.48 (m, 2H); MS 414.1 (M+1).

Step C: 5-{3-[2S-(3-Hydroxy-4-phenyl-butyl)-5-oxo-pyrrolidin-1-yl]-propyl}-thiophene-2-carboxylic acid methyl ester. Analogous to the procedure described for Compound 2B, Step C, 5-{3-[2-oxo-5S-(3-oxo-4-phenyl-butyl)-pyrrolidin-1-yl]-propyl}-thiophene-2-carboxylic acid methyl ester (235 mg, 0.569 mmol) was reduced with NaBH$_4$ (11 mg, 0.284 mmol) in MeOH (7 mL) at 0° C. to room temperature over 2 h. Purification by medium pressure chromatography (30% EtOAc in hexanes to EtOAc) provided 5-{3-[2S-(3-hydroxy-4-phenyl-butyl)-5-oxo-pyrrolidin-1-yl]-propyl}-thiophene-2-carboxylic acid methyl ester (177 mg). $^1$H NMR (CDCl$_3$) δ 7.70 (d, 1H), 7.32-7.16 (m, 5H), 6.79 (d, 1H), 3.80 (m, 4H), 3.60 (m, 2H), 2.99 (m, 1H), 2.80 (m, 3H), 2.62 (m, 1H), 2.32 (m, 2H), 2.09 (m, 1H), 1.97-1.32 (m, 8H); MS 416.0 (M+1).

Step D: 5-{3-[2S-(3-Hydroxy-4-phenyl-butyl)-5-oxo-pyrrolidin-1-yl]-propyl}-thiophene-2-carboxylic acid. Analogous to the procedure described for Compound 2A, Step E, 5-{3-[2S-(3-hydroxy-4-phenyl-butyl)-5-oxo-pyrrolidin-1-yl]-propyl}-thiophene-2-carboxylic acid methyl ester (177 mg, 0.426 mmol) was hydrolyzed with 2N NaOH in MeOH (7 mL) over 18 h to provide the title compound of Example 3K (132 mg). $^1$H NMR (CD$_3$OD) δ 7.57 (m, 1H), 7.26-7.14 (m, 5H), 6.88 (d, 1H), 3.75 (m, 1H), 3.64 (m, 1H), 3.54 (m, 1H), 3.00 (m, 1H), 2.82 (t, 2H), 2.71 (m, 2H), 2.28 (m, 2H), 2.08 (m, 1H), 1.96-1.26 (m, 7H); MS 402.2 (M+1), 400.4 (M−1).

Compound 3L 5-(3-{2S-[4-(3-Chloro-phenyl)-3R-hydroxy-butyl]-5-oxo-pyrrolidin-1-yl}-propyl)-thiophene-2-carboxylic acid Step A: 5-(3-{2R-[4-(3-Chloro-phenyl)-3-oxo-but-1-enyl]-5-oxo-pyrrolidin-1-yl}-propyl)-thiophene-2-carboxylic acid methyl ester. Analogous to the procedure described for Compound 2C, Step D, the anion derived from [3-(3-chloro-phenyl)-2-oxo-propyl]-phosphonic acid dimethyl ester (3.68 g, 13.3 mmol) and NaH (60% by weight in oil, 533 mg, 14.5 mmol) was reacted with 5-[3-(2R-formyl-5-oxo-pyrrolidin-1-yl)-propyl]-thiophene-2-carboxylic acid methyl ester (assumed 12.1 mmol) over 24 h. Purification by medium pressure chromatography (15% acetone in toluene to 20% acetone in toluene) provided 5-(3-{2R-[4-(3-chloro-phenyl)-3-oxo-but-1-enyl]-5-oxo-pyrrolidin-1-yl}-propyl)-thiophene-2-carboxylic acid methyl ester (2.63 g). $^1$H NMR (CDCl$_3$) δ 7.59 (d, 1H), 7.23 (m, 2H), 7.16 (s, 1H), 7.04 (m, 1H), 6.76 (d, 1H), 6.60 (dd, 1H), 6.17 (d, 1H), 4.12 (m, 1H), 3.82 (s, 3H), 3.78 (s, 2H), 3.56 (m, 1H), 2.87-2.75 (m, 3H), 2.45-2.28 (m, 2H), 2.21 (m, 1H), 1.78 (m, 3H).

Step B: 5-(3-{2R-[4-(3-Chloro-phenyl)-3S-hydroxy-but-1-enyl]-5-oxo-pyrrolidin-1-yl}-propyl)-thiophene-2-carboxylic acid methyl ester. To a solution of 5-(3-{2R-[4-(3-chloro-phenyl)-3-oxo-but-1-enyl]-5-oxo-pyrrolidin-1-yl}-propyl)-thiophene-2-carboxylic acid methyl ester (2.63 g, 5.91 mmol) and (R)-2-methyl-CBS-oxazaborolidine (1M in toluene, 5.9 mL, 5.9 mmol in CH$_2$Cl$_2$ (140 mL) at −45° C. was added catecholborane (1M in THF, 17.7 mL, 17.7 mmol) dropwise. The reaction mixture was stirred for 18 h and MeOH was added. After stirring for 18 h, the volatiles were removed in vacuo and CH$_2$Cl$_2$ was added. The organic solution was washed with cold 1N NaOH (3 times), 1N HCl, water and brine. The organic solution was dried (MgSO$_4$), filtered and concentrated. Purification by medium pressure chromatography (1:1 hexanes:EtOAc to 80% EtOAc in hexanes) provided 5-(3-{2R-[4-(3-chloro-phenyl)-3S-hydroxy-but-1-enyl]-5-oxo-pyrrolidin-1-yl}-propyl)-thiophene-2-carboxylic acid methyl ester (870 mg) as an approximate 10:1 ratio of 3S:3R alcohol diastereomers by $^1$H NMR. $^1$H NMR (CDCl$_3$) δ 7.61 (d, 1H), 7.21 (m, 3H), 7.07 (m, 1H), 6.80 (d, 1H), 5.68 (dd, 1H), 5.45 (dd, 1H), 4.36 (m, 1H), 4.01 (m, 1H), 3.82 (s, 3H), 3.51 (m, 1H), 2.84-2.76 (m, 5H), 2.44-2.28 (m, 2H), 2.18 (m, 1H), 1.86-1.56 (m, 4H).

Step C: 5-(3-{2S-[4-(3-Chloro-phenyl)-3R-hydroxy-butyl]-5-oxo-pyrrolidin-1-yl}-propyl)-thiophene-2-carboxylic acid methyl ester. Analogous to the procedure described for Compound 2A, Step D, a mixture of 5-(3-{2R-[4-(3-chloro-phenyl)-3S-hydroxy-but-1-enyl]-5-oxo-pyrrolidin-1-yl}-propyl)-thiophene-2-carboxylic acid methyl ester (850 mg) and 10% palladium on carbon (100 mg) in MeOH (50 mL) was hydrogenated on a Parr shaker at 50 psi for 3 h. The hydrogenation was repeated using 100 mg of 10% palladium on carbon for 6 h. Purification by medium pressure chromatography (1:1 hexanes:EtOAc to EtOAc) provided 5-(3-{2S-[4-(3-chloro-phenyl)-3R-hydroxy-butyl]-5-oxo-pyrrolidin-1-yl}-propyl)-thiophene-2-carboxylic acid methyl ester (504 mg). $^1$H NMR (CDCl$_3$) δ 7.61 (d, 1H), 7.23 (m, 3H), 7.08 (m, 1H), 6.82 (d, 1H), 3.83 (s, 3H), 3.81 (m, 1H), 3.62 (m, 2H), 3.01 (m, 1H), 2.84 (t, 2H), 2.77 (m, 1H), 2.65 (m, 1H), 2.35 (m, 2H), 2.10 (m, 1H), 1.97-1.43 (m, 8H).

Step D: 5-(3-{2S-[4-(3-Chloro-phenyl)-3R-hydroxy-butyl]-5-oxo-pyrrolidin-1-yl}-propyl)-thiophene-2-carboxylic acid. Analogous to the procedure described for Compound 2A, Step E, 5-(3-{2S-[4-(3-chloro-phenyl)-3R-hydroxy-butyl]-5-oxo-pyrrolidin-1-yl}-propyl)-thiophene-2-carboxylic acid methyl ester (504 mg) was hydrolyzed with 2N NaOH in MeOH (20 mL) at 50° C. over 4 h to provide the title compound of Example 3L (338.6 mg). $^1$H NMR (CDCl$_3$) δ 7.68 (d, 1H), 7.22 (m, 3H), 7.08 (m, 1H), 6.84 (d, 1H), 3.80 (m, 1H), 3.64 (m, 2H), 3.01 (m, 1H), 2.82 (m, 4H), 2.64 (m, 1H), 2.38 (m, 2H), 2.12 (m, 1H), 1.92 (m, 3H), 1.66 (m, 1H), 1.57-1.19 (m, 3H). MS 436.1 (M+1), 434.2 (M−1).

Compound 3M 5-(3-{2S-[3R-Hydroxy-4-(3-trifluoromethyl-phenyl)-butyl]-5-oxo-pyrrolidin-1-yl}-propyl)-thiophene-2-carboxylic acid Step A: 5-(3-{2-Oxo-5R-[3-oxo-4-(3-trifluoromethyl-phenyl)-but-1-enyl]-pyrrolidin-}-propyl)-thiophene-2-carboxylic acid methyl ester. Analogous to the procedure described for Compound 2A, Step B, the anion derived from [2-oxo-3-(3-trifluoromethyl-phenyl)-propyl]-phosphonic acid dimethyl ester (5.026 g, 17.0 mmol) and NaH (60% by weight in oil, 750 mg, 18.8 mmol) was reacted with 5-[3-(2R-formyl-5-oxo-pyrrolidin-1-yl)-propyl]-thiophene-2-carboxylic acid methyl ester (assumed 18.8 mmol) over 24 h. Purification by medium pressure chromatography (15% acetone in toluene to 20% acetone in toluene) provided 5-(3-{2-oxo-5R-[3-oxo-4-(3-trifluoromethyl-phenyl)-but-1-enyl]-pyrrolidin-1-yl}-propyl)-thiophene-2-carboxylic acid methyl ester (4.02 g). $^1$H NMR (CDCl$_3$) δ 7.61 (d, 1H), 7.54 (d, 1H), 7.45 (m, 2H), 7.37 (d, 1H), 6.79 (d, 1H), 6.66 (dd, 1H), 6.20 (d, 1H), 4.16 (m, 1H), 3.90 (s, 2H), 3.84 (s, 3H), 3.60 (m, 1H), 2.89-2.78 (m, 3H), 2.48-2.31 (m, 2H), 2.23 (m, 1H), 1.82 (m, 3H).

Step B: 5-(3-{2R-[3S-Hydroxy-4-(3-trifluoromethyl-phenyl)-but-1-enyl]-5-oxo-pyrrolidin-1-yl}-propyl)-thiophene-2-carboxylic acid methyl ester. Analogous to the procedure described for Compound 2A, Step C, 5-(3-{2-oxo-5R-[3-oxo-4-(3-trifluoromethyl-phenyl)-but-1-enyl]-pyrrolidin-1-yl}-propyl)-thiophene-2-carboxylic acid methyl ester (2.63 g, 5.91 mmol) was reduced with catecholborane (1M in THF, 18.8 mL, 18.8 mmol) in the presence of (R)-2-methyl-CBS-oxazaborolidine (1M in toluene, 0.94 mL, 0.94 mmol) at −45° C. over 18 h. The reaction was quenched by addition of 1N HCl and the mixture was stirred for 40 minutes. The organic solution was washed consecutively with ice cold 1N NaOH (3 times), 1N HCl (1 time), water (1 time), and brine. The organic solution was dried (MgSO$_4$), filtered, and concentrated. Purification by medium pressure chromatography (10% acetone in toluene to 20% acetone in toluene) provided 5-(3-{2R-[3S-hydroxy-4-(3-trifluoromethyl-phenyl)-but-1-enyl]-5-oxo-pyrrolidin-1-yl}-propyl)-thiophene-2-carboxylic acid methyl ester (3 g) as an approximate 4:1 ratio of 3S:3R alcohol diastereomers by $^1$H NMR. $^1$H NMR (CDCl$_3$) δ 7.60 (d, 1H), 7.50 (d, 1H), 7.41 (m, 3H), 6.79 (d, 1H), 5.70 (dd, 1H), 5.48 (dd, 1H), 4.41 (m, 1H), 4.00 (m, 1H), 3.81 (s, 3H), 3.50 (m, 1H), 2.86-2.77 (m, 5H), 2.42-2.26 (m, 2H), 2.16 (m, 1H), 1.81 (m, 2H), 1.72-1.54 (m, 2H).

Step C: 5-(3-{2S-[3R-Hydroxy-4-(3-trifluoromethyl-phenyl)-butyl]-5-oxo-pyrrolidin-1-yl}-propyl)-thiophene-2-carboxylic acid methyl ester. Analogous to the procedure described for Compound 2A, Step D, a mixture of 5-(3-{2R-[3S-hydroxy-4-(3-trifluoromethyl-phenyl)-but-1-enyl]-5-oxo-pyrrolidin-1-yl}-propyl)-thiophene-2-carboxylic acid methyl ester (3 g) and 10% palladium on carbon (400 mg) in MeOH (70 mL) was hydrogenated on a Parr shaker at 50 psi for 16 h. Purification by medium pressure chromatography (20% EtOAc in hexanes to 70% EtOAc in hexanes) provided 5-(3-{2S-[3R-hydroxy-4-(3-trifluoromethyl-phenyl)-butyl]-5-oxo-pyrrolidin-1-yl}-propyl)-thiophene-2-carboxylic acid methyl ester (2.26 g). $^1$H NMR (CDCl$_3$) δ 7.61 (d, 1H), 7.52-7.38 (m, 4H), 6.81 (d, 1H), 3.83 (m, 4H), 3.63 (m, 2H), 3.00 (m, 1H), 2.85 (m, 3H), 2.74 (m, 1H), 2.34 (m, 2H), 2.10 (m, 1H), 1.98-1.45 (m, 08H).

Step D: 5-(3-{2S-[3R-Hydroxy-4-(3-trifluoromethyl-phenyl)-butyl]-5-oxo-pyrrolidin-1-yl}-propyl)-thiophene-2-carboxylic acid. Analogous to the procedure described for Compound 2A, Step E, 5-(3-{2S-[3R-hydroxy-4-(3-trifluoromethyl-phenyl)-butyl]-5-oxo-pyrrolidin-1-yl}-propyl)-thiophene-2-carboxylic acid methyl ester (625 mg) was hydrolyzed with 2N NaOH in MeOH (20 mL) at room temperature over 24 h to provide the title compound of Example 3M (599 mg). $^1$H NMR (CDCl$_3$) δ 7.67 (d, 1H), 7.51-7.38 (m, 4H), 6.84 (d, 1H), 3.85 (m, 1H), 3.63 (m, 2H), 3.02 (m, 1H), 2.85 (m, 3H), 2.75 (m, 1H), 2.37 (m, 2H), 2.11 (m, 1H), 2.00-1.45 (m, 8H); MS 470.2 (M+1), 468.2 (M−1).

The sodium salt of Compound 3M was prepared by addition of sodium bicarbonate (1.0 equivalent) to a solution of Compound 3M (1.0 equivalent) in an ethanol/water mixture. The mixture was stirred and then was concentrated in vacuo to dryness to provide Compound 3M as the sodium salt.

Compound 4A 5S-(3-Hydroxy-4-naphthalen-2-yl-butyl)-1-[6-(2H-tetrazol-5-yl)-hexyl]-pyrrolidin-2-one Step A: 7-(2R-Formyl-5-oxo-pyrrolidin-1-yl)-heptanenitrile. Analogous to the procedure described for Compound 2A, Step A, 7-(2R-hydroxymethyl-5-oxo-pyrrolidin-1-yl)-heptanenitrile (150 mg, 0.67 mmol) was oxidized to generate 7-(2R-formyl-5-oxo-pyrrolidin-1-yl)-heptanenitrile which was used in Step B without further purification.

Step B: 7-[2R-(4-Naphthalen-2-yl-3-oxo-but-1-enyl)-5-oxo-pyrrolidin-1-yl]-heptanenitrile. Analogous to the procedure described for Compound 2A, Step B, the anion derived from (3-naphthalen-2-yl-2-oxo-propyl)-phosphonic acid dimethyl ester (196 mg, 0.67 mmol) and NaH (60% by weight in oil, 27 mg, 0.67 mmol) was reacted with 7-(2R-formyl-5-oxo-pyrrolidin-1-yl)-heptanenitrile (assumed 0.67 mmol) over 19 h. Purification by medium pressure chromatography (1:1 hexanes:EtOAc to EtOAc) provided 7-[2R-(4-naphthalen-2-yl-3-oxo-but-1-enyl)-5-oxo-pyrrolidin-1-yl]-heptanenitrile (74 mg). $^1$H NMR (CDCl$_3$) δ 7.79 (m, 3H), 7.67 (m, 1H), 7.46 (m, 2H), 7.30 (d, 1H), 6.65 (dd, 1H), 6.25 (d, 1H), 4.10 (m, 1H), 3.99 (s, 2H), 3.42 (m, 1H), 2.66 (m, 1H), 2.37 (m, 2H), 2.22 (m, 3H), 1.76 (m, 1H), 1.52 (m, 2H), 1.29 (m, 4H), 1.10 (m, 2H); MS 389.1 (M+1), 387.0 (M−1).

Step C: 7-[2S-(4-Naphthalen-2-yl-3-oxo-butyl)-5-oxo-pyrrolidin-1-yl]-heptanenitrile. Analogous to the procedure described for Compound 2A, Step D, 7-[2R-(4-naphthalen-2-yl-3-oxo-but-1-enyl)-5-oxo-pyrrolidin-1-yl]-heptanenitrile (74 mg, 0.19 mmol) was hydrogenated in EtOH (30 mL) in the presence of 10% palladium on carbon (50 mg) at 50 psi for 3 h. Purification by medium pressure (1:1 hexanes:EtOAc to EtOAc) provided 7-[2S-(4-naphthalen-2-yl-3-oxo-butyl)-5-oxo-pyrrolidin-1-yl]-heptanenitrile (45 mg). $^1$H NMR (CDCl$_3$) δ 7.80 (m, 3H), 7.66 (s, 1H), 7.47 (m, 2H), 7.30 (d, 1H), 3.85 (s, 2H), 3.51 (m, 2H), 2.81 (m, 1H), 2.48 (m, 2H), 2.28 (m, 4H), 1.98 (m, 2H), 1.62 (m, 4H), 1.44 (m, 4H), 1.22 (m, 2H); MS 391.4 (M+1), 389.3 (M−1).

Step D: 7-[2S-(3-Hydroxy-4-naphthalen-2-yl-butyl)-5-oxo-pyrrolidin-1-yl]-heptanenitrile. Analogous to the procedure described for Compound 2B, Step C, 7-[2S-(4-naphthalen-2-yl-3-oxo-butyl)-5-oxo-pyrrolidin-1-yl]-heptanenitrile (42 mg, 0.108 mmol) was reduced with NaBH$_4$ (4 mg, 0.11 mmol) in EtOH (20 mL) at room temperature for 3 h to provide 7-[2S-(3-hydroxy-4-naphthalen-2-yl-butyl)-5-oxo-pyrrolidin-1-yl]-heptanenitrile (40 mg). $^1$H NMR (CDCl$_3$) δ 7.80 (m, 3H), 7.65 (m, 1H), 7.46 (m, 2H), 7.33 (d, 1H), 3.92 (m, 1H), 3.59 (m, 2H), 3.03-2.78 (m, 3H), 2.35 (m, 4H), 2.12 (m, 1H), 1.81 (m, 1H), 1.68-1.40 (m, 11H), 1.28 (m, 2H); MS 393.1 (M+1).

Step E: 5S-(3-Hydroxy-4-naphthalen-2-yl-butyl)-1-[6-(2H-tetrazol-5-yl)-hexyl]-pyrrolidin-2-one. A solution of 7-[2S-(3-hydroxy-4-naphthalen-2-yl-butyl)-5-oxo-pyrrolidin-1-yl]-heptanenitrile (39 mg, 0.0994 mmol), azidotrimethylsilane (150 mg, 1.30 mmol), and dibutyltin oxide (25 mg, 0.10 mmol) in toluene (15 mL) was heated under reflux for 19 h. The reaction mixture was cooled and was acidified to pH of 2 with 1N HCl (5 mL). The volatiles were removed in vacuo and the aqueous solution was washed with EtOAc (4×10 mL). The organic solutions were combined, dried (MgSO$_4$), filtered and concentrated. The residue was purified by preparative thin layer chromatography (9:1 EtOAc:MeOH) to provide 5S-(3-hydroxy-4-naphthalen-2-yl-butyl)-1-[6-(2H-tetrazol-5-yl)-hexyl]-pyrrolidin-2-one (11 mg). $^1$H NMR (CDCl$_3$) δ 7.79 (m, 3H), 7.65 (m, 1H), 7.45 (m, 2H), 7.32 (m, 1H), 3.94 (m, 1H), 3.66 (m, 1H), 3.52 (m, 1H), 3.03-2.83 (m, 5H), 2.44 (m, 2H), 2.18 (m, 1H), 1.87-1.20 (m, 14H); MS 436.1 (M+1), 435.2 (M−1).

Compound 4B

5S-[3R-Hydroxy-4-(3-methoxymethyl-phenyl)-butyl]-1-[6-(2H-tetrazol-5-yl)-hexyl]-pyrrolidin-2-one Step A: 7-{2R-[4-(3-Methoxymethyl-phenyl)-3-oxo-but-1-enyl]-5-oxo-pyrrolidin-1-yl}-heptanenitrile. Analogous to the procedure described for Compound 2A, Step B, the anion derived from [3-(3-methoxymethyl-phenyl)-2-oxo-propyl]-phosphonic acid diethyl ester (2.87 g, 9.13 mmol) and NaH (60% in oil, 446 mg, 11.2 mmol) was reacted with 7-(2R-formyl-5-oxo-pyrrolidin-1-yl)-heptanenitrile (assumed 11.15 mmol) over 24 h. Purification by medium pressure chromatography (1:1 hexanes:EtOAc to EtOAc to 1% MeOH in $CH_2Cl_2$ to 3% MeOH in $CH_2Cl_2$) provided 7-{2R-[4-(3-methoxymethyl-phenyl)-3-oxo-but-1-enyl]-5-oxo-pyrrolidin-1-yl}-heptanenitrile (2.06 g). $^1$H NMR (CDCl$_3$) δ0 7.29 (m, 1H), 7.22 (m, 1H), 7.16 (s, 1H), 7.10 (m, 1H), 6.62 (dd, 1H), 6.20 (d, 1H), 4.41 (s, 2H), 4.12 (m, 1H), 3.82 (s, 2H), 3.49 (m, 1H), 3.37 (s, 3H), 2.72 (m, 1H), 2.43-2.20 (m, 5H), 1.76 (m, 1H), 1.60 (m, 2H), 1.40 (m, 4H), 1.24 (m, 2H)

Step B: 7-{2R-[3S-Hydroxy-4-(3-methoxymethyl-phenyl)-but-1-enyl]-5-oxo-pyrrolidin-1-yl}-heptanenitrile. To a solution of 7-{2R-[4-(3-methoxymethyl-phenyl)-3-oxo-but-1-enyl]-5-oxo-pyrrolidin-1-yl}-heptanenitrile (2.06 g, 5.39 mmol) and (R)-2-methyl-CBS-oxazaborolidine (1M in toluene, 0.81 mL, 0.81 mmol) in $CH_2Cl_2$ (200 mL) at −45° C. was added catecholborane (1M in THF, 16.2 mL, 16.2 mmol) dropwise. The reaction mixture was stirred at −45° C. for 24 h and 1N HCl was added. The reaction mixture was stirred at room temperature for 1 h and the layers were separated. The aqueous solution was washed with $CH_2Cl_2$ (2 times) and the organic solutions were combined, washed with cold 1N NaOH followed by brine 2 times. The organic solution was dried (MgSO$_4$), filtered and concentrated. Purification by medium pressure chromatography (1:1 hexanes:EtOAc to EtOAc to 1% MeOH in $CH_2Cl_2$ to 3% MeOH in $CH_2Cl_2$) provided 7-{2R-[3S-hydroxy-4-(3-methoxymethyl-phenyl)-but-1-enyl]-5-oxo-pyrrolidin-1-yl}-heptanenitrile (2.07 g) as an approximate 2:1 mixture of 3S:3R alcohol diastereomers by $^1$H NMR. $^1$H NMR (CDCl$_3$) δ 7.30-7.09 (m, 4H), 5.71 (m, 1H), 5.46 (m, 1H), 4.41 (s, 2H), 4.38 (m, 1H), 4.00 (m, 1H), 3.45 (m, 1H), 3.38 (s, 3H), 2.88-2.68 (m, 3H), 2.31 (m, 4H), 2.17 (m, 1H), 1.70-1.21 (m, 10H).

Step C: 7-{2S-[3R-Hydroxy-4-(3-methoxymethyl-phenyl)-butyl]-5-oxo-pyrrolidin-1-yl}-heptanenitrile. Analogous to the procedure described for Compound 2A, Step D, 7-{2R-[3S-hydroxy-4-(3-methoxymethyl-phenyl)-but-1-enyl]-5-oxo-pyrrolidin-1-yl}-heptanenitrile (2.07 g, 5.39 mmol) in EtOH (100 mL) was hydrogenated in the presence of 10% palladium on carbon (200 mg) at 50 psi for 24 h on a Parr shaker. Purification by medium pressure chromatography (1:1 hexanes:EtOAc to 2:1 EtOAc:hexanes to EtOAc to 2% MeOH in $CH_2Cl_2$ to 5% MeOH in $CH_2Cl_2$ to 10% MeOH in $CH_2Cl_2$) provided 7-{2S-[3R-hydroxy-4-(3-methoxymethyl-phenyl)-butyl]-5-oxo-pyrrolidin-1-yl}-heptanenitrile (1.28 g). $^1$H NMR (CDCl$_3$) δ 7.30-7.10 (m, 4H), 4.41 (s, 2H), 3.82 (m, 1H), 3.57 (m, 2H), 3.38 (s, 3H), 2.89 (m, 2H), 2.66 (m, 1H), 2.32 (m, 4H), 2.10 (m, 1H), 1.77 (m, 1H), 1.66-1.40 (m, 11H), 1.29 (m, 2H).

Step D: 5S-[3R-Hydroxy-4-(3-methoxymethyl-phenyl)-butyl]-1-[6-(2H-tetrazol-5-yl)-hexyl]-pyrrolidin-2-one. Analogous to the procedure described for Compound 4A, Step E, 7-{2S-[3R-hydroxy-4-(3-methoxymethyl-phenyl)-butyl]-5-oxo-pyrrolidin-1-yl}-heptanenitrile (1.28 g, 3.31 mmol) was reacted with azidotrimethylsilane (0.90 mL, 6.78 mmol) and dibutyltin oxide (128 mg, 0.514 mmol) in toluene (68 mL) heated under reflux for 24 h. Additional azidotrimethylsilane (1.8 mL, 13.56 mmol) and dibutyltin oxide (256 mg, 1.03 mmol) were added and the reaction mixture was continued under reflux for 3 days. Purification by medium pressure chromatography ($CH_2Cl_2$ to 2% MeOH in $CH_2Cl_2$ to 4% MeOH in $CH_2Cl_2$ to 6% MeOH in $CH_2Cl_2$ to 10% MeOH in $CH_2Cl_2$) provided 5S-[3R-hydroxy-4-(3-methoxymethyl-phenyl)-butyl]-1-[6-(2H-tetrazol-5-yl)-hexyl]-pyrrolidin-2-one (619.5 mg). $^1$H NMR (CDCl$_3$) δ 7.30-7.11 (m, 4H), 4.42 (s, 2H), 3.87 (m, 1H), 3.64 (m, 1H), 3.52 (m, 1H), 3.39 (s, 3H), 2.99-2.67 (m, 5H), 2.42 (m, 2H), 2.16 (m, 1H), 1.87-1.25 (m, 14H).

Step E: Sodium salt of 5S-[3R-Hydroxy-4-(3-methoxymethyl-phenyl)-butyl]-1-[6-(2H-tetrazol-5-yl)-hexyl]-pyrrolidin-2-one. Analogous to the procedure described for Compound 2C, Step D, treatment of 5S-[3R-hydroxy-4-(3-methoxymethyl-phenyl)-butyl]-1-[6-(2H-tetrazol-5-yl)-hexyl]-pyrrolidin-2-one (619.5 mg, 1.44 mmol) with NaHCO$_3$ (121 mg, 1.44 mmol) provided the sodium salt of the title compound, Compound 4B (628.3 mg). $^1$H NMR (CD$_3$OD) δ 7.20 (m, 4H), 3.79 (m, 1H), 3.64 (m, 1H), 3.50 (m, 1H), 2.97-2.69 (m, 5H), 2.29 (m, 2H), 2.10 (m, 1H), 1.81-1.28 (m, 14H).

Compound 5A

2-{3-[2S-(3-Hydroxy-4-phenyl-butyl)-5-oxo-pyrrolidin-1-yl]-propyl}-thiazole-4-carboxylic acid Step A: 2-{3-[2-Oxo-5R-(3-oxo-4-phenyl-but-1-enyl)-pyrrolidin-1-yl]-propyl}-thiazole-4-carboxylic acid ethyl ester. Analogous to the procedure described for Compound 2A, Step B, the anion derived from (2-oxo-3-phenyl-propyl)-phosphonic acid dimethyl ester (105 mg, 0.434 mmol) and NaH (60% by weight in oil, 17 mg, 0.434 mmol) was reacted with 2-[3-(2R-formyl-5-oxo-pyrrolidin-1-yl)-propyl]-thiazole-4-carboxylic acid ethyl ester (prepared from 2-[3-(2R-hydroxymethyl-5-oxo-pyrrolidin-1-yl)-propyl]-thiazole-4-carboxylic acid ethyl ester analogous to the procedure described for Compound 2A, Step A, assumed 0.359 mmol) over 17 h. Purification by medium pressure chromatography (1:1 hexanes:EtOAc to EtOAc) provided 2-{3-[2-oxo-5R-(3-oxo-4-phenyl-but-1-enyl)-pyrrolidin-1-yl]-propyl}-thiazole-4-carboxylic acid ethyl ester (59 mg). $^1$H NMR (CDCl$_3$) δ 8.03 (s, 1H), 7.33-7.17 (m, 5H), 6.61 (dd, 1H), 6.20 (d, 1H), 4.40 (q, 2H), 4.19 (m, 1H), 3.82 (s, 2H), 3.60 (m, 1H), 2.98 (m, 2H), 2.80 (m, 1H), 2.44-2.15 (m, 3H), 1.94 (m, 2H), 1.75 (m, 1H), 1.38 (t, 3H); MS 427.0 (M+1), 424.9 (M−1).

Step B: 2-{3-[2-Oxo-5S-(3-oxo-4-phenyl-butyl)-pyrrolidin-1-yl]-propyl}-thiazole-4-carboxylic acid ethyl ester. Analogous to the procedure described for Compound 2A, Step D, 2-{3-[2-oxo-5R-(3-oxo-4-phenyl-but-1-enyl)-pyrrolidin-1-yl]-propyl}-thiazole-4-carboxylic acid ethyl ester (23 mg, 0.0539 mmol) was hydrogenated in EtOH (15 mL) in the presence of 10% palladium on carbon (15 mg) at 50 psi for 3 h. Purification by preparative thin layer chromatography (1:1 hexanes:EtOAc) (2 times) provided 2-{3-[2-oxo-5S-(3-oxo-4-phenyl-butyl)-pyrrolidin-1-yl]-propyl}-thiazole-4-carboxylic acid ethyl ester (19 mg). $^1$H NMR (CDCl$_3$) δ 8.03 (s, 1H), 7.34-7.17 (m, 5H), 4.39 (q, 2H), 3.68 (s, 2H), 3.65 (m, 1H), 3.53 (m, 1H), 2.98 (m, 3H), 2.43 (t, 2H), 2.26 (m, 2H), 1.98 (m, 4H), 1.49 (m, 2H), 1.37 (t, 3H) MS 429.0 (M+1).

Step C: 2-{3-[2S-(3-Hydroxy-4-phenyl-butyl)-5-oxo-pyrrolidin-1-yl]-propyl}-thiazole-4-carboxylic acid ethyl ester.

Analogous to the procedure described for Compound 2B, Step C, 2-{3-[2-oxo-5S-(3-oxo-4-phenyl-butyl)-pyrrolidin-1-yl]-propyl}-thiazole-4-carboxylic acid ethyl ester (34 mg, 0.0793 mmol) was reduced with NaBH$_4$ (3 mg, 0.079 mmol) in EtOH (10 mL) at room temperature for 2 h. Purification by preparative thin layer chromatography (EtOAc) provided 2-{3-[2S-(3-hydroxy-4-phenyl-butyl)-5-oxo-pyrrolidin-1-yl]-propyl}-thiazole-4-carboxylic acid ethyl ester (18 mg). $^1$H NMR (CDCl$_3$) δ 8.02 (m, 1H), 7.33-7.18 (m, 5H), 4.38 (q, 2H), 3.82 (m, 1H), 3.65 (m, 2H), 3.06 (m, 3H), 2.80 (m, 1H), 2.67 (m, 1H), 2.32 (m, 2H), 2.09 (m, 2H), 1.98 (m, 2H), 1.82 (m, 1H), 1.68-1.42 (m, 4H), 1.37 (t, 3MS 431.1 (M+1).

Step D: 2-{3-[2S-(3-Hydroxy-4-phenyl-butyl)-5-oxo-pyrrolidin-1-yl]-propyl}-thiazole-4-carboxylic acid. Analogous to the procedure described for Compound 2A, Step E, 2-{3-[2S-(3-hydroxy-4-phenyl-butyl)-5-oxo-pyrrolidin-1-yl]-propyl}-thiazole-4-carboxylic acid ethyl ester (18 mg, 0.042 mmol) was hydrolyzed with 1 N NaOH (0.06 mL) in MeOH (5 mL) heated under reflux for 3 h to provide the title compound of Example 5A (8 mg). $^1$H NMR (CDCl$_3$) δ 8.01 (s, 1H), 7.33-7.18 (m, 5H), 3.83 (m, 1H), 3.66 (m, 2H), 3.09 (m, 1H), 3.02 (t, 2H), 2.81 (m, 1H), 2.68 (m, 1H), 2.35 (m, 2H), 2.06 (m, 4H), 1.82 (m, 1H), 1.69-1.38 (m, 4H); MS 403.0 (M+1), 401.0 (M−1).

Step E: Sodium salt of 2-{3-[2S-(3-Hydroxy-4-phenyl-butyl)-5-oxo-pyrrolidin-1-yl]-propyl}-thiazole-4-carboxylic acid. The sodium salt of the title compound, Compound 5A was prepared analogous to the procedure described for Compound 2B, Step E. $^1$H NMR (CDCl$_3$) δ 7.58 (s, 1H), 7.25-7.14 (m, 5H), 3.75 (m, 1H), 3.36 (m, 2H), 2.78 (m, 1H), 2.61 (m, 3H), 2.16-1.20 (m, 12H).

Compound 5B 5-(3-Hydroxy-4-phenyl-butyl)-1-{3-[4-(2H-tetrazol-5-yl)-phenyl]-propyl}-pyrrolidin-2-one Step A: 4-(3-{2-[3-(tert-Butyl-dimethyl-silanyloxy)-4-phenyl-butyl]-5-oxo-pyrrolidin-1-yl}-propyl)-benzonitrile. Analogous to the procedure described for Compound 1A, Step D, the anion derived from 5-[3-(tert-butyl-dimethyl-silanyloxy)-4-phenyl-butyl]-pyrrolidin-2-one (262.8 mg, 0.756 mmol) and NaHMDS (0.83 mL, 0.83 mmol) was reacted with 4-(3-bromo-propyl)-benzonitrile (186 mg, 0.832 mmol) at 70° C. for 24 h. Purification by medium pressure chromatography (5:1 hexanes:EtOAc to 1:1 hexanes:EtOAc to 1% MeOH in CH$_2$Cl$_2$ to 5% MeOH in CH$_2$Cl$_2$) provided 4-(3-{2-[3-(tert-butyl-dimethyl-silanyloxy)-4-phenyl-butyl]-5-oxo-pyrrolidin-1-yl}-propyl)-benzonitrile (257.6 mg). $^1$H NMR (CDCl$_3$) δ 7.56 (m, 2H), 7.26 (m, 5H), 7.13 (m, 2H), 3.85 (m, 1H), 3.62 (m, 1H), 3.48 (m, 1H), 2.93 (m, 1H), 2.82-2.60 (m, 4H), 2.29 (m, 2H), 1.88-1.25 (m, 7H); MS 491.5 (M+1).

Step B: 4-{3-[2-(3-Hydroxy-4-phenyl-butyl)-5-oxo-pyrrolidin-1-yl]-propyl}-benzonitrile. Analogous to the procedure described for Compound 1A, Step E, 4-(3-{2-[3-(tert-butyl-dimethyl-silanyloxy)-4-phenyl-butyl]-5-oxo-pyrrolidin-1-yl}-propyl)-benzonitrile (257.6 mg, 0.525 mmol) was deprotected with TBAF (1M in THF, 0.79 mL, 0.79 mmol) over 24 h. Purification by medium pressure chromatography (1:1 EtOAc: hexanes to EtOAc to 1% MeOH in CH$_2$Cl$_2$ to 3% MeOH in CH$_2$Cl$_2$) provided 4-{3-[2-(3-hydroxy-4-phenyl-butyl)-5-oxo-pyrrolidin-1-yl]-propyl}-benzonitrile (157.8 mg). $^1$H NMR (CDCl$_3$) δ 7.56 (m, 2H), 7.26 (m, 7H), 3.80 (m, 1H), 3.67-3.55 (m, 2H), 2.98 (m, 1H), 2.80 (m, 1H), 2.65 (t, 2H), 2.43-2.24 (m, 2H), 2.08 (m, 1H), 1.89-1.33 (m, 9H); MS 375.3 (M−1).

Step C: 5-(3-Hydroxy-4-phenyl-butyl)-1-{3-[4-(2H-tetrazol-5-yl)-phenyl]-propyl}-pyrrolidin-2-one. Analogous to the procedure described for Compound 4A, Step E, 4-{3-[2-(3-hydroxy-4-phenyl-butyl)-5-oxo-pyrrolidin-1-yl]-propyl}-benzonitrile (157.8 mg, 0.419 mmol) was reacted with azidotrimethylsilane (0.11 mL, 0.84 mmol) and dibutyltin oxide (20 mg, 0.08 mmol) in toluene (8.6 mL) heated under reflux for 60 h. Purification by medium pressure chromatography (CH$_2$Cl$_2$ to 2% MeOH in CH$_2$Cl$_2$ to 4% MeOH in CH$_2$Cl$_2$ to 6% MeOH in CH$_2$Cl$_2$) provided 5-(3-hydroxy-4-phenyl-butyl)-1-{3-[4-(2H-tetrazol-5-yl)-phenyl]-propyl}-pyrrolidin-2-one (144.7 mg). $^1$H NMR (CDCl$_3$) δ 8.02 (m, 2H), 7.27 (m, 7H), 3.84 (m, 1H), 3.67 (m, 2H), 3.10 (m, 1H), 2.84 (m, 1H), 2.67 (m, 2H), 2.53 (m, 1H), 2.42 (m, 1H), 2.14 (m, 1H), 1.97-1.40 (m, 9H); MS 420.3 (M+1), 418.3 (M−1).

Preparation 1

5-[3-(2R-Hydroxymethyl-5-oxo-pyrrolidin-1-yl)-propyl]-thiophene-2-carboxylic acid methyl ester Step A: 5R-(tert-Butyl-dimethyl-silanyloxymethyl)-1-prop-2-ynyl-pyrrolidin-2-one. To a solution of 5R-(tert-butyl-dimethyl-silanyloxymethyl)-pyrrolidin-2-one (Tetrahedron Asymmetry 1996, 7, 2113) (10.24 g, 44.6 mmol) in DMF (650 mL) at 0° C. was added NaHMDS (1M in THF, 49 mL, 49 mmol) dropwise. The reaction mixture was mechanically stirred at room temperature for 2 h to yield a thick suspension. The reaction mixture was cooled to 0° C. and propargyl bromide (80% in toluene, 5.0 mL, 45 mmol) in DMF (50 mL) was added slowly. The reaction mixture was stirred at 0° C. for 2 h and at room temperature for 0.5 h. Aqueous saturated ammonium chloride (700 mL) and water (300 mL) were added. The solution was washed with EtOAc (3×600 mL). The organic solutions were combined, washed with water (4×300 mL) followed by brine (1×300 mL). The organic solution was dried (Na$_2$SO$_4$), filtered and concentrated. Purification by medium pressure chromatography (10% EtOAc in hexanes to 25% EtOAc in hexanes) provided 5R-(tert-butyl-dimethyl-silanyloxymethyl)-1-prop-2-ynyl-pyrrolidin-2-one (9.85 g). $^1$H NMR (CDCl$_3$) δ 4.58 (dd, 1H), 3.88 (m, 1H), 3.77 (dd, 1H), 3.70 (d, 1H), 3.61 (m, 1H), 2.50-2.28 (m, 2H), 2.18 (m, 1H), 2.10 (m, 1H), 1.86 (m, 1H), 0.87 (s, 9H), 0.05 (s, 6H); MS 268.2 (M+1).

Step B: 5-{3-[2R-(tert-Butyl-dimethyl-silanyloxymethyl)-5-oxo-pyrrolidin-1-yl]-prop-1-ynyl}-thiophene-2-carboxylic acid methyl ester. A mixture of 5R-(tert-butyl-dimethyl-silanyloxymethyl)-1-prop-2-ynyl-pyrrolidin-2-one (8.64 g, 32.3 mmol), 5-bromo-thiophene-2-carboxylic acid methyl ester (7.5 g, 33.9 mmol), copper (I) iodide, CuI (308 mg, 1.62 mmol), tetrakis(triphenylphosphine)palladium(0) (1.9 g, 1.62 mmol), triethylamine (5.0 mL, 36 mmol), and CH$_3$CN (300 mL) was heated under reflux for 19 h. The reaction mixture was cooled to room temperature and the volatiles were removed in vacuo. The residue was dissolved in EtOAc (500 mL) and the organic solution was washed with water (3×200 mL) followed by brine (1×200 mL). The organic solution was dried (Na$_2$SO$_4$), filtered and concentrated. Purification by medium pressure chromatography (10% EtOAc in hexanes to 25% EtOAc in hexanes) (2 times) provided 5-{3-[2R-(tert-butyl-dimethyl-silanyloxymethyl)-5-oxo-pyrrolidin-1-yl]-prop-1-ynyl}-thiophene-2-carboxylic acid methyl ester (11.42 g). $^1$H NMR (CDCl$_3$) δ 7.61 (d, 1H), 7.09 (d, 1H), 4.81 (d, 1H), 3.98 (d, 1H), 3.87 (m, 1H), 3.85 (s, 3H), 3.78 (dd, 1H), 3.63 (dd, 1H), 2.49-2.29 (m, 2H), 2.11 (m, 1H), 1.82 (m, 1H); 0.85 (s, 9H), 0.03 (s, 6H); MS 408.0 (M+1).

Step C: 5-{3-[2R-(tert-Butyl-dimethyl-silanyloxymethyl)-5-oxo-pyrrolidin-1-yl]-propyl}-thiophene-2-carboxylic acid methyl ester. A mixture of 5-{3-[2R-(tert-butyl-dimethyl-silanyloxymethyl)-5-oxo-pyrrolidin-1-yl]-prop-1-ynyl}-thiophene-2-carboxylic acid methyl ester (11.4 g, 28 mmol) in EtOH (200 mL) was hydrogenated on a Parr shaker at 50 psi in the presence of 10% palladium on carbon (1.2 g) for 3 h. The catalyst was removed by filtration through Celite® (diatomaceous earth, Fluka Chemical Corp, Milwaukee, Wis.) with the aid of EtOH and the organic solution was concentrated in vacuo. The hydrogenation was repeated using EtOH (200 mL) and 10% palladium on carbon (1.2 g) at 50 psi for 24 h. Purification by medium pressure chromatography (25% EtOAc in hexanes to 50% EtOAc in hexanes) provided 5-{3-[2R-(tert-butyl-dimethyl-silanyloxymethyl)-5-oxo-pyrrolidin-1-yl]-propyl}-thiophene-2-carboxylic acid methyl ester (10.2 g). $^1$H NMR (CDCl$_3$) δ 7.64 (d, 1H), 6.83 (d, 1H), 3.87 (s, 3H), 3.64 (m, 3H), 3.13 (m, 1H), 2.86 (t, 2H), 2.51-2.24 (m, 2H), 2.12-1.78 (m, 4H), 0.88 (s, 9H), 0.04 (s, 6H).

Step D: 5-[3-(2R-Hydroxymethyl-5-oxo-pyrrolidin-1-yl)-propyl]-thiophene-2-carboxylic acid methyl ester. To a solution of 5-{3-[2R-(tert-butyl-dimethyl-silanyloxymethyl)-5-oxo-pyrrolidin-1-yl]-propyl}-thiophene-2-carboxylic acid methyl ester (1.5 g, 3.64 mmol) in MeOH (40 mL) was added 1N HCl (18 mL) and the reaction mixture was stirred for 1.5 h. The volatiles were removed in vacuo and the aqueous solution was washed with CH$_2$Cl$_2$ (3×50 mL). The organic solutions were combined, washed with brine, dried (MgSO$_4$), filtered and concentrated. Purification by medium pressure chromatography (5% MeOH in CH$_2$Cl$_2$) provided 5-[3-(2R-hydroxymethyl-5-oxo-pyrrolidin-1-yl)-propyl]-thiophene-2-carboxylic acid methyl ester (689 mg). $^1$H NMR (CDCl$_3$) δ 7.59 (d, 1H), 6.79 (d, 1H), 3.82 (s, 3H), 3.75 (m, 1H), 3.62 (m, 3H), 3.07 (m, 1H), 2.82 (t, 2H), 2.44 (m, 1H), 2.26 (m, 2H), 2.09-1.83 (m, 4H); MS 298.2 (M+1).

Preparation 2

7-(2R-Hydroxymethyl-5-oxo-pyrrolidin-1-yl)-heptanoic acid ethyl ester

Analogous to the procedure described for Preparation 1, Step A, the anion derived from 5R-(tert-butyl-dimethyl-silanyloxymethyl)-pyrrolidin-2-one (18.83 g, 82.1 mmol) and NaHMDS (1M in THF, 90 mL, 90 mmol) was alkylated with ethyl 7-bromoheptanoate (16 mL, 82 mmol). The reaction mixture was stirred at 60° C. for 16 h and was worked-up analogous to that described for Preparation 1, Step A. The crude residue was dissolved in MeOH (600 mL) and 1N HCl (300 mL) was added. The solution was stirred for 3 h and the volatiles were removed in vacuo. The aqueous solution was diluted with CH$_2$Cl$_2$ (300 mL) and the organic solution was washed with water (2×75 mL) followed by brine (1×75 mL). The organic solution was dried (Na$_2$SO$_4$), filtered and concentrated. Purification by medium pressure chromatography (EtOAc) provided 7-(2R-hydroxymethyl-5-oxo-pyrrolidin-1-yl)-heptanoic acid ethyl ester (21.2 g). $^1$H NMR (CDCl$_3$) δ 4.12 (q, 2H), 3.80 (dd, 1H), 3.66 (m, 3H), 2.97 (m, 1H), 2.54-2.27 (m, 5H), 2.04 (m, 2H), 1.67-1.28 (m, 8H), 1.26 (t, 3H); MS 272.3 (M+1).

Preparation 3

7-(2R-Hydroxymethyl-5-oxo-pyrrolidin-1-yl)-heptanenitrile

Analogous to the procedure described for Preparation 1, Step A, the anion derived from 5R-(tert-butyl-dimethyl-silanyloxymethyl)-pyrrolidin-2-one (20 g, 87 mmol) and NaHMDS (1M in THF, 96 mL, 96 mmol) was alkylated with 7-bromoheptanenitrile (13 mL, 87 mmol). The reaction mixture was stirred at 60° C. for 24 h and was worked-up analogous to that described for Preparation 1, Step A. The crude residue was dissolved in MeOH (350 mL) and 1N HCl (154 mL) was added. The solution was stirred for 2 h and the volatiles were removed in vacuo. The aqueous solution was washed with CH$_2$Cl$_2$ (3×200 mL) and the organic solutions were combined and washed with brine (1×150 mL). The organic solution was dried (Na$_2$SO$_4$), filtered and concentrated. Purification by medium pressure chromatography (1% MeOH in EtOAc to 4% MeOH in EtOAc) provided 7-(2R-hydroxymethyl-5-oxo-pyrrolidin-1-yl)-heptanenitrile (10.3 g). $^1$H NMR (CDCl$_3$) δ 3.76 (dd, 1H), 3.62 (m, 3H), 2.97 (m, 1H), 2.43 (m, 1H), 2.33-1.94 (m, 5H), 1.92 (m, 1H), 1.66-1.41 (m, 6H), 1.30 (m, 2H); MS 225.3 (M+1).

Preparation 4

4-(3-Bromo-propyl)-benzoic acid methyl ester

Step A: 4-(3-Hydroxy-prop-1-ynyl)-benzoic acid methyl ester. To a solution of methyl 4-iodobenzoate (20 g, 76 mmol), propargyl alcohol (5.55 g, 99.0 mmol) and triethylamine (20 mL) in acetonitrile (200 mL) was added dichlorobis(triphenylphosphine)palladium(II) (1.55 g, 2.21 mmol), followed by CuI (454 mg, 2.38 mmol). The reaction mixture was stirred at room temperature for 24 h. Water was added and the aqueous solution was washed with EtOAc (3×). The organic solutions were combined, dried (MgSO$_4$), filtered and concentrated. Purification by medium pressure chromatography (9:1 hexanes:EtOAc to 4:1 hexanes:EtOAc) provided 4-(3-hydroxy-prop-1-ynyl)-benzoic acid methyl ester (12.65 g).

Step B: 4-(3-Hydroxy-propyl)-benzoic acid methyl ester. A solution of 4-(3-hydroxy-prop-1-ynyl)-benzoic acid methyl ester (12.65 g) in EtOAc (75 mL) and MeOH (75 mL) was hydrogenated at 50 psi on a Parr shaker in the presence of 10% palladium on carbon (2 g) for 24 h. The catalyst was removed by filtration through Celite® and the filtrate was concentrated. The reaction was repeated by adding 10% palladium on carbon (2 g) and hydrogenating on a Parr shaker for 24 h. After filtering through Celite®, the solution was concentrated in vacuo to provide 4-(3-hydroxy-propyl)-benzoic acid methyl ester (11.98 g).

Step C: 4-(3-Bromo-propyl)-benzoic acid methyl ester. A solution of 4-(3-hydroxy-propyl)-benzoic acid methyl ester (11.98 g) and 1,1'-carbonyldiimidazole (9.0 g, 55.50 mmol) in CH$_3$CN (200 mL) was stirred at room temperature for 1.5 h. Allyl bromide (20 mL) was added and the reaction mixture was heated under reflux for 20 h. The reaction mixture was cooled to room temperature and saturated aqueous NaHCO$_3$ was added. The aqueous solution was washed with EtOAc (3×) and the organic solutions were combined, dried (MgSO$_4$), filtered and concentrated. Purification by medium pressure chromatography (9:1 hexanes:EtOAc) provided the title compound of Preparation 4.

Preparation 5

2-[3-(2R-Hydroxymethyl-5-oxo-pyrrolidin-1-yl)-propyl]-thiazole-4-carboxylic acid ethyl ester Step A: 2-Bromo-thiazole-4-carboxylic acid ethyl ester. A cold solution of sodium nitrite (228 mg, 3.31 mmol) in water (2.0 mL) was added dropwise to a mixture of 2-amino-thiazole-4-carboxylic acid ethyl ester (J. Am. Chem. Soc., 1946, 68, 266) (500 mg, 2.90 mmol), CuSO$_4$ pentahydrate (2.100 g, 8.41 mmol), NaBr (1.134 g, 11.02 mmol), H$_2$SO$_4$ (3.0 mL)

and water (3.0 mL) at −5° C. to 0° C. The reaction mixture was stirred at 0° C. for 20 minutes and at room temperature for 1 h. The reaction mixture was adjusted to pH 9 with 1N NaOH (105 mL) and the aqueous solution was washed with CHCl$_3$ (4×50 mL). The organic solutions were combined, dried (MgSO$_4$), filtered and concentrated. Purification by medium pressure chromatography (39:1 hexanes:EtOAc to 19:1 hexanes:EtOAc) provided 2-bromo-thiazole-4-carboxylic acid ethyl ester (257 mg).

Step B: 2-{3-[2R-(tert-Butyl-dimethyl-silanyloxymethyl)-5-oxo-pyrrolidin-1-yl]-prop-1-ynyl}-thiazole-4-carboxylic acid ethyl ester. Substituting the appropriate starting materials, the compound of Step B was prepared using an analogous procedure to that described for Preparation 4, Step A using tetrakis(triphenylphosphine) palladium(0) and copper (I) iodide, CuI as catalysts.

Step C: 2-{3-[2R-(tert-Butyl-dimethyl-silanyloxymethyl)-5-oxo-pyrrolidin-1-yl]-propyl}-thiazole-4-carboxylic acid ethyl ester. Substituting the appropriate starting materials, the compound of Step C was prepared using an analogous procedure to that described for Preparation 4, Step B.

Step D: 2-[3-(2R-Hydroxymethyl-5-oxo-pyrrolidin-1-yl)-propyl]-thiazole-4-carboxylic acid ethyl ester. To a solution of 2-{3-[2R-(tert-butyl-dimethyl-silanyloxymethyl)-5-oxo-pyrrolidin-1-yl]-propyl}-thiazole-4-carboxylic acid ethyl ester (306 mg, 0.717 mmol) in THF (20 mL) at 0° C. was slowly added Bu$_4$NF (1M in THF, 1.1 mL, 1.1 mmol). The reaction mixture was warmed to room temperature and was stirred for 2 h. Aqueous saturated NaHCO$_3$ was added and the volatiles were concentrated in vacuo. The aqueous solution was washed with CHCl$_3$ (4×10 mL). The organic solutions were combined, dried (MgSO$_4$), filtered and concentrated to provide the title compound of Preparation 5 (225 mg).

Preparation 6

[3-(4-Fluoro-3-methyl-phenyl)-2-oxo-propyl]-phosphonic acid diethyl ester

Step A: [3-(4-Fluoro-3-methyl-phenyl)-2-hydroxy-propyl]-phosphonic acid diethyl ester. To a solution of 4-fluoro-3-methylphenylmagnesium bromide (0.5M in Et$_2$O, 15.5 mL, 7.75 mmol) in THF (10 mL) at −30° C. was added copper (I) iodide, CuI (196 mg, 1.03 mmol) and the reaction mixture was stirred for 10 minutes. The reaction mixture was warmed to −15° C. and oxiranylmethyl-phosphonic acid diethyl ester (1 g, 5.2 mmol) in THF (10 mL) was added. The reaction mixture was stirred at 0° C. for 2 h. Saturated aqueous ammonium chloride was added and the product was extracted into EtOAc. The organic solution was dried (MgSO$_4$), filtered and concentrated. Purification by medium pressure chromatography (20% EtOAc in hexanes to 70% EtOAc in hexanes) provided [3-(4-fluoro-3-methyl-phenyl)-2-hydroxy-propyl]-phosphonic acid diethyl ester (1.37 g).

Step B: [3-(4-Fluoro-3-methyl-phenyl)-2-oxo-propyl]-phosphonic acid diethyl ester. To a solution of [3-(4-fluoro-3-methyl-phenyl)-2-hydroxy-propyl]-phosphonic acid diethyl ester (1.37 g, 4.51 mmol) in CH$_2$Cl$_2$ (30 mL) was added Dess-Martin reagent (Dess-Martin periodinane, Aldrich Chemical Co., Milwaukee, Wis., 2.10 g, 4.96 mmol). The reaction mixture was stirred at room temperature for 2 h and additional CH$_2$Cl$_2$ was added. The organic solution was washed with NaHCO$_3$ (2 times) and once with brine. The organic solution was dried (MgSO$_4$), filtered and concentrated. Purification by medium pressure chromatography (20% EtOAc in hexanes to 70% EtOAc in hexanes) provided the title compound of Preparation 6 (1.1 g).

Preparation 7

[3-(3-Methoxymethyl-phenyl)-2-oxo-propyl]-phosphonic acid diethyl ester

Substituting the appropriate starting materials, the title compound of Preparation 7 was prepared following an analogous procedure to that described for Preparation 6.

Preparation 8

[3-(4-Ethyl-phenyl)-2-oxo-propyl]-phosphonic acid diethyl ester

Substituting the appropriate starting materials, the title compound of Preparation 8 was prepared following an analogous procedure to that described for Preparation 6.

Preparation 9

{3-[3-(2-Methoxy-ethyl)-phenyl]-2-oxo-propyl}-phosphonic acid diethyl ester

Substituting the appropriate starting materials, the title compound of Preparation 9 was prepared following an analogous procedure to that described for Preparation 6.

Preparation 10

[2-Oxo-3-(3-trifluoromethyl-phenyl)-propyl]-phosphonic acid dimethyl ester

Step A: N-Methoxy-N-methyl-2-(3-trifluoromethyl-phenyl)-acetamide. To a solution of N,O-dimethylhydroxylamine hydrochloride (1.577 g, 16.2 mmol) in DMF (25 mL) and CH$_2$Cl$_2$ (25 mL) at 0° C. was added triethylamine (2.25 mL). After stirring for 5 minutes, 3-trifluoromethylphenyl acetic acid (3.0 g, 14.7 mmol), HOBT (3.177 g, 23.5 mmol), and EDC (3.10 g, 16.2 mmol) were added. The reaction mixture was stirred at room temperature for 18 h and was concentrated in vacuo. The residue was diluted with EtOAc and the organic solution was washed consecutively with 1N NaOH (2 times), water, and brine. The organic solution was dried (MgSO$_4$), filtered and concentrated in vacuo. Medium pressure chromatography (20% EtOAc in hexanes to 50% EtOAc in hexanes) provided N-methoxy-N-methyl-2-(3-trifluoromethyl-phenyl)-acetamide.

Step B: [2-Oxo-3-(3-trifluoromethyl-phenyl)-propyl]-phosphonic acid dimethyl ester. To a solution of dimethyl methylphosphonate (9.4 g, 75.8 mmol) in toluene (80 mL) at −78° C. was slowly added n-BuLi (2.5M in hexanes, 28 mL, 70 mmol). The reaction mixture was stirred for 1 h and a solution of N-methoxy-N-methyl-2-(3-trifluoromethyl-phenyl)-acetamide (14.39 g) in toluene (50 mL) was slowly added. The reaction mixture was stirred for 2.5 h and AcOH (40 mL) was added. The reaction mixture was warmed to room temperature and water was added. The organic layer was washed with water followed by brine. The organic solution was dried (MgSO$_4$), filtered and concentrated in vacuo. Medium pressure chromatography (CH$_2$Cl$_2$ to 2% MeOH in CH$_2$Cl$_2$) provided the title compound of Preparation 10 (9.37 g). $^1$H NMR (CDCl$_3$) δ7.52 (m, 1H), 7.44 (m, 2H), 7.37 (m, 1H), 3.96 (s, 2H), 3.87 (s, 3H), 3.76 (s, 3H), 3.12 (d, 2H).

Preparation 11

[3-(3-Chloro-phenyl)-2-oxo-propyl]-phosphonic acid dimethyl ester

Substituting the appropriate starting materials, the title compound of Preparation 11 was prepared following an analogous procedure to that described for Preparation 10.

Preparation 12

[3-(3-Bromo-phenyl)-2-oxo-propyl]-phosphonic acid dimethyl ester

Substituting the appropriate starting materials, the title compound of Preparation 12 was prepared following an analogous procedure to that described for Preparation 10.

Preparation 13

[2-Oxo-3-(3-trifluoromethoxy-phenyl)-propyl]-phosphonic acid dimethyl ester

Substituting the appropriate starting materials, the title compound of Preparation 13 was prepared following an analogous procedure to that described for Preparation 10. MS 327.1 (M+1), 325.1 (M−1).

Preparation 14

[3-(3-Chloro-phenyl)-2-oxo-propyl]-phosphonic acid dimethyl ester

To a solution of dimethyl methylphosphonate (17.93 g, 144 mmol) in THF (270 mL) at −78° C. was slowly added n-BuLi (2.5M, 64.2 mL, 160.6 mmol). The reaction mixture was stirred for 1 h and (3-chloro-phenyl)-acetic acid methyl ester (26.93 g, 146 mmol) was slowly added. The reaction mixture was allowed to warm to room temperature and was stirred for 24 h. Acetic acid (15 mL) was added and the volatiles were removed in vacuo. The residue was diluted with $CH_2Cl_2$ and the organic solution was washed carefully with saturated aqueous $NaHCO_3$ (3 times). The organic layer was dried ($MgSO_4$), filtered and concentrated in vacuo. Purification by medium pressure chromatography (20% EtOAc in hexanes to EtOAc) provided the title compound (9.28 g).

Preparations 15-24

Substituting the appropriate starting materials, the following phosphonates (Preparations 15-24) were prepared in an analogous fashion to the procedure described for Preparation 14.

Preparation 15: [3-(3-Fluoro-phenyl)-2-oxo-propyl]-phosphonic acid dimethyl ester Preparation 16: [3-(4-Fluoro-phenyl)-2-oxo-propyl]-phosphonic acid dimethyl ester Preparation 17: [3-(4-Chloro-phenyl)-2-oxo-propyl]-phosphonic acid dimethyl ester Preparation 18: (3-Naphthalen-2-yl-2-oxo-propyl)-phosphonic acid dimethyl ester Preparation 19: (2-Oxo-3-thiophen-2-yl-propyl)-phosphonic acid dimethyl ester Preparation 20: (3-Cyclohexyl-2-oxo-propyl)-phosphonic acid dimethyl ester Preparation 21: (2-Oxo-3-phenyl-propyl)-phosphonic acid dimethyl ester Preparation 22: (3-Benzo[1,3]dioxol-5-yl-2-oxo-propyl)-phosphonic acid dimethyl ester Preparation 23: [2-Oxo-3-(3-phenoxy-phenyl)-propyl]-phosphonic acid dimethyl ester Preparation 24: [2-Oxo-3-(2-trifluoromethyl-phenyl)-propyl]-phosphonic acid dimethyl ester

Preparation 25

(3-Biphenyl-3-yl-2-oxo-propyl)-phosphonic acid dimethyl ester

Step A: Biphenyl-3-yl-acetic acid methyl ester. A mixture of phenylboronic acid (1.000 g, 8.20 mmol), methyl 3-bromophenylacetate (1.691 g, 7.38 mmol), $Na_2CO_3$ (1.738 g, 16.4 mmol), tetrakis(triphenylphosphine)palladium(0) (0.474 g, 0.41 mmol), toluene (30 mL), and water (5 mL) was heated under reflux for 20 h. The reaction mixture was diluted with water (20 mL) and the volatiles were removed in vacuo. The aqueous solution was washed with EtOAc (4×20 mL). The organic solutions were combined, washed with 1N NaOH (15 mL) followed by water (15 mL). The organic solution was dried ($MgSO_4$), filtered and concentrated in vacuo. Purification by medium pressure chromatography (79:1 hexanes:EtOAc to 39:1 hexanes:EtOAc) provided biphenyl-3-yl-acetic acid methyl ester (1.316 g).

Step B: (3-Biphenyl-3-yl-2-oxo-propyl)-phosphonic acid dimethyl ester. The title compound of Preparation 25 was prepared from biphenyl-3-yl-acetic acid methyl ester of Step A following an analogous procedure as described for Preparation 14.

Preparation 26

Tetrahydro-pyrrolizine-3,5-dione

The title compound of Preparation 26 was prepared following the procedure described in U.S. Pat. No. 4,663,464.

In Vitro Assays

The compounds of Formula I, which are useful in the methods of the present invention, bind to the prostaglandin $E_2$ type 4 receptor ($EP_4$ receptor). The full length coding sequence for the human $EP_1$ receptor is made in accordance with the procedure in Funk et al., Journal of Biological Chemistry, 1993, 268, 26767-26772. The full length rat $EP_2$ receptor is made in accordance with the procedure in Nemoto et al., *Prostaglandins and other Lipid Mediators*, 1997, 54, 713-725. The full length coding sequence for the human $EP_3$ receptor is made in accordance with the procedure in Regan et al., British Journal of Pharmacology, 1994, 112, 377-385. The full length coding sequence for the rat $EP_4$ receptor is made in accordance with the procedure in Sando et al., Biochem. Biophys. Res. Comm. 1994, 200, 1329-1333. These full length receptors are used to prepare 293S cells expressing the human $EP_1$, rat $EP_2$, human $EP_3$ or rat $EP_4$ receptors.

Human $EP_1$, Rat $EP_2$, Human $EP_3$, Rat $EP_4$ Receptor Binding Assay

The full length receptors described above are used to prepare 293S cells expressing the $EP_1$, $EP_2$, $EP_3$, and $EP_4$ receptors.

293S cells expressing either the human $EP_1$, rat $EP_2$, human $EP_3$ or rat $EP_4$ prostaglandin $E_2$ receptors are generated according to methods known to those skilled in the art. Typically, PCR (polymerase chain reaction) primers corresponding to the 5' and 3' ends of the published full length receptor are made according to the well known methods disclosed above and are used in an RT-PCR (reverse transcriptase-polymerase chain reaction) reaction using the total RNA from human kidney (for $EP_1$), rat kidney (for $EP_2$), human lung (for $EP_3$), or rat kidney ($EP_4$) as a source. PCR products are cloned by the TA overhang method into pCR2.1 (Invitrogen Corporation, Carlsbad, Calif.) and identity of the cloned receptor is confirmed by DNA sequencing. For expression of the rat $EP_2$ receptor, the confirmed cDNA is subcloned into the mammalian expression vector PURpCI, a vector generated by subcloning the selectable marker for puromycin resistance into the mammalian expression vector pCI (Promega, Madison, Wis.)

293S cells are transfected with either the cloned human $EP_1$ or $EP_3$ receptor in pcDNA3 by electroporation. Stable cell lines expressing either the human $EP_1$ or $EP_3$ receptor are established following selection of transfected cells with G418. 293S cells are transfected with the cloned rat $EP_2$ receptor in PURpCi by lipid mediated transfection. Stable cell lines expressing the rat $EP_2$ receptor are established following selection of transfected cells with puromycin. 293S cells are transfected with the cloned rat $EP_4$ receptor in pcDNA3 by lipid mediated transfection. Stable cell lines expressing the rat $EP_4$ receptor are established following selection of transfected cells with Geneticin® (Invitrogen, Carlsbad, Calif.).

Clonal cell lines expressing the maximal number of receptors are chosen following a whole cell $^3H$-$PGE_2$ binding assay using unlabeled $PGE_2$ as a competitor.

Membrane Preparation: All operations are performed at 4° C. Transfected cells expressing either prostaglandin $E_2$ type 1, type 2, type 3, or type 4 ($EP_1$, $EP_2$, $EP_3$, or $EP_4$, respectively) receptors are harvested and suspended to 2 million cells per ml in Buffer A [50 mM Tris-HCl (pH 7.4), 10 mM $MgCl_2$, 1 mM EDTA, 1 mM Pefabloc peptide, (Boehringer Mannheim Corp., Indianapolis, Ind.), 10 uM Phosporamidon peptide, (Sigma, St. Louis, Mo.), 1 uM pepstatin A peptide, (Sigma, St. Louis, Mo.), 10 uM elastatinal peptide, (Sigma, St. Louis, Mo.), 100 uM antipain peptide, (Sigma, St. Louis, Mo.)]. The cells are lysed by sonication with a Branson Sonifier (Branson Ultrasonics Corporation, Danbury, Conn.) in 2 fifteen second bursts. Unlysed cells and debris are removed by centrifugation at 100×g for 10 min. Membranes are then harvested by centrifugation at 45,000×g for 30 minutes. Pelleted membranes are resuspended to 3-10 mg protein per ml, protein concentration being determined of the method of Bradford [Bradford, M., Anal. Biochem. 1976, 72, 248]. Resuspended membranes are then stored frozen at –80° C. until use.

Binding Assay: Frozen membranes prepared as above are thawed and diluted to 1 mg protein per ml in Buffer A above. 100 µl of the cell membrane preparation is mixed with 5 µl of a solution of test compound of Formula I (diluted in DMSO to a concentration 40 times the desired final concentration) and 95 µl of 3 nM $^3H$-prostaglandin $E_2$ (Amersham, Arlington Heights, Ill.) in Buffer A. The mixture (200 µL total volume) is incubated for 1 hour at 25° C. The membranes are then recovered by filtration through type GF/C glass fiber filters (Wallac, Gaithersburg, Md.) using a Tomtec harvester (Tomtec, Orange, Conn.). The membranes with bound $^3H$-prostaglandin $E_2$ are trapped by the filter, while the buffer and unbound $^3H$-prostaglandin $E_2$ pass through the filter into waste. Each sample is then washed 3 times with 3 ml of [50 mM Tris-HCl (pH 7.4), 10 mM $MgCl_2$, 1 mM EDTA]. The filters are then dried by heating in a microwave oven. To determine the amount of $^3H$-prostaglandin bound to the membranes, the dried filters are placed into plastic bags with scintillation fluid and counted in a LKB 1205 Betaplate reader (Wallac, Gaithersburg, Md.). $IC_{50}$s are determined from the concentration of test compound required to displace 50% of the specifically bound $^3H$-prostaglandin $E_2$.

Determination of Cyclic AMP Elevation in 293S Cell Lines Stably Overexpressing Recombinant Rat $EP_4$ Receptors Assay cDNA representing the complete open reading frame of the rat $EP_4$ receptor is generated by reverse transcriptase polymerase chain reaction using oligonucleotide primers based on published sequences. The full length coding sequence for the rat $EP_4$ receptor is made in accordance with the procedure in Sando et al., Biochem. Biophys. Res. Comm. 1994, 200, 1329-1333, and RNA from rat kidney ($EP_4$) as templates. 293S cells are transfected with the cloned rat $EP_4$ receptor in pcDNA3 by lipid mediated transfection. Stable cell lines expressing the rat $EP_4$ receptor are established following selection of transfected cells with Geneticin® (Invitrogen Corporation, Carlsbad, Calif.).

Clonal cell lines expressing the maximal number of receptors are chosen following a whole cell $^3H$-$PGE_2$ binding assay using unlabeled $PGE_2$ as a competitor. Transfectants demonstrating high levels of specific [$^3H$]$PGE_2$ binding are further characterized by Scatchard analysis to determine $B_{max}$ and $K_d$s for $PGE_2$. The lines selected for compound screening have approximately 256,400 receptors per cell and a $K_d$=2.9 nm for $PGE_2$ ($EP_4$). Constitutive expression of the receptor in parental 293-S cells is negligible. A stable cell line containing the rat $EP_4$ receptor is grown in Dulbecco's Mosified Eagle Medium/F12 (DMEM/F12) containing 10% fetal bovine serum and G418 (500 µg/ml) to 80% confluency.

cAMP responses in the 293-S/$EP_4$ lines are determined by detaching cells from culture flasks in 1 ml of calcium (Ca++) and magnesium (Mg++) deficient phosphate buffered saline (PBS) via vigorous pounding and then rinsing the cells with calcium (Ca++) and magnesium (Mg++) deficient phosphate buffered saline (PBS). The cells are resuspended in MEM (Minimum Essential Medium), 1% BSA (bovine serum albumin), 50 mM HEPES (N-[2-Hydroxyethyl]piperazine-N'-[2-ethanesulfonic acid]) at 37° C. The cell suspension is counted on a hemacytometer and diluted by adding MEM (Minimum Essential Medium) to a final concentration of 1×10$^6$ cells/ml, and adding 3-isobutyl-1-methylxanthine (IBMX) to a final concentration of 1 mM. 200 microliters of cell suspension is immediately aliquoted into individual tubes and incubated for 10 minutes, uncovered, at 37° C., 5% $CO_2$, 95% relative humidity. The compound of Formula I to be tested in either dimethylsulfoxide (DMSO) or ethanol is then added to cells at 1:100 dilutions such that the final DMSO or ethanol concentration is 1%. Typically, the cells are treated with 6-8 different concentrations (in 1 log increments, such as those described below) of the compound of Formula I. Typical concentrations of the compound of Formula I in this assay are between $10^{-5}$M to $10^{-10}$M. For example, a six point compound dose response assay tests the compound of Formula I at concentrations of $10^{-5}$M, $10^{-6}$M, $10^{-7}$M, $10^{-8}$M, $10^{-9}$M and $10^{-10}$M. Immediately after adding the test compound, the tubes are covered, mixed by inverting two times, and incubated at 37° C. for 12 minutes. Samples are then lysed by incubation at 100° C. for 10 minutes and immediately cooled on ice for 5 minutes to approximately 4° C. Cellular debris is pelleted by centrifugation at 3500×g for 5 minutes at approximately 4° C., and cleared lysates are transferred to fresh tubes. cAMP concentrations are determined using a commercially available $^{125}$I-cAMP radioimmunoassay (RIA) kit (NEK-033, Perkin-Elmer Life Sciences, Inc., Boston, Mass.). The cleared lysates are diluted 1:100 in cAMP RIA assay buffer (included in kit) and centrifuged again. 50 microliters of the resulting supernatant is transferred to a 12×75 mm glass tube and data is collected by scintillation counting using a Wallac Cobra II Gamma Counter (Perkin-Elmer Wallac, Inc., Gaithersburg, Md.). $EC_{50}$ calculations are performed on a calculator using linear regression analysis on the linear portion of the dose response curves or using Data Fitter.

In Vivo Assays

The selective $EP_4$ receptor agonists of Formula I can be evaluated in various in vivo liver failure models known in the art, such as the in vivo rat liver failure model as disclosed by Kasai, K. et al. in Gastroenterology 2001, 120 (suppl. 1), A-541.

In Vivo Acute Liver Injury Model

Methods: Acute liver failure in rats can be induced by intraperitoneal injection of one of carbon tetrachloride ($CCl_4$, 1 mg/kg), dimethylnitrosamine (DMN, 50 mg/kg), D-galactosamine (D-gal, 1 g/kg), or D-galactosamine with lipopolysaccharide (LPS), (D-gal, 1 g/kg; LPS 100 µg/kg). Immediately following the intaperitoneal injection of carbon tetrachloride, dimethyinitrosamine, D-galactosamine, or D-galactosamine with lipopolysaccharide, the test compound of Formula I or saline (as control) is administered. The test compound (a selective $EP_4$ receptor agonist of Formula I) can be administered at various doses such as 0.01, 0.05, 0.1 or 0.2 mg/kg. 24 hours after administration of the test compound of Formula I, the liver can be removed for histology and serum can be obtained for determination of total bilirubin (T-bil), aspartate aminotransferase (AST), and alanine aminotransferase (ALT). Massive hepatic necrosis with marked elevations in the levels of T-bil, AST, and ALT was observed in the saline treated control group. The effectiveness of the test compound in the above models can be determined by comparison of histology and serum results obtained for the animals treated with the test compound with the corresponding results from the saline control group.

The following in vivo anesthetized rabbit model is used in order to demonstrate the hypotensive effect of the compounds of Formula I (e.g., Example 3).

In Vivo Rabbit Model

Methods: New Zealand White male rabbits (3-4 kg) are anesthetized with sodium pentobarbital (30 mg/kg, i.v.) and a surgical plane of anesthesia is maintained by a continuous infusion of sodium pentobarbital (16 mg/kg/hr) via an ear vein catheter. A tracheotomy is performed through a ventral midline cervical incision and the rabbits are ventilated with 100% oxygen using a positive pressure ventilator. Body temperature is maintained at 38.5° C. using a heating pad connected to a YSI temperature controller model 72 (Yellow Springs Instruments, Yellow Springs, Md.). Fluid-filled catheters are placed in the right jugular vein (for intravenous drug administration) and in the right carotid artery for arterial pressure monitoring and for blood gas analysis using a model 248 blood gas analyzer (Bayer Diagnostics, Norwood, Mass.). The ventilator is adjusted as needed to maintain blood pH and $pCO_2$ within normal physiological ranges for rabbits. Arterial pressure is measured using a strain gauge transducer (Spectromed, Oxnard, Calif.), previously calibrated using a mercury manometer, positioned at the level of the heart and connected to the arterial catheter. Arterial pressure signals are digitized at 500 Hz and analyzed using a Po—Ne-Mah Data Acquisition System (Gould Instrument Systems, Valley View, Ohio) to obtain mean arterial pressure and heart rate values. Baseline values are collected when mean arterial pressure and heart rate have stabilized. The test compound (Compound of Formula I) is then administered either as a subcutaneous (SC) bolus or as an intravenous (IV) infusion. For subcutaneous (SC) dosing the test compound can be dissolved in an appropriate vehicle such as 5% ethanol in water (5% EtOH 95% $H_2O$), while for intravenous dosing the test compound can be dissolved in an appropriate vehicle such as 0.9% normal saline. Arterial pressure and heart rate are monitored continuously for 4 hours following dosing of the test compound or for the duration of a continuous 4 hour infusion of the test compound. Blood is sampled after dosing or during the infusion of the test compound to determine plasma concentrations of the test compounds.

Data Analysis: Data are presented as mean values. The hemodynamic data (heart rate and mean arterial pressure) are collected over 4 hours post-dosing in all groups and the reported value is the average value over the 5-minute interval prior to the selected time.

The following in vivo primate model is used in order to demonstrate the hypotensive effect of the compounds of Formula I in primates (e.g., Example 4).

In Vivo Primate Model

Methods: Adult *M. fascicularis* primates (6-8 kg) that have been previously instrumented with subcutaneous vascular access ports in the descending thoracic aorta and conditioned to sit quietly in specially designed primate-restraining chairs are used. All primates are fasted for 12-18 hours prior to the experiment. On the day of the experiment, with the primates restrained in the chairs, a strain gauge pressure transducer (Spectromed, Oxnard, Calif.), previously calibrated using a mercury manometer, is positioned at the level of the heart and connected to the vascular access port to measure arterial pressure. The primates are allowed to acclimate to the chair for at least one hour. Arterial pressure signals are digitized at 500 Hz and continuously recorded throughout the experiment and analyzed using a Po—Ne-Mah Data Acquisition System (Gould Instrument Systems, Valley View, Ohio) to obtain the measurements of mean arterial pressure and heart rate. Baseline values are collected when the primates are sitting calmly and when mean arterial pressure and heart rate have stabilized. The test compound (Compound of Formula I) is then administered as a subcutaneous (SC) bolus of a solution of the test compound in an appropriate vehicle such as 5% ethanol in water (5% EtOH 95% $H_2O$). The solution of test compound or vehicle is filtered through a 0.22 micron filter prior to injection and a typical dosing volume is 0.2 ml/kg. Arterial pressure and heart rate are monitored continuously for 4 hours following dosing of the test compound and are recorded at selected time intervals for data comparison (vehicle vs test compound). Blood samples (1.5 ml) are withdrawn to determine plasma concentrations of the test compound and withdrawn blood is immediately replaced with 0.9% sterile saline to maintain blood volume.

Data Analysis: Data are presented as mean values. The hemodynamic data (heart rate and mean arterial pressure) are collected over 4 hours post-dosing in all groups and the reported value is the average value over the 5-minute interval prior to the selected time.

EXAMPLE 1

The Human $EP_1$, Rat $EP_2$, Human $EP_3$, Rat $EP_4$ Receptor Binding Assay, described hereinabove, was used in order to demonstrate the binding of 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M) to the human $EP_1$, rat $EP_2$, human $EP_3$, and rat $EP_4$ receptors. 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M) was run in the assay described and the following $IC_{50}$s were obtained. $IC_{50}$s: human $EP_1$ receptor, >1000 nm; rat $EP_2$ receptor, 463 nm; human $EP_3$ receptor, >1000 nm; and rat $EP_4$ receptor, 11 nm. These results show that 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M) binds selectively to the rat $EP_4$ receptor in the assay described.

EXAMPLE 2

The cyclic AMP Elevation in 293S Cell Lines Stably Overexpressing Recombinant Rat $EP_4$ Receptors Assay, described hereinabove, was used in order to demonstrate the effect of 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M). 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M) was run in the assay described and an $EC_{50}$ of 0.6 nm was obtained.

EXAMPLE 3

The in vivo rabbit model, described hereinabove, was used in order to demonstrate the hypotensive effect of 5-(3-{2S-[3R-Hydroxy-4-(3-trifluoromethyl-phenyl)-butyl]-5-oxo-pyrrolidin-1-yl}-propyl)-thiophene-2-carboxylic acid (Compound 3M, sodium salt), at the dosages described below. 5-(3-{2S-[3R-Hydroxy-4-(3-trifluoromethyl-phenyl)-butyl]-5-oxo-pyrrolidin-1-yl}-propyl)-thiophene-2-carboxylic acid sodium salt (Compound 3M, sodium salt) was administered according to the previously described method either as a subcutaneous (SC) bolus (in 5% ethanol in water) or as an intravenous (IV) infusion (in 0.9% normal saline).

Compound: The test compound, 5-(3-{2S-[3R-Hydroxy-4-(3-trifluoromethyl-phenyl)-butyl]-5-oxo-pyrrolidin-1-yl}-propyl)-thiophene-2-carboxylic acid sodium salt (Compound 3M, sodium salt), was adjusted for active compound (mgA) and dissolved in the stated vehicle at the following concentrations: For Group A, 5 mgA/ml in 5% EtOH: 95% $H_2O$; for Group B; approximately 0.1 mgA/ml in 0.9% normal saline; for Group C; approximately 0.01 mgA/ml in 0.9% normal saline (tenfold dilution of the Group B solution with 0.9% saline); and for Group D; approximately 0.001 mgA/ml in 0.9% normal saline (tenfold dilution of the Group C solution with 0.9% saline). Thus, dosing volumes were 0.2 ml/kg (Group A) subcutaneously or 5 ml/h (Groups B, C, and D) as an intravenous (IV) infusion. The term "mgA" means the number of milligrams adjusted for active compound (e.g. corrected for salt etc.).

Dosing: Four groups (Groups A, B, C, and D) of two rabbits each were dosed as follows.

Group A (2 rabbits) received Compound 3M, as its sodium salt, in vehicle (5% EtOH:95% $H_2O$) as a subcutaneous (SC) bolus, at 1 mgA/kg (0.2 ml/kg of the 5 mgA/ml solution described above).

Group B (2 rabbits) received Compound 3M, as its sodium salt, in vehicle (approximately 0.1 mgA/ml in 0.9% normal saline solution, described above), infused intravenously (IV) at 167 µg/kg/hr for 4 hours at 5 ml/hr.

Group C (2 rabbits) received Compound 3M, as its sodium salt, in vehicle (approximately 0.01 mgA/ml in 0.9% normal saline solution, described above) infused IV at 16.7 µg/kg/hr for 4 hours at 5 ml/hr.

Group D (2 rabbits) received Compound 3M, as its sodium salt, in vehicle (approximately 0.001 mgA/ml in 0.9% normal saline solution, described above) infused IV at 1.67 µg/kg/hr for 4 hours at 5 ml/hr.

Data analysis was carried out as described in the general in vivo rabbit model procedure, hereinabove, and is provided for Groups A, B, C, and D in Tables 1-4, respectively.

Results:

Group A: The administration of Compound 3M sodium salt at 1 mgA/kg SC, as described above, caused an increase in heart rate and a decrease in mean arterial pressure (hypotension) that was rapid in onset (<2 minutes) and was sustained over the entire 4 hour post-dose interval (see Table 1).

Group B: The administration of Compound 3M sodium salt at 167 µg/kg/h IV, as described above, caused an increase in heart rate and a decrease in mean arterial pressure (hypotension) that was rapid in onset (<2 minutes) and was sustained over the entire 4 hour post-dose interval (see Table 2).

Group C: The administration of Compound 3M sodium salt at 16.7 µg/kg/h IV, as described above, caused a slight increase in the heart rate and a slight decrease in mean arterial pressure (hypotension), (see Table 3).

Group D: The administration of Compound 3M sodium salt at 1.67 µg/kg/h, as described above, resulted in no significant change in either heart rate or mean arterial pressure over the duration of the 4 hour IV infusion (no significant hemodynamic effects were observed), (see Table 4).

EXAMPLE 4

The in vivo primate model, described hereinabove, was used in order to demonstrate the hypotensive effect of 5-(3-{2S-[3R-Hydroxy-4-(3-trifluoromethyl-phenyl)-butyl]-5-oxo-pyrrolidin-1-yl}-propyl)-thiophene-2-carboxylic acid sodium salt (Compound 3M, sodium salt), at the dosages described below. The test compound (Compound 3M, sodium salt) was administered subcutaneously (SC) as a solution in 5% ethanol in water (5% EtOH:95% $H_2O$). The dose volume for compound solution or vehicle control was 0.2 ml/kg administered as a SC bolus.

Compound: The test compound, 5-(3-{2S-[3R-Hydroxy-4-(3-trifluoromethyl-phenyl)-butyl]-5-oxo-pyrrolidin-1-yl}-propyl)-thiophene-2-carboxylic acid sodium salt (Compound 3M, sodium salt), was adjusted for active compound (mgA) and dissolved in vehicle (5% EtOH, 95% $H_2O$) at a concentration of 5 mgA/ml for Group A, and 0.5 mgA/ml for Group C. Group B received vehicle (5% EtOH, 95% $H_2O$) as a control.

Dosing: Three groups of monkeys (A, B, and C) were dosed as follows.

Group A: Three male monkeys received Compound 3M, as its sodium salt, in vehicle (5% EtOH:95% $H_2O$) SC, at 1 mgA/kg (0.2 ml/kg of the 5 mgA/ml solution described above).

Group B: Three male monkeys received vehicle (5% EtOH:95% $H_2O$) at 0.2 ml/kg.

Group C: Two of the previously vehicle-treated monkeys (from Group B) received Compound 3M, as its sodium salt, in vehicle (5% EtOH:95% $H_2O$) SC, at 0.1 mgA/kg (0.2 ml/kg of the 0.5 mgA/ml solution described above).

Data analysis was carried out as described in the general in vivo primate model procedure, hereinabove, and is provided for Groups C and B in Tables 5-6, respectively.

Results:

Group A: The administration of Compound 3M, sodium salt, at 1 mgA/kg SC, in three monkeys as described above, resulted in a transient increase in heart rate and a decrease in mean arterial pressure (hypotension) that was rapid in onset (<2 minutes) and was sustained over the 4 hours post-dose. The maximum hypotensive effect could not be determined as treatment, including tilting to reclining position, was required for all three monkeys to maintain the mean arterial pressure above 40 mmHg (considered the minimum required for organ perfusion). The monkeys were gradually returned to an upright seated position over the course of the study as their mean arterial pressure allowed (over 30-210 minutes).

Group B: The administration of vehicle, (5% EtOH:95% $H_2O$) at 0.2 ml/kg, SC, in three monkeys did not substantially affect mean arterial pressure (MAP) or heart rate (HR) over the 4 hours post dose (see Table 6).

Group C: The administration of Compound 3M, sodium salt, at 0.1 mgA/kg SC, in 2 monkeys as described above, resulted in a transient increase in heart rate that returned toward normal but leveled off and remained elevated over the 4 hours post-dose. The administration of Compound 3M, sodium salt, at 0.1 mg/kg SC also caused a decrease in mean arterial pressure (hypotension) that was rapid in onset (<4 minutes) and was sustained over the 4 hours post-dose (see Table 5). Initially, the mean arterial pressure leveled off above 40 mmHg for both monkeys. However, 1 monkey required a full tilt to a reclining position at 75 minutes post-dose, when his pressure fell below 40 mmHg, and was returned to a full upright position by 180 minutes.

TABLES

Tables 1-4 provide data from the in vivo rabbit model and Tables 5-6 provide data from the in vivo primate model, both of which are described hereinabove. In the tables time is given in minutes, mean arterial pressure (MAP) is in mm Hg, and heart rate (HR) is in beats/minute. Baseline MAP and HR values are average values over the 5-minute interval prior to dosing.

TABLE 1

| Time | Baseline | 5 | 10 | 15 | 30 | 60 | 90 | 120 | 150 | 180 | 210 | 240 |
|---|---|---|---|---|---|---|---|---|---|---|---|---|
| MAP | 92 | 69 | 59 | 60 | 59 | 59 | 59 | 58 | 57 | 60 | 61 | 65 |
| HR | 243 | 268 | 283 | 285 | 284 | 288 | 284 | 278 | 275 | 273 | 273 | 273 |

TABLE 2

| Time | Baseline | 5 | 10 | 15 | 30 | 60 | 90 | 120 | 150 | 180 | 210 | 240 |
|---|---|---|---|---|---|---|---|---|---|---|---|---|
| MAP | 87 | 67 | 67 | 69 | 68 | 67 | 57 | 55 | 52 | 53 | 56 | 55 |
| HR | 260 | 296 | 296 | 296 | 291 | 293 | 282 | 282 | 279 | 285 | 284 | 297 |

TABLE 3

| Time | Baseline | 5 | 10 | 15 | 30 | 60 | 90 | 120 | 150 | 180 | 210 | 240 |
|---|---|---|---|---|---|---|---|---|---|---|---|---|
| MAP | 95 | 91 | 86 | 84 | 84 | 85 | 83 | 85 | 85 | 85 | 89 | 89 |
| HR | 291 | 289 | 299 | 302 | 306 | 300 | 301 | 304 | 301 | 298 | 307 | 306 |

TABLE 4

| Time | Baseline | 5 | 10 | 15 | 30 | 60 | 90 | 120 | 150 | 180 | 210 | 240 |
|---|---|---|---|---|---|---|---|---|---|---|---|---|
| MAP | 89 | 85 | 87 | 85 | 85 | 87 | 87 | 85 | 87 | 87 | 85 | 92 |
| HR | 260 | 258 | 260 | 262 | 262 | 255 | 253 | 246 | 246 | 246 | 247 | 257 |

TABLE 5

| Time | Baseline | 5 | 10 | 15 | 30 | 60 | 90 | 120 | 150 | 180 | 210 | 240 |
|---|---|---|---|---|---|---|---|---|---|---|---|---|
| MAP | 101 | 91 | 57 | 51 | 53 | 58 | 58 | 62 | 65 | 66 | 71 | 79 |
| HR | 161 | 203 | 206 | 187 | 190 | 180 | 180 | 183 | 187 | 187 | 191 | 193 |

TABLE 6

| Time | Baseline | 5 | 10 | 15 | 30 | 60 | 90 | 120 | 150 | 180 | 210 | 240 |
|---|---|---|---|---|---|---|---|---|---|---|---|---|
| MAP | 114 | 115 | 112 | 111 | 112 | 112 | 111 | 110 | 111 | 113 | 115 | 112 |
| HR | 177 | 179 | 176 | 173 | 179 | 179 | 178 | 181 | 182 | 184 | 191 | 188 |

The invention claimed is:

1. A method of treating glaucoma or ocular hypertension in a patient in need thereof, comprising administering to the patient a therapeutically effective amount of a selective $EP_4$ receptor agonist of Formula I

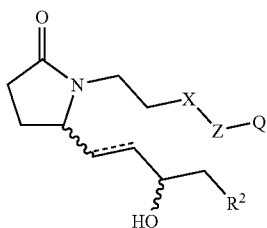

or a prodrug thereof, a pharmaceutically acceptable salt of the selective $EP_4$ receptor agonist or prodrug or a stereoisomer or diastereomeric mixture of the $EP_4$ receptor agonist, prodrug or salt, wherein:

-----is a single or double bond;

X is —CH$_2$— or O;
Z is thienyl
Q is carboxyl, (C$_1$-C$_4$)alkoxylcarbonyl or tetrazolyl;
$R^2$ is —Ar or —Ar$^1$—V—Ar$^2$;
V is a bond, —O—, —OCH$_2$— or —CH$_2$O—;
Ar is a partially saturated, fully saturated or fully unsaturated five to eight membered ring optionally having one to four heteroatoms selected independently from oxygen, sulfur and nitrogen, or a bicyclic ring consisting of two fused independently partially saturated, fully saturated or fully unsaturated five or six membered rings, taken independently, optionally having one to four heteroatoms selected independently from nitrogen, sulfur and oxygen, said partially or fully saturated ring or bicyclic ring optionally having one or two oxo groups substituted on carbon or one or two oxo groups substituted on sulfur; and
Ar$^1$ and Ar$^2$ are each independently a partially saturated, fully saturated or fully unsaturated five to eight membered ring optionally having one to four heteroatoms selected independently from oxygen, sulfur and nitrogen, said partially or fully saturated ring optionally having one or two oxo groups substituted on carbon or one or two oxo groups substituted on sulfur;
said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, (C$_1$-C$_7$)alkoxy, (C$_1$-C$_4$)alkoxy (C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$)- alkyl, (C$_3$-C$_7$)cycloalkyl(C$_1$-C$_4$)alkanoyl, formyl, (C$_1$-C$_8$)alkanoyl, (C$_1$-C$_6$)alkanoyl(C$_1$-C$_6$)alky-1, (C$_1$-C$_4$)alkanoylamino, (C$_1$-C$_4$)alkoxycarbonylamino, hydroxysulfonyl, aminocarbonylamino or mono-N—, di-N,N—, di-N,N'— or tri-N,N,N'—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar are optionally substituted on carbon with up to three fluoro atoms; and said Ar$^1$ and Ar$^2$ moieties are independently optionally substituted on carbon or nitrogen with up to three substituents each independently selected from hydroxy, halo, carboxy, (C$_1$-C$_7$)alkoxy, (C$_1$-C$_4$)alkoxy(C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$)alkyl, (C$_3$-C$_7$)cycloalkyl(C$_1$-C$_4$)alkanoyl, formyl, (C$_1$-C$_8$)alkanoyl, (C$_1$-C$_6$)alkanoyl (C$_1$-C$_6$)alkyl, (C$_1$-C$_4$)alkanoylamino, (C$_1$-C$_4$)alkoxycarbonylamino, hydroxysulfonyl, aminocarbonylamino or mono-N—, di-N,N—, di-N,N— or tri-N,N,N—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar$^1$ and Ar$^2$ are optionally substituted on carbon with up to three fluoro atoms.

2. A method of claim 1 wherein the selective $EP_4$ receptor agonist is a compound of Formula Ia

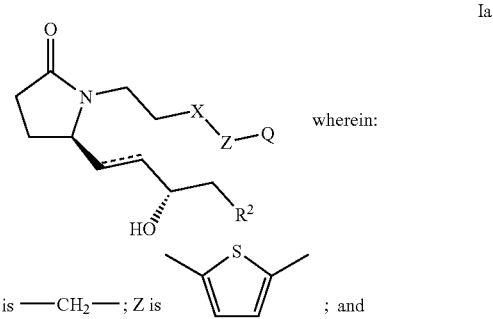

R is Ar wherein said Ar moiety is optionally substituted on carbon or nitrogen, on one ring if the moiety is monocyclic, or on one or both rings if the moiety is bicyclic, with up to three substituents per ring each independently selected from hydroxy, halo, carboxy, (C$_1$-C$_7$)alkoxy, (C$_1$-C$_4$)alkoxy(C$_1$-C$_4$)alkyl, (C$_1$-C$_7$)alkyl, (C$_2$-C$_7$)alkenyl, (C$_3$-C$_7$)cycloalkyl, (C$_3$-C$_7$)cycloalkyl(C$_1$-C$_4$) alkyl, (C$_3$-C$_7$)cycloalkyl(C$_1$-C$_4$)alkanoyl, formyl, (C$_1$-C$_8$)alkanoyl, (C$_1$-C$_6$)alkanoyl(C$_1$-C$_6$)alkyl, (C$_1$-C$_4$)alkanoylamino, (C$_1$-C$_4$)alkoxycarbonylamino, hydroxysulfonyl, aminocarbonylamino or mono-N—, di-N,N—, di-N,N'— or tri-N,N,N—(C$_1$-C$_4$)alkyl substituted aminocarbonylamino, sulfonamido, (C$_1$-C$_4$)alkylsulfonamido, amino, mono-N— or di-N,N—(C$_1$-C$_4$)alkylamino, carbamoyl, mono-N— or di-N,N—(C$_1$-C$_4$)alkylcarbamoyl, cyano, thiol, (C$_1$-C$_6$)alkylthio, (C$_1$-C$_6$)alkylsulfinyl, (C$_1$-C$_4$)alkylsulfonyl and mono-N— or di-N,N—(C$_1$-C$_4$)alkylaminosulfinyl, wherein said alkyl and alkoxy substituents in the definition of Ar$^1$ and Ar$^2$ are optionally substituted on carbon with up to three fluoro.

3. A method of claim 2 wherein the selective $EP_4$ receptor agonist is a compound of the Formula Ia, wherein Ar is cyclohexyl, 1,3-benzodioxolyl, thienyl, naphthyl or phenyl optionally substituted with one or two (C$_1$-C$_4$)alkyl, (C$_1$-C$_4$)alkoxy, (C$_1$-C$_4$)alkoxy(C$_1$-C$_4$)alkyl, chloro, fluoro, trifluoromethyl or cyano, wherein said alkyl and alkoxy substituents in the definition of Ar are optionally substituted with up to three fluoro.

4. A method of claim 3 wherein the selective EP$_4$ receptor agonist is a compound of the Formula Ia, wherein

----- is a single bond; Q is carboxy or (C$_1$-C$_4$)alkoxylcarbonyl; and Z is

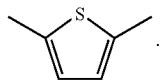

5. A method of claim 4 wherein the selective EP$_4$ receptor agonist is a compound of the Formula Ia, a prodrug thereof, a pharmaceutically acceptable salt of said compound or said prodrug or a stereoisomer or diastereomeric mixture of said compound, prodrug or salt, wherein Q is carboxy and Ar is phenyl optionally substituted with one (C$_1$-C$_4$)alkyl, (C$_1$-C$_4$) alkoxy, (C$_1$-C$_4$)alkoxy(C$_1$-C$_4$)alkyl, chloro, fluoro, trifluoromethyl or cyano, wherein said alkyl and alkoxy substituents in the definition of Ar are optionally substituted with up to three fluoro.

6. A method of claim 5 wherein the selective EP$_4$ receptor agonist is a compound of the Formula Ia, a prodrug thereof, a pharmaceutically acceptable salt of said compound or said prodrug or a stereoisomer or diastereomeric mixture of said compound, prodrug or salt, wherein Ar is 3-trifluoromethylphenyl.

7. A method of claim 5 wherein the selective EP$_4$ receptor agonist is a compound of the Formula Ia, a prodrug thereof, a pharmaceutically acceptable salt of said compound or said prodrug or a stereoisomer or diastereomeric mixture of said compound, prodrug or salt, wherein Ar is 3-chlorophenyl.

8. A method of claim 5 wherein the selective EP$_4$ receptor agonist is a compound of the Formula Ia, a prodrug thereof, a pharmaceutically acceptable salt of said compound or said prodrug or a stereoisomer or diastereomeric mixture of said compound, prodrug or salt, wherein Ar is 3-trifluoromethoxyphenyl.

9. A method of claim 5 wherein the selective EP$_4$ receptor agonist is a compound selected from the group consisting of 5-(3-(2S-(3R-hydroxy-4-(3-trifluoromethylphenyl)butyl)-5-oxo-pyrrolidin-1-yl)propyl)thiophene-2-carboxylic acid; 5-(3-(2S-(3R-hydroxy-4-(3-trifluoro-methoxyphenyl)butyl)-5-oxo-pyrrolidin-1-yl)propyl)thiophene-2-carboxylic acid; and 5-(3-(2S-(4-(3-chloro-phenyl)-3R-hydroxy-butyl)-5-oxo-pyrrolidin-1-yl)propyl)thiophene-2-carboxylic acid.

* * * * *